US007601494B2

(12) United States Patent
Tian et al.

(10) Patent No.: US 7,601,494 B2
(45) Date of Patent: Oct. 13, 2009

(54) METHOD OF SCREENING CANDIDATE COMPOUNDS FOR SUSCEPTIBILITY TO BILIARY EXCRETION

(75) Inventors: Xianbin Tian, Chapel Hill, NC (US); Peijin Zhang, Apex, NC (US); Kim L. R. Brouwer, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 408 days.

(21) Appl. No.: 10/842,404

(22) Filed: May 10, 2004

(65) Prior Publication Data

US 2005/0048464 A1 Mar. 3, 2005

Related U.S. Application Data

(63) Continuation-in-part of application No. 09/527,352, filed on Mar. 17, 2000, now Pat. No. 6,780,580.

(60) Provisional application No. 60/124,810, filed on Mar. 17, 1999.

(51) Int. Cl.
*C12Q 1/68* (2006.01)
*C12N 5/08* (2006.01)
*C12N 5/10* (2006.01)
*C07H 21/04* (2006.01)

(52) U.S. Cl. ............................ 435/6; 435/375; 435/370; 536/24.5

(58) Field of Classification Search ...................... 435/6, 435/375, 370; 536/24.5
See application file for complete search history.

(56) References Cited

U.S. PATENT DOCUMENTS 5,504,086 A 4/1996 Ellinwood, Jr. et al.

(Continued)

FOREIGN PATENT DOCUMENTS

| NZ | 513773 | 6/2004 |
|---|---|---|
| WO | WO 94/12662 | 6/1994 |
| WO | WO 96/01426 | 1/1996 |
| WO | WO 00/55355 | 9/2000 |

OTHER PUBLICATIONS

Ahlquist, "RNA-dependent RNA polymerases, viruses and RNA silencing," Science 296:1270-1273, 2002.*

(Continued)

*Primary Examiner*—Karen Cochrane Carlson
*Assistant Examiner*—Rosanne Kosson
(74) *Attorney, Agent, or Firm*—Jenkins, Wilson, Taylor & Hunt, P.A.

(57) ABSTRACT

A method of screening a candidate compound for susceptibility to biliary excretion by a hepatocyte transport protein. The method includes the steps of providing a culture of hepatocytes comprising a transport protein, the culture having at least one bile canaliculus; exposing a candidate compound to the culture; and determining an amount of candidate compound in the at least one bile canaliculus, the amount of candidate compound in the at least one bile canaliculus indicating the susceptibility of the candidate compound to biliary excretion by the transport protein. In some embodiments determining the amount of candidate compound in the bile canaliculus comprises inhibiting expression of the transport protein, measuring the amount of candidate compound in the bile canaliculus and comparing amounts of compound in the canalicules with and without inhibition of the transport protein. A difference in the amount of candidate compound in the canaliculus indicates susceptibility of the candidate compound to biliary excretion by the transport protein. In one embodiment, expression of the transport protein is inhibited through introduction of a RNA having a sequence corresponding to a coding strand of the gene encoding the transport protein into the hepatocyte. Optionally, the culture of hepatocytes is a long-term culture in a sandwich configuration. The method is particularly applicable to the screening of multiple candidate compounds in a single effort.

28 Claims, 17 Drawing Sheets

U.S. PATENT DOCUMENTS

| | | | |
|---|---|---|---|
| 5,602,026 | A | 2/1997 | Dunn et al. |
| 6,297,216 | B1 * | 10/2001 | Sarkadi et al. ............... 514/17 |
| 6,780,580 | B2 | 8/2004 | LeCluyse et al. |
| 2006/0211638 | A1 * | 9/2006 | Imoto et al. .................. 514/44 |

OTHER PUBLICATIONS

Chen et al., "Genomic organization of the human multidrug resistance (MDR1) gene and origin of P-glycoproteins," J Biol Chem 265(1):506-514, 1990.*

Chan et al., "Inhibition of P-glycoprotein expression and reversal of drug resistance of human hepatoma HepG2 cells by multidrug resistance gene (mdr1) antisense RNA," Life Sci 67:2117-2124, 2000.*

Australian Office Communication corresponding to a Australian Patent Application Serial No. 2005225094 dated Apr. 4, 2007.

Australian Search Report for corresponding Australian patent application 40145/00 dated Feb. 4, 2005.

Office Action corresponding to a European Patent Application No. 06002377.7 dated Dec. 17, 2007.

New Zealand Examiners Report for corresponding New Zealand Patent Application No. 538038.

European Office Action corresponding to European pat. app. No. 00919459.8 dated Apr. 25, 2005.

European Search Report corresponding to application No. 06002377.7-2402 dated Jun. 2, 2006.

Liu et al., "Prediction of in vivo biliary excretion of model compounds from hepatocytes cultured in a sandwich configuration", *Pharmaceutical Research*, 14: S459, 1997.

Liu et al., "Hepatocytes cultured in a 1-17 sandwich configuration (SC) as an in vitro model of biliary excretion: effects of Ca2+ on taurocholate (TC) uptake and retention", *Hepatology*, 26: 297A, 1997.

Liu et al., "Biliary excretion of taurocholate (TC) in rat hepatocytes cultured in a collagen sandwich configuration", *Hepatology*, 24: 370A, 1996.

Talamini et al., "Repolarization of hepatocytes in culture", *Hepatology*, 25: 167-172, 1997.

Liu et al., "Correlation of biliary excretion in sandwich-cultured rat hepatocytes and in vivo in rats", *Drug Metabolism and Disposition*, 27:637-644, 1999.

Liu et al., "Biliary excretion in primary rat hepatocytes cultured in a collagen-sandwich configuration", *American Journal of Physiology*, 277: g12-g21, 1999.

Liu et al., "Use of Ca2+ modulation to 1-17 evaluate biliary excretion in sandwich-cultured rat hepatocytes", *Journal of Pharmacology and Experimental Therapeutics*, 289: 1592-1599, 1999.

Memo Concerning the Official Action for Mexican Patent Application No. PA/a/2001/009213 dated May 30, 2005.

Lindgren et al., Insulin-like growth factor I correlates with protein intake estimated from the normalized protein catabolic rate in hemodialysis patients, *Am. J. Nephrology* 20:255-262 (2000).

Sandusky et al., Expression of multidrug resistance-associated protein 2 (MRP2) in normal human tissues and carcinomas using tissue microarrays, *Histopathology* 41:65-74 (2002).

Kool et al., MRP3, an organic anion transporter able to transport anti-cander drugs, *Proc. Natl. Acad. Sci. USA* 96:6914-6919 (Jun. 1999).

Norris et al., Expression of the geen for multidrug-resistance-associated protein and outcome in patients with neuroblastoma, *MRP Gene Expression and Prognosis in Neuroblastoma* 334(4):231-238 (Jan. 25, 1996).

LeCluyse et al., Formation of extensive canalicular networks by rat hepatocytes cultured in collagen-sandwich configuration, *Am. J. Physiol.* 266:C1764-C1774 (1994).

Poole et al., In vivo biliary excretion and in vitro cellular accumulation of thyroxine by rats or cultured rat hepatocytes treated with a novel histamine $H_1$-receptor antagonist, *Archives of Toxicology* 64:474-481 (1990).

Liu et al., Partial Maintenance of Taurocholate Uptake by Adult Rat Hepatocytes Cultured in a Collagen Sandwich Configuration, *Phamaceutical Research* 15(10)1533-1539 (1998).

Liu et al., Biliary Excretion in Sandwich-Cultured (SC) Hepacytes: A Novel in vitro Model System for Investigating Biliary in Excretion, *AAPS Graduate Symposium in Pharmacokinetics, Pharamcodynamics and Drug Metabolism* No. 1374 (Nov. 16, 1998) (Abstract).

Liu et al., Hepatocytes Cultured in a Sandwich Confirguration (SC) as an in vitro Model of Biliary Excretion: Effects of $Ca^{++}$ on Taurocholate (TC) Uptake and Retention, *Hepatology* 26(4):No. 675 (1997) (Abstract).

Liu et al., *Prediction of in vivo Biliary Excretion of Model Compounds from Hepatocytes Cultured in a Sandwich Configuration*, S-459 3007 (Abstract).

Liu et al., Biliary Excretion of Taurocholate (TC) in Rat Hepatocytes Cultured in a Collagen Sandwich Configuration (SC), *Hepatology*, AASLD Abstracts No. 973 (Oct. 1996) (Abstract).

Talamini et al., Repolarization of Heaptocytes in Culture, *Hepatology* 25:167-172 (1997).

Liu et al., Correlation of Billary Excretion in Sandwich-Cultured Rat Hepatocytes and in vivo in Rats, *Drug Metabolism and Disposition* 27(6):637-644 (1999).

Liu et al., Biliary excretion in primary rat hepatocytes cultured in a collagen-sandwich configuration, *Am. J. Physiol* 277:G12-G21 (1999).

Liu et al., Use of $CA^{2+}$ Modulation to Evaluate Biliary Excretion in Sandwich-Cultured Rat Hepatocytes, *J. of Pharmacology and Experimental Therapeutics* 289(3):1592-1599 (1999).

Liu et al., Taurocholate (TC) Uptake in Rat Hepatocytes Cultured in a Collagen Sandwich Configuration (SC), *Pharm. Res. Init.* 13:S-393 No. 8003 (1996) (Abstract).

Correspondence from Japanese Associates regarding a Japanese Office Communication corresponding to a Japanese Patent Application Serial No. 2000-605772 dated Sep. 25, 2007.

Invitation to Pay Additional Fees and, Where Applicable, Protest Fee for International Application No. PCT/US05/16240 dated Apr. 28, 2008.

Official Action corresponding to Canadian Patent Application No. 2,365,398 dated Apr. 24, 2008.

Kupferberg, "Inhibition of tritium-labeled ouabain uptake by liver slices and its excretion into the bile and by compounds having a steroid nucleus," Life Sciences, vol. 8, No. 21, pp. 1179-1185 (Abstract, one page).

Notification of Transmittal of the International Search Report and the Written Opinion of the International Searching Authority, or the Declaration corresponding to International Application No. PCT/US05/16240 dated Jul. 7, 2008.

Hagenbuch et al., "Molecular closing, chromosomal localization, and functional characterization of a human liver Na+/bile acid cotransporter," J. Clin. Invest., vol. 93, pp. 1326-1331 (Mar. 1994).

Stryer, Lubert, Biochemistry, ed., W. H. Freeman and Co., San Francisco, 1975, Chap. 6, pp. 129-133.

Official Action corresponding to U.S. Appl. No. 09/527,352 dated Jan. 2, 2004.

Official Action corresponding to U.S. Appl. No. 09/527,352 dated Aug. 8, 2003.

Official Action corresponding to U.S. Appl. No. 09/527,352 dated Jan. 27, 2003.

Official Action corresponding to U.S. Appl. No. 09/527,352 dated Jul. 12, 2002.

Official Action corresponding to U.S. Appl. No. 09/527,352 dated Dec. 4, 2001.

Official Action corresponding to U.S. Appl. No. 09/527,352 dated Mar. 13, 2001.

Notice of Allowance corresponding to U.S. Appl. No. 09/527,352 dated Apr. 26, 2004.

Official Action corresponding to U.S. Appl. No. 10/855,085 dated Jun. 26, 2007.

Official Action corresponding to U.S. Appl. No. 10/855,085 dated Sep. 28, 2006.

Official Action corresponding to U.S. Appl. No. 10/854,963 dated May 22, 2008.

Official Action corresponding to U.S. Appl. No. 10/854,963 dated Jun. 15, 2007.

Official Action corresponding to U.S. Appl. No. 10/854,963 dated Sep. 20, 2006.

* cited by examiner

Cy3-labeled siMrp2

Cy3-labeled siFL

SEQUENCE LISTING

<160> NUMBER OF SEQ ID NOS: 7

<210> SEQ ID NO 1
<211> LENGTH: 4918
<212> TYPE: DNA
<213> ORGANISM: Rattus norvegicus

<400> SEQUENCE: 1

```
tgcactttaa catctgcttt cccagaggaa aaagtaaagg agaaacagta caatcataga        60
agagtcttcg taacagaagc gcgaggagag cattatggac aagttctgca actctacttt       120
ttgggatctc tcattactgg aaagtccaga ggctgacctg cctctttgtt ttgagcaaac       180
tgttctggtg tggattccct tgggctttct ttggctcctg gctccttggc aactttacag       240
cgtgtacaga tccaggacca agagatcttc tataaccaaa ttctaccttg ccaagcaggt       300
gttcgtcgtg tttcttctta ttttagcagc catagacctg tctcttgcgc tcacagaaga       360
tactggacaa gccacagttc ctcctgtcag atatacgaat ccaatcctct acctgtgcac       420
atggctcctg gttttggcag tccagcacag caggcaatgg tgtgtacgaa agaacttcg        480 gttcctgtct ctgttctgga tcctctcggt cttatgcggc gtattccagt ttcagactct       540
gatacgagca ctcctgaagg acagcaagtc caacatggcc tactcctacc tgttcttcgt       600
ctcctacggt ttccagattg tcctcctgat tcttacagcc ttttcaggac caagtgactc       660
aacacaaact ccatcagtca cggcttcctt tctgagtagc attacattta gttggtatga       720
```

-continued

```
caggactgtt ctgaaaggtt acaagcatcc actgacacta aagatgtct gggatatcga    780
tgaagggttt aaaacaaggt cagtcaccag caagtttgag gcggccatga caaaggacct    840
gcagaaagcc aggcaggctt ttcagaggcg gctgcagaag tcccagcgga aacctgaggc    900
cacactacac ggactgaaca agaagcagag tcagagccaa gacgttctcg tcctggaaga    960
agcgaaaaag aagtctgaga agaccaccaa agactatccc aaatcgtggt tgatcaagtc   1020
tctcttcaaa accttccacg tagtgatcct gaaatcattt atactgaaat aatacatga   1080
ccttttggtg tttctgaatc ctcagctgct gaagttgctg atcggtttcg tgaagagctc   1140
taactcatac gtgtggtttg gctatatctg tgcaatccta atgtttgctg tgactctcat   1200
ccaatctttc tgccttcagt cttactttca acattgtttt gtgttgggaa tgtgcgtacg   1260
gacaaccgtc atgtcttcga tatataagaa ggcattgacc ctatctaact ggctaggaa   1320
gcagtacacc attggagaga cggtgaactt gatgtctgta gattcccaga agctaatgga   1380
tgcgaccaac tacatgcagt tggtgtggtc aagtgttata cagattactt tgtccatctt   1440
cttcctgtgg agagagttgg gaccgtccat cttagcaggt gttggggtta tggttctcct   1500
aatcccagtt aatggagttc tggctaccaa gatcagaaat attcaggtcc aaaatatgaa   1560
gaataaagac aaacgtttaa aaatcatgaa tgagattctc agtggaatca agatcctgaa   1620
atactttgcc tgggaacctt catttcaaga gcaagtccag ggcattcgga gaaagaact   1680
caagaacttg ctgcggttcg gccagctgca gagtctgctg atcttcattt tacagataac   1740
tccaatcctg gtgtctgtgg tcacattttc tgtctatgtc ctggtggata cgccaatgt   1800
tttgaatgcg gagaaggcat ttacctccat caccctcttc aatatcctac gcttccctct   1860
gtccatgctt cccatggtga cctcatcgat cctccaggcc agtgtttctg tggaccggct   1920
ggagaggtat ttgggaggag acgatttaga cacatctgcc attcgccgcg tcagcaattt   1980
tgataaagct gtgaagtttt cagaggcctc ttttacttgg gacccggact ggaagccac   2040
aatccaagat gtgaacctgg acataaagcc aggccaactg gtggctgtgg tgggcactgt   2100
aggctctggg aaatcctctt tggtatcagc catgctggga gaaatggaaa acgttcacgg   2160
gcacatcacc atccagggat ccacagccta tgtccctcag cagtcctgga ttcagaatgg   2220
aaccatcaaa gacaacatcc tgtttgggtc cgaatacaat gaaaagaagt accagcaagt   2280
tctcaaagca tgcgctctcc tcccagactt ggaaatattg cctggaggag acatggctga   2340
gatcggagag aaggggataa atctcagtgg tggtcagaag cagcgagtca gcctggccag   2400
agctgcctat caagatgctg acatctatat tctggacgat cccctgtcgg ctgtggatgc   2460
tcatgtggga aaaacatttt tcaacaaggt tgtgggcccc aacggcctgt ggctggcaa   2520
gacgagaatc tttgttactc atggtattca cttccttccc caagtggatg agattgtagt   2580
tctggggaaa ggcaccatct tagagaaagg atcctatcgt gacctgttgg acaagaaggg   2640
agtgttttgct aggaactgga agaccttcat gaagcattca gggcctgaag agagggccac   2700
agtcaataat gacagtgagg cggaagacga cgatgatggg ctgattccca ccatggagga   2760
aatccctgag gatgcagctt ccttggccat gagaagagaa aatagtcttc gccgtacact   2820
gagccgcagc tctaggtcca gcagccgacg tgggaagtcc ctcaaaaact ccttgaagat   2880
taaaaatgtg aatgtcttga aggagaagga aaaagaagtg aaggacaaa aactaattaa   2940
gaaagaattt gtgaaaccg ggaaggtcaa gttctccatc tacctgaagt atctacaggc   3000
agtagggtgg tggtccatac ttttcatcat ccttttctac ggattgaata atgttgcttt   3060
```

```
tatcggctct aacctctggc tgagtgcttg gaccagtgac tctgacaact tgaatgggac    3120
caacaattcg tcttctcata gggacatgag aattggggtc tttggagctc tgggattagc    3180
acaaggtata tgtttgctta tttcaactct gtggagcata tatgcttgca gaaatgcatc    3240
aaaagctttg cacgggcagc tgttaaccaa catcctccgg gcacccatga ggttttttga    3300
cacaactccc acaggccgga ttgtgaacag attttctggt gatatttcta ctgtggacga    3360
cttgctcccc cagacacttc gaagctggat gatgtgtttc tttggcatcg ctggcactct    3420
tgtcatgatc tgcatggcca ccccagtctt cgctatcatc atcattcctc tcagcattct    3480
ttatatttcg gtgcaggttt tttatgtggc tacttcccgc cagctgagac ggttggattc    3540
tgtcaccaaa tctccgatct attctcactt cagtgagact gtcacaggtt tgcccattat    3600
ccgtgccttt gagcaccagc agcgatttct agcttggaat gagaagcaga ttgacatcaa    3660
ccagaaatgt gtctttttcct ggattacctc caacaggtgg cttgcaattc ggctggagct    3720
ggttggaaac ttggtcgtct tctgttccgc cttgctgctg gttatttata gaaaaacctt    3780
aaccggggac gttgtgggct tgttctgtc caacgccctc aatatcacac aaaccttgaa    3840
ctggctagtg aggatgacgt cagaagcaga gaccaacatt gtggcagttg agcgaataag    3900
tgaatacata aatgtagaga atgaggcgcc ctgggtgact gacaagaggc ctccggcaga    3960
ctggcccaga catggtgaga tccagtttaa caactatcaa gtgcggtatc ggccggagct    4020
ggatctggta ctgaaaggga tcacttgtaa catcaagagc ggagagaagg tcggcgtagt    4080
gggcaggact ggggctggga aatcatccct cacaaactgc ctcttcagaa tcttagagtc    4140 tgcgggggc cagatcatca ttgatgggat agatgttgcc tccattggac tgcacgacct    4200
tcgagagagg ctgaccatca ttccccagga ccccatttg ttctcgggga gtctgaggat    4260
gaatctcgac cctttcaaca aatattcaga tgaggaggtt tggagggccc tggagttggc    4320
tcacctcaga tcctttgtgt ctggcctaca gcttgggttg ttatccgaag tgacagaggg    4380
tggtgacaac ctgagcatag ggcagaggca gctcctatgc ctgggcaggg ctgtgcttcg    4440
aaaatccaaa atcctggtcc tggatgaagc cacggctgca gtggatctcg agacggatag    4500
cctcattcag acgaccatcc gaaaggagtt ctcccagtgc acggtcatca ccatcgctca    4560
caggctgcac accatcatgg acagtgacaa gataatggtc ctagacaacg gaagattgt    4620 cgagtatggc agtcctgaag aactgctgtc caacagaggt tccttctatc tgatggccaa    4680
ggaagccggc attgaaaatg tgaatacaca agagctctag cagctggttc cgtggctggc    4740
ggactataag aacagtttct attatttgct ttggtttctg tgactgtgct ctaggtgcaa    4800
agacacatat tttgttcccg ttgctcaggc tggcctcaaa ctctaaggct ccagcaatct    4860
ctggtctcag ccagagacct gtaaaaatag acacttcaaa gattatcatg aataaata     4918
```

<210> SEQ ID NO 2
<211> LENGTH: 5174
<212> TYPE: DNA
<213> ORGANISM: Rattus norvegicus

<400> SEQUENCE: 2

```
gggttgagct gaactgagat cccaagacca gcggtgcacc agagccacat ggaccgcttg      60
tgcggctccg gggagctggg ctccaagttc tgggactcca acctgactgt ataaccaac     120 actccagacc tcacaccctg tttccagaac tccttgctgg cctgggttcc ctgcatctat     180
ctgtgggctg ccttgccctg ctacctgttc tacctgaggc accatcggct tggctacata     240
gtcctctcat gcttatccag gctcaagacg gccctcggtg ttctgctgtg gtgtatctca     300
```

```
tgggtggacc tgttctactc cttccatggc ctggttcacg gctcatcccc tgctcctgtc    360
ttctttatca caccettgtt ggtggggatc accatgctgc tggccacatt gctaatccag    420
tatgagcggc ttcggggcgt gcggtcttca ggtgtgctca tcatcttctg gctcctgtgt    480
gtgatctgtg ccatcatccc cttccgttcc aagatcctct ggctttggc agagggtaaa     540 atcttggatc cgttccgatt caccactttc tacatctact tcgccctcgt gctgtgtgcc    600
ttcatcctgt cctgcttcca ggagaagccg cctttgtttt ccccagagaa tcttgacaca    660
aatccttgcc cagaggccag cgctggcttc ttctcccgtc tgtctttctg gtggttcaca    720
aagcttgcca tccttggcta ccgacgtccc ctggaggaca gtgacctctg gtctctgtct    780
gaggaggact gctctcacaa ggtggtacaa cggctactgg aagcatggca aaagcagcag    840
acccaagcat cagggcccca gactgcagcc cttgagccaa gatcgcagg tgaggatgag     900 gtcctgctga aggcccgccc caagaccaag aagccttcct ttctgagggc tttggtgaga    960
accttcacct ccagcttgct catgggtgcc tgcttcaagc tgatccagga cctgctctcc   1020
ttcatcaacc cacagctgct cagcatcctc atcaggttta tttctgaccc cacggcccct   1080
acctggtggg gcttcttgct ggccggactg atgttcgtga gctccaccat gcagacattg   1140
atcttacacc aacattacca ctgcatcttt gtgatggcct tgaggatacg gactgctatc   1200
ataggcgtca tctacaggaa ggctctgacc atcaccaact cagtcaaacg tgagtacact   1260
gtgggagaaa tggtcaacct catgtcggtg gacgcccagc gcttcatgga tgtctcccca   1320
ttcatcaacc tgctgtggtc tgcacctttg caggtcatcc tggcgatata cttcctctgg   1380
cagatcttag gcccatcagc cctggctggg gtggctgtga tagtcttgct gataccactc   1440 aatgagctg tgtccatgaa atgaagacc taccaggtac agcaaatgaa gttcaaagac     1500
tcccgcatca aactgatgag tgagatcctg aatggcatca agttctgaa gctgtacgct    1560 tgggagccca ccttcttgga gcaggtagaa ggaatcaggc agggtgagct ccagctactg   1620
cggaagggcg cctacctgca ggctatctct accttcatct gggtctgcac ccgtttatg    1680 gtgaccctga tcaccctcgg ggtgtacgtg tgtgtggaca gaacaatgt gctggatgct    1740 gagaaggcct tcgtgtccct gtccttgttc aatatcttaa agatcccccct caacctgctg  1800 cctcagttaa tcagtggcat gacccagacc agcgtgtctc tgaaacggat ccaggatttc   1860
ctgaaccaag atgaacttga cccccagtgt gtggaaagaa agaccatctc cccaggccgt   1920
gccatcacca tacacaacgg caccttctcc tggtccaagg acctgcctcc cacccttcac   1980
agcctaaaca ttcaaatccc gaaggggggca ttggtggctg tggtgggacc tgtgggctgt  2040
gggaagtctt ccctggtgtc tgccttgctc ggagagatgg agaagctgga aggtgcagtg   2100
tctgtaaagg gctctgtggc ctacgtgccc cagcaggcgt ggatccagaa ctgcacactt   2160
caggaaaatg tgctatttgg ccaacccatg aaccccaagc gctaccaaca ggctctggag   2220
acgtgtgccc tgctagctga cctagatgtg cttcctggtg gggaccagac agagattgga   2280
gagaagggca ttaacctatc tggaggccag cgacaacggg tgagtttggc ccgagctgtt   2340
tatagtgacg ccaacatttt tttgctggat gacccactgt cggctgtgga ctctcacgtg   2400
gctaagcata tcttcgacca agtgattgga ccagaaggtg tgctggcagg caagactcgg   2460
gtgctggtaa cccatggcat cagcttcctg ccccagacgg actttatcat tgtgcttgct   2520
gacggacaga ttactgagat gggtcactac tccgaactcc tgcagcacga tggctccttt   2580
gccaacttcc tccgaaacta tgcaccagat gaaaaccagg aggccaatga aggagtcttg   2640
```

```
caacatgcaa atgaggaggt gctcctgctt gaagacacac tcagcaccca cacagacctg    2700
acagacaccg agccagccat atacgagatc cgcaagcagt tcatgagaga gatgagctcc    2760
ttgtcttctg aaggagaggg ccagaaccgg cctgtgctca agagatatac gagttcactg    2820
gagaaggagg tgccggcgac acagactaaa gagactggtg cattaatcaa agaggagatc    2880
gcagagacag gcaatgtgaa gctgagcgtg tactgggatt atgccaagtc tgtgggctc     2940 tgcaccacgc tgtttatctg cctcctgtat gctggccaaa atgcggttgc tatcggagcc    3000
aatgtgtggc tcagtgcctg gaccaatgat gtggaggaac atggccagca gaacaacacc    3060
tccgtaaggc tgggagtcta cgccacccta ggaatactgc aagggctcct ggtcatgctg    3120
tcggccttca ccatggtggt tggcgctatc caggctgccc gcctgctgca cacagctctg    3180
ttgcacaacc agatccgtgc gcctcagtcc ttctttgaca cgacgccctc aggccgcatc    3240
ctcaatcgtt tctccaagga catatacgtc atcgatgagg ttctggcccc caccatcctc    3300
atgctgttca attcattcta cacatccatc tccaccattg tggtcatcgt ggccagcacg    3360
ccactcttct gcgtggttgt tcttcctctg gctgtgttct atggcttcgt gcagcgcttc    3420
tatgtggcca catcgaggca gctgaagaga ctggaatccg ttagccgctc gcccatcttc    3480
tcccacttct cggagacagt aactggcacc agtgtcattc gggcctacgg ccgagtccaa    3540
gacttcaagg tcctcagtga tgctaaggtg atagcaacc agaagaccac ttatccttac    3600
atcgcctcca accggtggct gggtgtccac gtggagtttg tggggaactg cgtggtgctc    3660
ttctccgcgc tgtttgcagt gatcgggaga aacagcttga atccagggct tgtgggtctt    3720
tccgtgtcct atgccttaca ggtgaccttg agtttgaatt ggatgatacg gacgctatcc    3780
gacctggagt ctaatatcat agccgtggag agagtcaagg agtactctaa gacggagact    3840
gaggctccct gggtgttgga gagcaaccgt gctccagaag gctggccag  gagtgggtg    3900 gtagagttcc ggaactattc ggtgcggtac cgcccgggcc tcgagttggt gctgaagaat    3960
ttgactctgc atgtgcaggg tgggagaag gtaggcatcg tgggccgcac tggggctggc    4020
aaatcttcca tgactctttg cctattccga atcctggagg ccgcagaggg tgagatcttc    4080
attgacgggc tcaatgtggc acacattggc ctccatgacc tgcgttcaca actcaccatc    4140
atccctcagg accccatcct gttctcgggc acgctgcgca tgaacctcga tcccttggc    4200 cgttactcgg acgaggacat ctggaggacc ctggagctat cccacctgag tgcatttgtg    4260
agcagccagc cgacaggcct ggattttcag tgctctgagg gtgggataa tctcagtgtt    4320 ggccagaggc agctcgtgtg cctagcccga gccctgctcc gaaagagccg tgtcctggtt    4380
ttagacgagg ccaccgctgc cattgacctg gagactgatg acctcatcca gggtaccatc    4440
cgtacccagt ttgaagactg cactgtactg accatcgccc accggctcaa cacaatcatg    4500
gactacaacc gggtcctggt cttggacaaa ggagtagtag ctgaatttga ttctccagta    4560
aacctcattg cagctggagg catcttctat gggatggcca agatgcagg  actcgcctag    4620 aatctgcatt ccaaaggttt cttccttgtc tgaatcggac agcaagtagc tgcagcatgg    4680
atttgatggc aacgagtggg gacatttgag ttggttttgg tttttttttg tttttgtttt    4740
tttttttttt tttaaattct gcaaattgcc ttacagacta gccatactta acagtggaat    4800
gaggaagtgg gtccttggag gtcacagcca gttcacagcc aagttcagac cagtccctgg    4860
gtctcctaga cctagtctac cattattccc gtactgcatt ttttttggt tctttttttc     4920 agagctgggg accgaaccca gggccttgcc cttcctaggt aagcgctcta ccactgagct    4980
aaatccccag ccccgtact gcagttttta agagaccctg ctcctgcctc tacatattca    5040
```

```
tagtttccaa ttttttttt aaatgagcct ttctccttct ggaccaggga ctgctaggtc    5100
agtctgtccg gggaacagaa tccctggttg gtgctgtctg aatccactga cgaaataaag    5160
ccatgagcag cagc                                                      5174

<210> SEQ ID NO 3
<211> LENGTH: 21
<212> TYPE: RNA
<213> ORGANISM: Artificial
<220> FEATURE:
<223> OTHER INFORMATION: siRNA designed to correspond to a short segment
      of the coding strand of rat Mrp2.

<400> SEQUENCE: 3
ggcuauaucu gugcaauccu a                                               21

<210> SEQ ID NO 4
<211> LENGTH: 21
<212> TYPE: RNA
<213> ORGANISM: Artificial
<220> FEATURE:
<223> OTHER INFORMATION: siRNA designed to correspond to a short segment
      of the coding strand of rat Mrp2.

<400> SEQUENCE: 4
ggcuaggaag caguacacca u                                               21

<210> SEQ ID NO 5
<211> LENGTH: 21
<212> TYPE: RNA
<213> ORGANISM: Artificial
<220> FEATURE:
<223> OTHER INFORMATION: siRNA designed to correspond to a short segment
      of the coding strand of rat Mrp2.

<400> SEQUENCE: 5
ggcaguaggg uggugucca u                                                21

<210> SEQ ID NO 6
<211> LENGTH: 21
<212> TYPE: RNA
<213> ORGANISM: Artificial
<220> FEATURE:
<223> OTHER INFORMATION: siRNA designed to correspond to a short segment
      of the coding strand of rat Mrp3.

<400> SEQUENCE: 6
gguccaagga ccugccuccc a                                               21

<210> SEQ ID NO 7
<211> LENGTH: 21
<212> TYPE: RNA
<213> ORGANISM: Artificial
<220> FEATURE:
<223> OTHER INFORMATION: siRNA designed to correspond to a short segment
      of the coding strand of firefly (Photinus pyralis) luciferase

<400> SEQUENCE: 7
gugcgcugcu ggugccaacu u                                               21
```

METHOD OF SCREENING CANDIDATE COMPOUNDS FOR SUSCEPTIBILITY TO BILIARY EXCRETION

RELATED APPLICATION INFORMATION

This application is a continuation-in-part of U.S. Utility patent application Ser. No. 09/527,352, filed Mar. 17, 2000, now U.S. Pat. No. 6,780,580 the disclosure of which is incorporated herein by reference in its entirety and which claims the benefit of and priority to U.S. Provisional Patent Application 60/124,810, filed Mar. 17, 1999, the disclosure of which is incorporated herein by reference in its entirety.

GRANT STATEMENT

This invention was made in part from government support under Grant No. GM41935 from the National Institute of Health. Thus, the U.S. Government has certain rights in the invention.

TECHNICAL FIELD

The present disclosure relates to a method of screening compounds, which are candidates primarily for use as therapeutic agents, for susceptibility to biliary excretion. More particularly, in some embodiments the present disclosure relates to an in vitro method of screening candidate compounds for susceptibility to biliary excretion. Compounds can be chosen for use as therapeutic agents for administration to humans and other warm-blooded vertebrates. In some embodiments the present disclosure relates to the identification of transport proteins involved in hepatobiliary disposition (such as but not limited to hepatic uptake and biliary excretion).

| Table of Abbreviations | |
|---|---|
| AUC | area under the curve |
| BCRP | breast cancer resistance protein |
| BSEP | bile salt export pump |
| $Cl_B$ | biliary clearance |
| $Cl_{in}$ | intrinsic clearance |
| cMOAT | canalicular multispecific organic anion transporter |
| CDF | carboxydichlorofluorescein |
| CFDA | carboxydichlorofluorescein diacetate |
| DMEM | Dulbecco's modified Eagle's medium |
| EDTA | ethylenediamine tetraacetate |
| HP | Hewlett Packard |
| HPLC | high performance liquid chromatography |
| hr | hour |
| i.v. | intravenous |
| i.p. | intraperitoneal |
| $K_m$ | Michaelis-Menten constant for enzyme-substrate reaction |
| LC/MS | liquid chromatography/mass spectrometry |
| mg pr. | milligrams protein |
| min | minute(s) |
| MDR2 or Mdr2 | multidrug resistance protein 2 |
| MRP2 or Mrp2 | multidrug resistance associated protein 2 |
| Ntcp | Na⁺/taurocholate cotransporting polypeptide |
| OAT | organic anion transporter |
| OATP1 | organic anion transporting polypeptide 1 |
| OATP2 | organic anion transporting polypeptide 2 |

| Table of Abbreviations -continued | |
|---|---|
| OCT | organic cation transporter |
| P-gp | P-glycoprotein |
| SD | standard deviation |
| UV | ultraviolet |
| UV/VIS | ultraviolet/visible |
| $V_{max}$ | maximum velocity of enzyme-catalyzed reaction |

BACKGROUND ART

First-pass metabolism pertains to the absorption of therapeutic agents, drugs or other compounds into the portal blood supply that leads to the liver. When a drug is swallowed, the stomach and small intestine absorb it, with subsequent flow in the blood to the portal vein entry to the liver. The liver may then in turn rapidly absorb and metabolize the drug at high concentrations through the liver blood supply. Thus, large amounts of the drug may never be seen by the systemic circulation or drug effect site. Additionally, rapid metabolism via the first-pass metabolism route can lead to the formation of high plasma concentrations of unwanted metabolites.

Thus, in the liver, therapeutic compositions are often undesirably removed from an animal's circulatory system in that they are taken up by hepatocytes (liver cells) and excreted in bile via the bile canaliculi. Transport proteins endogenous to hepatocytes, including but not limited to Ntcp, as well as Oatp, Oat and/or Oct isoforms mediate uptake into the hepatocytes. Such transporters move xenobiotics like therapeutic compositions as well as endogenous compounds across the sinusoidal membrane of the hepatocytes. Bile canaliculi are structures within liver tissue that receive excreted components from the hepatocytes and transport the bile to a common bile duct for removal from the animal. Biliary excretion of substrates is thus a complex process involving translocation across the sinusoidal membrane, movement through the cytoplasm, and transport across the canalicular membrane.

The advent of combinatorial chemistry techniques has enabled the identification of extremely high numbers of compounds that have potential as therapeutic agents. However, assays for susceptibility to biliary excretion that can rapidly identify those candidate compounds that have a lower potential for uptake by hepatocytes and excretion through bile canaliculi have lagged behind the pace of synthesis and screening of pharmacological activities. Numerous in vivo (e.g. bile duct cannulated animals) and in vitro preparations (e.g. isolated perfused livers, isolated hepatocytes, hepatocyte couplets, liver plasma membrane vesicles and expressed transport proteins) have been used to investigate biliary excretion processes. See e.g. Oude Elferink et al., *Biochim. Biophys. Acta* 1241:215-268,1995.

Additionally, short-term (3-8 hour) cultured hepatocyte couplets have been employed to examine directly the biliary excretion of fluorescent compounds utilizing fluorescence microscopy, as described by Graf and Boyer, *J. Hepatol.* 10:387-394, 1990. However, the application of cultured hepatocyte couplets to study biliary excretion of xenobiotics is limited in that the substrate must contain a fluorescent chromophore.

Long-term (typically more than 24 hour) cultured hepatocytes have been reported to restore polarity with canalicular-like structures. See e.g., Barth and Schwarz, *Proc. Natl. Acad. Sci.* 79:4985-4987, 1982; Maurice et al., *J. Cell Sci.* 90:79-92, 1988; Talamini et al., *Hepatology* 25:167-172, 1997. Although primary hepatocytes maintained under conventional culture conditions have been used to study drug metabolism and hepatotoxicity, long-term cultures of hepatocytes have not been a suitable model for studying hepatobiliary transport. Particularly, as described by Groothuis and Meijer, *J. Hepatology* 24(Suppl. 1):3-28, 1996 and LeCluyse et al., *Adv. Drug Del. Rev.* 22:133-186, 1996, rapid loss of liver-specific function, including hepatic transport properties, and failure to establish normal bile canalicular networks and to maintain normal hepatocyte morphology have been observed in such cultures.

Existing methods have not been demonstrated to be widely applicable to investigate human biliary excretion. In addition, existing approaches cannot be used to examine efficiently biliary excretion processes for a large number of drug candidates. Thus, there is a long-felt need for an assay to assess susceptibility of candidate compounds for hepatic uptake and biliary excretion. Such an assay would facilitate elimination of those compounds with an undesirably high susceptibility for biliary excretion from further evaluation as therapeutic agents early in the evaluation process. Correspondingly, there is a long-felt need for the rapid identification of suitable candidate compounds (e.g., compounds that are not susceptible to biliary excretion) for further testing as therapeutic agents.

SUMMARY

A method of screening a candidate compound for susceptibility to biliary excretion by a hepatocyte transport protein is disclosed herein. The method comprises providing a cell culture comprising a plurality of hepatocytes and at least one bile canaliculus, wherein at least one of the hepatocytes comprises a transport protein; exposing a candidate compound to the culture; and determining an amount of the candidate compound in the at least one bile canaliculus to thereby screen the candidate compound for susceptibility to biliary excretion by the hepatocyte transport protein. The culture of hepatocytes preferably comprises a long-term culture in a sandwich configuration.

Determining the amount of the candidate compound in the bile canaliculus preferably comprises inhibiting expression of the transport protein by introducing a nucleic acid into the hepatocytes in an amount sufficient to inhibit expression of the transport protein, and wherein the nucleic acid comprises a sequence which corresponds to a coding strand of a gene encoding the transport protein. As such, isolated short interfering RNA (siRNA) molecules, which inhibit expression of hepatocyte proteins are also provided herein.

In another embodiment, a method of screening a candidate compound for susceptibility to biliary excretion by a hepatocyte transport protein is provided, wherein first and second cell cultures are established. The first culture expresses a transport protein and the second culture is at least partially inhibited from expressing the transport protein. The method comprises exposing a candidate compound to the first culture and to the second culture for a time sufficient to allow uptake of the candidate compound; washing and lysing the first and second cultures; and determining an amount of the candidate compound present in a lysate obtained from each culture and using the amount of the candidate compound in each culture lysate to evaluate the candidate compound for susceptibility to biliary excretion by the transport protein.

In some embodiments, each of first and second cultures is separated into two fractions, with the first fraction of each of the first and second cultures having intact bile canaliculi and the second fraction of each of the first and second cultures having disrupted bile canaliculi; and comprising: (i) exposing a candidate compound to the first fraction of each of the first and second cultures and to the second fraction of each of the first and second cultures for a time (T) sufficient to allow uptake of the candidate compound; (ii) washing and lysing the first and second fractions of each of the first and second cultures; (iii) measuring an amount of candidate compound present in a lysate obtained from each fraction of each of the first and second cultures in step (ii); (iv) determining a difference in the amount of candidate compound present in the lysates from the first fraction of the first and second cultures having intact bile canaliculi and the second fraction of the first and second cultures having disrupted bile canaliculi; and (v) evaluating the candidate compound for susceptibility to biliary excretion by the transport protein using the difference determined in step (iv).

In another embodiment, a method of inhibiting expression of a protein in a hepatocyte is provided. The method comprises providing a hepatocyte expressing a protein and introducing an oligonucleotide into the hepatocyte in an amount sufficient to inhibit expression of the protein, wherein the oligonucleotide comprises a nucleotide sequence corresponding to a coding strand of a gene encoding the protein.

Accordingly, it is an object of the subject matter disclosed herein to provide a rapid method of screening of candidate compounds for susceptibility to biliary excretion.

It is a further object of the presently disclosed subject matter to provide an in vitro method of screening candidate compounds for susceptibility to biliary excretion.

It is yet a further object of the presently disclosed subject matter to provide a method of screening candidate compounds for susceptibility to biliary excretion which facilitates the screening of many candidate compounds in a single effort.

It is still a further object of the presently disclosed subject matter to provide a high throughput method of screening of candidate compounds for susceptibility to biliary excretion.

It is still yet a further object of the presently disclosed subject matter to provide a method of selectively suppressing expression of one or more specific proteins in hepatocytes to facilitate study of those proteins, including analysis of their functions and interactions with other proteins and molecules, such as for example, identifying hepatic proteins involved in uptake of drugs.

These and other objects are achieved in whole or in part by the presently disclosed subject matter. Some of the objects of the presently disclosed subject matter having been stated herein above, other objects will become evident as the description proceeds, when taken in connection with the accompanying Laboratory Examples and Drawings as best described herein below.

BREIF DESCRIPTION OF THE SEQUENCE LISTING

Figure 1A:
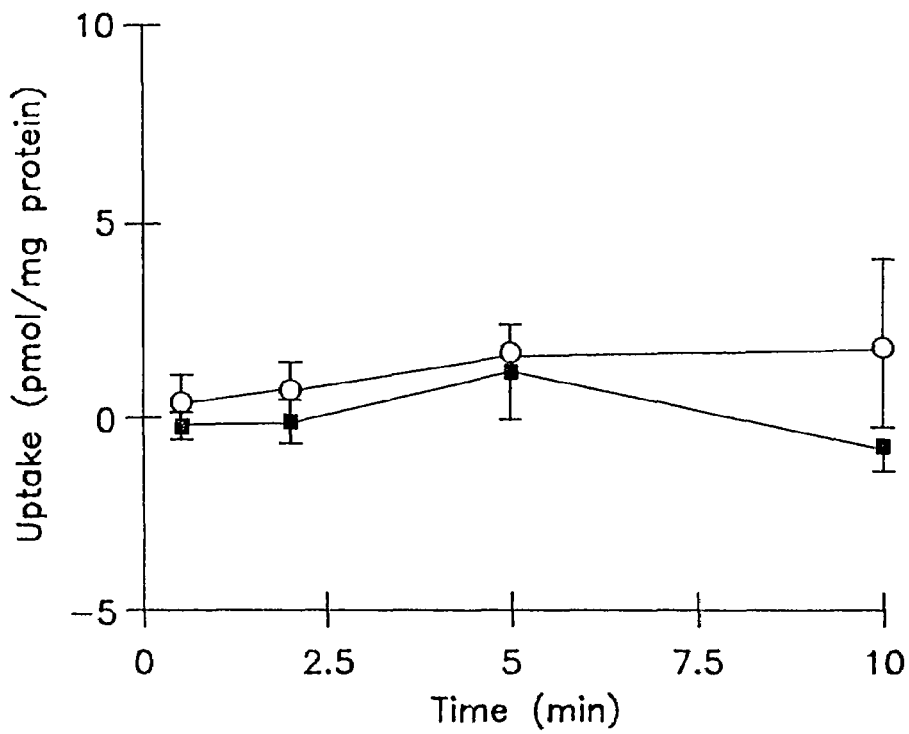
FIG. 1A is a graph depicting cumulative uptake of [$^3$H] inulin (1 μM) in standard buffer (closed symbols) and $Ca^{2+}$-free buffer (open symbols) in hepatocyte monolayers cultured for 3 hr.

SEQ ID NO: 1 is a polynucleotide sequence for rat Mrp2.
SEQ ID NO: 2 is a polynucleotide sequence for rat Mrp3.
SEQ ID NO: 3 is a polynucleotide sequence for an siRNA which corresponds to a short segment of the coding strand of rat Mrp2, referred to herein as siMRP2AB1.
SEQ ID NO: 4 is a polynucleotide sequence for an siRNA which corresponds to a short segment of the coding strand of rat Mrp2, referred to herein as siMRP2AB2.
SEQ ID NO: 5 is a polynucleotide sequence for an siRNA which corresponds to a short segment of the coding strand of rat Mrp2, referred to herein as siMRP2AB3.
SEQ ID NO: 6 is a polynucleotide sequence for an siRNA which corresponds to a short segment of the coding strand of rat Mrp3, referred to herein as siMRP3.

SEQ ID NO: 7 is a polynucleotide sequence for an siRNA which corresponds to a short segment of the coding strand of firefly (*Photinus pyralis*) luciferase (siFL).

DETAILED DESCRIPTION

In accordance with the presently disclosed subject matter, a method is provided for the screening of a candidate compound or substrate for susceptibility to biliary excretion. The method comprises the steps of providing a plurality of hepatocytes in culture, the culture comprising at least one bile canaliculus having a canalicular space and at least one of the hepatocytes comprising a transport protein; exposing a candidate compound to the culture; and determining an amount of the candidate compound in the canalicular space of the at least one bile canaliculus, the amount of the candidate compound in the canalicular space of the at least one bile canaliculus indicating the susceptibility of the candidate compound to biliary excretion by the transport protein.

As would be appreciated by one of ordinary skill in the art, in vivo biliary excretion of substrates involves translocation across the sinusoidal membrane, movement through the cytoplasm, and transport across the canalicular membrane. Thus, in a preferred hepatocyte culture of the present disclosure, functional properties displayed by hepatocytes in vivo are established. For example, the establishment of hepatic transport systems, such as sinusoidal or canalicular transport systems, or both sinusoidal and canalicular transport systems is particularly contemplated in accordance with the presently disclosed subject matter. Exemplary transport protein systems include, but are not limited to, NTCP, OATP isoforms (including but not limited to OATP1A2, OATP1B1, OATP1B3, and OATP2B1), OAT isoforms (including but not limited to OAT2 and OAT4), OCT isoforms (including but not limited to OCT1 and OCT3), BSEP, MRP isoforms (including but not limited to MRP1, MRP2 (a representative embodiment encoded by the polynucleotide of SEQ ID NO. 1), MRP3 (a representative embodiment encoded by the polynucleotide of SEQ ID NO. 2), MRP4, MRP5, MRP6, MRP7, MRP8, and MRP9), MDR isoforms (including but not limited to MDR1, MDR2, and MDR3), BCRP, ABCG5, ABCG8, FIC-1 and combinations thereof.

Generally accepted protein naming nomenclature calls for human proteins to be written in all capital letters, whereas proteins of other organisms are usually written with only the first letter of the protein name capitalized. However, for convenience, protein names disclosed herein are at times written in all capital letters when referring to both human proteins and proteins from other species. It is intended that all proteins disclosed herein are inclusive of all species regardless of the capitalization pattern, unless otherwise specified.

Additionally, the establishment of at least one bile canaliculus and the establishment of normal hepatocyte morphology in the hepatocyte cultures are also provided in accordance with the present disclosure. Preferably, the culture comprises a plurality of bile canaliculi. More preferably, the plurality of bile canaliculi comprises a canalicular network. The amount of candidate compound, as discussed in detail below, in the canalicular space of the at least one bile canaliculus indicates the susceptibility of the candidate compound to biliary excretion.

While the following terms are believed to be well understood by one of ordinary skill in the art, the following definitions are set forth to facilitate explanation of the presently disclosed subject matter.

The term "candidate compound" or "candidate substrate" is meant to refer to any compound wherein the characterization of the compound's susceptibility to biliary excretion is desirable. Exemplary candidate compounds or substrates include xenobiotics such as drugs and other therapeutic agents, carcinogens and environmental pollutants, as well as endobiotics such as steroids, fatty acids and prostaglandins.

The candidate drugs and other therapeutic agents screened in accordance with the method of the subject matter disclosed herein are contemplated to be useful in the treatment of warm-blooded vertebrates. Therefore, the subject matter disclosed herein concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

The term "biliary excretion" is meant to refer to a biological process wherein substances are removed from an animal's circulatory system by being taken up by hepatocytes (liver cells) and excreted in bile via the bile canaliculi. Uptake into the hepatocytes is mediated by transport systems endogenous to hepatocytes, including, but not limited to, NTCP, OATP isoforms (including but not limited to OATP1A2, OATP1B1, OATP1B3, and OATP2B1), OAT isoforms (including but not limited to OAT2 and OAT4), OCT isoforms (including but not limited to OCT1 and OCT3), BSEP, MRP isoforms (including but not limited to MRP1, MRP2 (a representative embodiment encoded by the polynucleotide of SEQ ID NO. 1), MRP3 (a representative embodiment encoded by the polynucleotide of SEQ ID NO. 2), MRP4, MRP5, MRP6, MRP7, MRP8, and MRP9), MDR isoforms (including but not limited to MDR1, MDR2, and MDR3), BCRP, ABCG5, ABCG8, FIC-1 and combinations thereof. Bile canaliculi are structures within liver tissue that receive excreted components from the hepatocytes and transport the bile to a bile duct for removal from the animal.

By the phrase "an amount of candidate compound" and/or the phrase "determining an amount of candidate compound in the at least one bile canaliculus", as used herein and in the claims, it is meant to refer to any amount of candidate compound that is taken up by hepatocytes and excreted into the at least one bile canaliculus in accordance with the assay of the present disclosure. For example, "an amount" can refer to substantially no candidate compound residing in the at least one bile canaliculus after exposure of a candidate compound to a culture in accordance with the present subject matter. Alternatively, "an amount" can refer to substantially all of the candidate compound residing in the at least one bile canaliculus after exposure of a candidate compound to a culture in accordance with the present subject matter. Thus, the phrase "an amount of candidate compound in the at least one bile canaliculus" can be used to describe candidate compounds that are not highly excreted, extensively excreted, and extensively and rapidly excreted.

The phrase "determining an amount of candidate compound in the at least one bile canaliculus" is also meant to refer to the use of a biliary excretion index calculation and a biliary clearance calculation as described herein below. The phrase "determining an amount of a candidate compound in the at least one bile canaliculus" may also refer to the detection of a reduced amount of a marker compound due to uptake of candidate compound into the at least one bile canaliculus as described in the high throughput embodiment of the assay of the present disclosure described herein below. Thus, quantitative and qualitative determinations of "an amount of candidate compound in the at least one bile canaliculus" are contemplated to be within the scope of the presently disclosed subject matter.

The phrase "an amount of candidate compound" and/or the phrase "determining an amount of candidate compound in the at least one bile canaliculus" are also meant to refer to the screening of, for example, a class or series of candidate compounds and then establishing a ranking of susceptibility to biliary excretion of the candidate compounds within the class or series. It is thus contemplated in accordance with a preferred embodiment of the present subject matter that the candidate compound or compounds wherein lesser or lower susceptibility to excretion is observed according to such a ranking may be chosen for further experimentation or development as a therapeutic agent, while compounds wherein higher or greater susceptibility to excretion is observed according to such a ranking may be excluded from further experimentation or development as a therapeutic agent.

However, as would be readily apparent to one of ordinary skill in the art, the characteristic that a compound is susceptible to biliary excretion does not necessarily preclude further development of the compound as a therapeutic agent. Indeed, the decision of whether to proceed with the development of a particular candidate compound as a therapeutic agent is based on many factors, including, but not limited to, the biological activity of the candidate compound. While susceptibility to biliary excretion is an important factor, it is not the only factor that is typically considered by one of ordinary skill in the art. Characterization of susceptibility to biliary excretion in accordance with the method of the present disclosure thus provides data that is desirable for use by one of ordinary skill in the art in evaluating whether to proceed with the development of a candidate compound as a therapeutic agent.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs. In one embodiment, the double stranded region is at least 15 basepairs, in another embodiment between 15 and 50 basepairs, and in yet another embodiment between 15 and 30 basepairs. In still another embodiment, the length of the double stranded region is selected from the group consisting of 19, 21, 22, 25, and 30 basepairs. In a representative embodiment, the length of the double stranded region is 19 basepairs. As describe hereinabove, the formation of the double stranded region results from the hybridization of complementary RNA strands (for example, a sense strand and an antisense strand), either via an intermolecular hybridization (i.e. involving 2 or more distinct RNA molecules) or via an intramolecular hybridization, the latter of which can occur when a single RNA molecule contains self-complementary regions that are capable of hybridizing to each other on the same RNA molecule. These self-complementary regions are typically separated by a short stretch of nucleotides (for example, about 5-10 nucleotides) such that the intramolecular hybridization event forms what is referred to in the art as a "hairpin".

As used herein, the terms "inhibit", "suppress", "down regulate", "knock down", and grammatical variants thereof are used interchangeably and refer to an activity whereby gene expression or a level of an RNA encoding one or more gene products is reduced below that observed in the absence of a nucleic acid molecule of the presently disclosed subject matter. In one embodiment, inhibition with an siRNA molecule results in a decrease in the steady state level of a target RNA. In another embodiment, inhibition with a siRNA molecule results in an expression level of a target gene that is below that level observed in the presence of an inactive or attenuated molecule that is unable to mediate an RNAi response. In another embodiment, inhibition of gene expression with an siRNA molecule of the presently disclosed subject matter is greater in the presence of the siRNA molecule than in its absence. In still another embodiment, inhibition of gene expression is associated with an enhanced rate of degradation of the mRNA encoded by the gene (for example, by RNAi mediated by an siRNA).

The terms "marker compound" and "labeled substrate" are used interchangeably and are meant to refer to a chemical compound that is readily detectable using a standard detection technique, such as fluorescence or chemiluminescence spectrophotometry, scintillation spectroscopy, chromatography, liquid chromatography/mass spectroscopy (LC/MS), colorimetry, and the like. Exemplary marker compounds thus include, but are not limited to, fluorogenic or fluorescent compounds, chemiluminescent compounds, calorimetric compounds, UV/VIS absorbing compounds, radionuclides and combinations thereof.

Therapeutic compositions that are taken up and excreted extensively though the biliary excretion processes described herein typically have a minimal chance of imparting therapeutic effects in a subject. It is thus very desirable to establish an in vitro test for a compound's susceptibility to hepatocyte uptake and biliary excretion so as to facilitate elimination of a compound with an undesirably high susceptibility from further evaluation as a therapeutic agent early in the evaluation process. The biliary excretion assay of the present disclosure provides such a test.

Rat hepatocytes are preferred in a culture for use in the methods of the presently disclosed subject matter; but, any suitable source of hepatocytes as would be apparent to one of ordinary skill in the art is contemplated to be within the scope of the present subject matter. Exemplary sources include the warm-blooded vertebrates listed above. In particular, exemplary sources include, but are not limited to, human beings, monkeys, apes, cats, dogs, pigs, hogs, cattle, oxen, sheep, horses, turkeys, chickens, ducks and geese. Further, the hepatocyte culture need not be pure, but rather may also include other cell types as desired for the particular assay. As a non-limiting example, the hepatocyte culture may further include other types of liver cells. In some embodiments, other liver cells cultured along with hepatocytes include Kupffer cells.

The biliary excretion assay method of the present subject matter may optionally comprise establishing a sandwich culture of hepatocytes wherein at least one hepatocyte layer is formed between two layers of matrix. While configuration as a sandwich culture is the preferred configuration for the culture, any suitable configuration as would be apparent to one of ordinary skill in the art is contemplated to be within the scope of the present disclosure. For example, clusters, aggregates or other associations or groupings of hepatocytes in a culture wherein at least one bile canaliculus is formed and wherein functional properties of hepatocytes are established are contemplated to fall within the scope of the present disclosure. Preferably, the culture configuration facilitates the formation of a plurality of bile canaliculi. More preferably, the culture configuration facilitates the formation of a canalicular network. The amount of candidate compound, as discussed in detail herein, in the canalicular space of the bile canaliculi indicates the susceptibility of the candidate compound to biliary excretion.

Additionally, in the preferred sandwich configuration, hepatocytes are cultured in monolayers between two layers of matrix or scaffolding. But, the hepatocytes can also be embedded in the matrix or can extend non-uniformly through the matrix vertically, horizontally, diagonally, or in any combination thereof, such that one-dimensional, two-dimensional and three-dimensional hepatocytes aggregates are formed. In accordance with the present disclosure, it is thus contemplated that the hepatocyte cultures can be formed by mixing hepatocyte cells with an appropriate matrix and inserting the mixture into a suitable culture container, such as a multi-well plate.

While collagen is a preferred substrate or scaffolding for the culture of hepatocytes, any suitable substrate or scaffolding whether natural, synthetic or combinations thereof as would be apparent to one of ordinary skill in the art is contemplated to be within the scope of the presently disclosed subject matter. For example, other biological substrates, including but not limited to laminin and the basement membrane derived biological cell culture substrate sold under the registered trademark MATRIGEL® by Collaborative Biomedical Products, Inc. of Bedford, Mass., are contemplated to comprise suitable substrate or scaffolding material. Synthetic matrix materials, substrate materials or scaffolding materials, which are typically made from a variety of materials such as polymers, are also contemplated to fall within the scope of the present subject matter. The variation of component materials with a particular matrix for use in culturing hepatocytes is also contemplated in accordance with the method of the present disclosure.

The cultured hepatocytes are preferably cultured as a "long-term culture". By "long-term culture" it is meant to refer to hepatocytes that have been cultured for at least about 12 hours. More preferably, by "long-term culture" it is meant to refer to hepatocytes that have been cultured for at least about 24 hours, for at least about 48 hours, or for at least about 72 hours. Even more preferably, by "long-term culture" it is meant to refer to hepatocytes that have been cultured for at least about 96 hours. Even more preferably, especially with cultures of human hepatocytes, it is meant to refer to hepatocytes that have been cultured for between about 168 and 240 hours (i.e. 7 to 10 days). Long-term culturing facilitates the formation of bile canaliculi and the establishment of functional properties within the hepatocytes.

The term "modulate" refers to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. A non-limiting example of an siRNA molecule of the presently disclosed subject matter is shown in SEQ ID NOS: 3, 4 and 5. In one embodiment, the siRNA comprises a double stranded polynucleotide molecule comprising complementary sense and antisense regions, wherein the antisense region comprises a sequence complementary to a region of a target nucleic acid molecule (for example, an mRNA encoding Mrp2 or Mrp3). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The term "transport protein" refers to a polypeptide which functions to convey molecules into (e.g. uptake proteins) and out of (e.g. efflux proteins) a cell (for example, a hepatocyte), as well as transportation of molecules intracellularly (e.g. translocation proteins) and other related transport activity.

Following long-standing patent law convention, the terms "a" and "an" mean "one or more" when used in this application, including the claims.

SIDE-BY-SIDE EMBODIMENT

In accordance with one embodiment of the presently disclosed subject matter, replicate hepatocyte cultures are established, preferably in sandwich configuration. A first culture is exposed to a standard buffer and a second culture is exposed to a $Ca^{2+}$-free buffer. Exposure to the $Ca^{2+}$-free buffer disrupts the bile canaliculi within the hepatocyte monolayers by breaking down adhesional processes or junctional complexes in the monolayer of hepatocytes. While exposure to the $Ca^{2+}$-free buffer is a preferred method of breaking down the adhesional processes or junctional complexes to substantially disrupt the bile canaliculi, any suitable technique for breaking down the adhesional processes or junctional complexes to promote substantial disruption of the bile canaliculi as would be apparent to one of ordinary skill in the art is contemplated to be within the scope of the present disclosure. Exemplary techniques include, but are not limited to, the administration to the culture of peptides which interact with cell-to-cell binding sites to thereby prevent neighboring cells from binding.

A candidate compound or compounds is/are then added to each culture. The candidate compound(s) cannot be retained within the bile canaliculi in the culture that was treated with $Ca^{2+}$-free buffer. Thus, in this culture, candidate compound(s) may be taken up into the hepatocytes and retained within the cytoplasm of the hepatocytes. However, any amount of the candidate compound(s) that is excreted by the hepatocytes across the canalicular membrane will flow into the buffer medium and will be removed when the buffer medium is removed. In contrast, when candidate compound(s) is/are administered to the hepatocyte sandwich culture in which the bile canaliculi are intact, any candidate compound(s) that is/are taken up by the cells and excreted by the cells is/are maintained both in the cytoplasm of the hepatocytes and in the bile canaliculi.

It is then desirable to obtain a measurement of the amount of candidate compound present within the intact bile canaliculi. The buffer media is removed from the cultures and the cultures are washed and lysed. As described in the Laboratory Examples presented herein below, the lysing of the cells within the cultures may be accomplished by addition of a suitable lysis buffer coupled with agitation of the culture. A preferred lysis buffer includes a detergent. The desired measurement is obtained by comparing the amount of candidate substance present in the lysate from the culture which has disrupted bile canaliculi (such as by exposure to $Ca^{2+}$-free medium) as compared to the lysate from the culture with intact bile canaliculi. Two particular calculations have been utilized to compare the cultures and to determine an amount of the candidate compound residing in the intact bile canaliculi. As described above, the amount of candidate compound in the intact bile canaliculi indicates the candidate compound's susceptibility to biliary excretion.

One calculation is described as a biliary excretion index, which is a calculation of the uptake and excretion of the candidate compound as follows: 100%×{(uptake in the culture with intact bile canaliculi minus uptake within hepatocytes only in the $Ca^{2+}$-free culture) divided by (uptake in the culture with intact bile canaliculi)}. The other calculation is a biliary clearance calculation, which is performed as follows: (uptake in the culture with intact bile canaliculi minus uptake within hepatocytes only in the $Ca^{2+}$-free culture) divided by (time of incubation multiplied by the concentration of the candidate compound in the buffer medium). In some embodiments, a biliary clearance value can be calculated as the ratio of the mass in the bile canaliculi and the area under the curve (AUC) in culture medium, wherein the AUC represents the integral of candidate compound (e.g. xenobiotic concentration) in the medium from time 0 to time T (time can be measure in any desired units, and is usually measured in minutes). Indeed, the term AUC can refer to the following equation:

$$AUC = \int_0^T C\,dT, \text{ where } C \text{ is concentration in medium.}$$

This equation is set forth in the *Pharmacokinetics, Second Edition* (Marcel Dekker, Inc. 1982), by Gibaldi and Perrier, (pp. 13-14).

Upon comparison of the in vitro assay of the present subject matter to a standard in vivo assay for biliary excretion as described in the Laboratory Examples presented herein below, it was determined that biliary clearance provided a more accurate and desirable evaluation of excretion. Particularly, the in vitro biliary clearance calculation adequately differentiated among candidate substances that are: (1) not highly excreted; (2) extensively excreted; and (3) extensively and rapidly excreted. Thus, the use of the biliary clearance calculation comprises an important aspect of the present disclosure.

In some embodiments, first and second cultures are established for use in a method of screening a candidate compound for susceptibility to hepatic uptake and biliary clearance or excretion. Cells in one culture are at least partially inhibited from expressing one or several hepatocyte transport protein(s). The procedure described immediately above is generally followed, and a determination as to susceptibility to biliary excretion is determined as before, except that in these embodiments the candidate compound is evaluated as to its susceptibility to hepatic uptake and biliary clearance or excretion by the inhibited hepatocyte transport protein(s).

In some embodiments, each of first and second cultures is separated into two fractions, with the first fraction of each of the first and second cultures having intact bile canaliculi and the second fraction of each of the first and second cultures having disrupted bile canaliculi; and comprising: (i) exposing a candidate compound to the first fraction of each of the first and second cultures and to the second fraction of each of the first and second cultures for a time (T) sufficient to allow uptake of the candidate compound; (ii) washing and lysing the first and second fractions of each of the first and second cultures; (iii) measuring an amount of candidate compound present in a lysate obtained from each fraction of each of the first and second cultures in step (ii); (iv) calculating the difference in the amount of candidate compound present in the lysates from the first fraction of the first and second cultures having intact bile canaliculi and the second fraction of the first and second cultures having disrupted bile canaliculi; and (v) evaluating the candidate compound for susceptibility to biliary excretion by the transport protein using the difference calculated in step (iv).

Representative transport proteins amenable to study include, but are not limited to rodent or human NTCP, OATP isoforms (including but not limited to OATP1A2, OATP1B1, OATP1B3, and OATP2B1), OAT isoforms (including but not limited to OAT2 and OAT4), OCT isoforms (including but not limited to OCT1 and OCT3), BSEP, MRP isoforms (including but not limited to MRP1, MRP2 (a representative embodiment encoded by the polynucleotide of SEQ ID NO. 1), MRP3 (a representative embodiment encoded by the polynucleotide of SEQ ID NO. 2), MRP4, MRP5, MRP6, MRP7, MRP8, and MRP9), MDR isoforms (including but not limited to MDR1, MDR2, and MDR3), BCRP, ABCG5, ABCG8, FIC-1 and combinations thereof.

In some embodiments, inhibiting expression of the hepatocyte transport protein comprises introducing an RNA into at least one of the hepatocytes in only one of the two cultures in an amount sufficient to at least partially inhibit expression of the hepatocyte transport protein of interest, for example by 10%. The RNA can comprise a ribonucleotide sequence that corresponds to a coding strand of a gene encoding the hepatocyte transport protein that is to be inhibited. This method takes advantage of the ability of short, double stranded RNA molecules to cause the down regulation of cellular genes, a process referred to as RNA interference and described herein in greater detail.

One of skill in the art will readily recognize alternative procedures for inhibiting expression of transport proteins of interest, and as such these procedures are encompassed by the methods disclosed herein as well. For example, morpholino oligonucleotides can be used to transiently inhibit expression of a protein. As used herein, a "morpholino oligonucleotide" refers to a polymeric molecule having a backbone that supports bases capable of hydrogen bonding to ribonucleic and deoxyribonucleic acid polynucleotides. In some embodiments, the polymer lacks a pentose sugar backbone moiety, and more specifically lacks a ribose or deoxyribose backbone linked by phosphodiester bonds, which is typical of nucleotides and nucleosides. Instead, the morpholino oligonucleotide contains a six-member ring containing nitrogen with coupling through the ring nitrogen.

Morpholino oligonucleotides exhibit strong resistances to nuclease degradation, hybridize to target sequences independent of salt concentration, and are highly specific to target sequences, with minimal cross-reactivity. For a review of characteristics, properties and applications of morpholino oligonucleotides, see Summerton & Weller, *Antisense Nucleic Acid Drug Dev* 7: 187-95, 1997 and Summerton, *Biochim Biophys Acta* 1489(1): 141-58, 1999, herein incorporated by reference in their entireties.

METABOLITE ASSAY EMBODIMENT

In the hepatocytes of the method of the present disclosure certain metabolic activities (called Phase I activities) may be substantially reduced. The substantial reduction in metabolic activity coupled with maintenance of biliary transport represents an advantage of the in vitro biliary excretion assay of the present disclosure in that a differentiation can be made between biliary excretion of a parent candidate compound versus a metabolite or metabolites of the parent candidate compound. This feature comprises an important aspect of the present disclosure.

In accordance with a preferred embodiment of the metabolite assay disclosed herein, the method comprises establishing a first set and second set of two cultures of hepatocytes, with each culture preferably comprising at least one layer of hepatocytes sandwiched between two layers of collagen and at least one bile canaliculus formed within at least one layer of hepatocytes. The first set of cultures includes intact bile canaliculi and the second set of cultures includes disrupted bile canaliculi.

Metabolic enzyme activity and/or transport systems are then induced in the hepatocytes of one of the cultures within each of the first set and second set of cultures in accordance with art-recognized techniques using inducers which are known to up-regulate Phase I hepatic enzyme activity, such as phenobarbital and β-naphthoflavone. Exemplary inducers and techniques associated with the same are described by Parkinson, A. (1996) *Biotransformation of Xenobiotics in Casarett and Doull's Toxicology. The Basic Science of Poisons.*, 5$^{th}$ Ed. (Klaassen, C. D. ed.) pp.113-186, McGraw Hill, New York, and by LeCluyse et al., (1996) *Cultured rat hepatocytes*, in *Models for Assessing Drug Absorption and Metabolism* (Borchardt et al. eds), pp 121-160, Plenum Press, New York, the contents of each of which are herein incorporated by reference.

A candidate parent compound is exposed to the first and second sets of cultures for a time sufficient to allow uptake of the candidate parent compound. Each set of cultures is washed and then lysed. The amount of candidate parent compound present in the lysate obtained from the culture in each set of cultures having inactive metabolic enzymes is determined. The amount of metabolite of the candidate parent compound present in the lysate obtained from the culture in each set of cultures having active metabolic enzymes is also determined.

A biliary clearance value for the cultures having inactive metabolic enzymes is calculated using the amount of candidate parent compound in the culture lysate. The calculated biliary clearance value is then used to determine the susceptibility of the candidate parent compound to biliary excretion, as described above. A biliary clearance value for the cultures having active metabolic enzymes is calculated using the amount of metabolite of the candidate parent compound in the culture lysate. The calculated biliary clearance value is then used to determine the susceptibility of the metabolite to biliary excretion, as described above.

HIGH THROUGHPUT ASSAY EMBODIMENT

In some embodiments the presently disclosed subject matter pertains to a high throughput hepatic uptake and biliary excretion assay. Such an assay preferably involves the use of cultured hepatocytes as described above, in conjunction with a marker compound that is a substrate for endogenous sinusoidal or canalicular transport systems, both sinusoidal and canalicular transport systems, or metabolic protein systems. Exemplary transport systems include, but are not limited to human or rodent NTCP, OATP isoforms (including but not limited to OATP1A2, OATP1B1, OATP1B3, and OATP2B1), OAT isoforms (including but not limited to OAT2 and OAT4), OCT isoforms (including but not limited to OCT1 and OCT3), BSEP, MRP isoforms (including but not limited to MRP1, MRP2 (a representative embodiment encoded by the polynucleotide of SEQ ID NO. 1), MRP3 (a representative embodiment encoded by the polynucleotide of SEQ ID NO. 2), MRP4, MRP5, MRP6, MRP7, MRP8, and MRP9), MDR isoforms (including but not limited to MDR1, MDR2, and MDR3), BCRP, ABCG5, ABCG8, FIC-1 and combinations thereof. Particularly, a candidate compound is administered to a hepatocyte culture in conjunction with a marker compound in accordance with the cell culture and compound administration techniques described in the Laboratory Examples presented below.

Uptake and excretion competition between a candidate compound and the marker compound is then evaluated. That is, a significant drop in the amount of marker compound (e.g. measured or detected signal from the marker compound)

within bile canaliculi in a culture may indicate that the candidate compound (as opposed to the marker compound) is taken up and excreted extensively.

A ranking of susceptibility to hepatic uptake and biliary excretion of the candidate compounds is then established. It is thus contemplated in accordance with a preferred embodiment of the high throughput assay of the presently disclosed subject matter that the candidate compound or compounds wherein lesser or lower susceptibility to hepatic uptake and/or biliary excretion is observed according to such a ranking may be chosen for further experimentation or development as a therapeutic agent, while compounds wherein higher or greater susceptibility to excretion is observed according to such a ranking may be excluded from further experimentation or development as a therapeutic agent.

An exemplary marker compound comprises the fluorescent MRP2 substrate, carboxydichlorofluorescein. Preferably, carboxydichlorofluorescein diacetate, which exhibits only a weak fluorescence, is utilized as a fluorogenic precursor due to its rapid penetration into the hepatocyte plasma membrane. Carboxydichlorofluorescein diacetate is hydrolyzed readily in the cytoplasm of hepatocytes by intracellular esterases to a highly fluorescent product, carboxydichlorofluorescein as described in Haugland, *Molecular Probes: Handbook of Fluorescent Probes and Research Chemicals* (1992-1994), p.134, Molecular Probes, Inc., 1992.

The fluorescence of carboxydichlorofluorescein is sensitive to pH and thus any assay based on the intensity of carboxydichlorofluorescein fluorescence should consider the effects of pH. However, it has been observed that less than a 0.3 pH unit difference has been found between cytosol and bile canaliculi in hepatocyte couplets. Although carboxydichlorofluorescein has been used for pH determinations in acidic organelles, its fluorescence intensity is not altered markedly between pH 7.1 and pH 7.4. The fluorescence of carboxydichlorofluorescein at pH 7.4 is only about 10-20% higher than at pH 7.1 at maximum emission wavelength. Inasmuch as the fluorescence of carboxydichlorofluorescein is used as a qualitative probe to localize carboxydichlorofluorescein cellular distribution, the slight pH gradient between cytosol and the canaliculi do not affect the application of the high throughput assay of the present subject matter disclosed herein.

Additional marker compounds include, but are not limited to, fluorescein-labeled taurocholate, a bile acid that is rapidly and extensively taken up by hepatocytes and excreted into the bile canaliculi as described in the Laboratory Examples presented herein below; cholylglycylamido fluorescein, another fluorescent bile acid described by Boyer and Soroka, *Gastroenterology* 109:1600-1611 (1995); rhodamine 123; P-gp; and carboxyfluorescein diacetate (CFDA).

It is contemplated that the method disclosed herein may be performed within standard multi-well assay plates as are well known in the art, such as the 96-well or 384-well micro-titer plates that are available from ICN Pharmaceuticals, Inc. (Costa Mesa, Calif.). Thus, a plurality of candidate compounds can be simultaneously screened for susceptibility to hepatic uptake and/or biliary excretion within multiple wells of a multi-well plate.

In some embodiments, the above-described method is modified such that competition between the candidate compound and the marker compound, or labeled substrate, is for uptake and excretion by a particular transport protein rather than more generally to all biliary transport and excretion systems. In some embodiments, the competition occurs after at least one hepatocyte transport protein is at least partially inhibited. The labeled substrate is chosen as one that is known to be susceptible to transport by the transport protein. The presence of a reduced amount of the labeled substrate in the bile canaliculus indicates the susceptibility of the candidate compound to biliary excretion by the transport protein.

In some embodiments, inhibiting of the transport protein is provided by inhibiting expression of the transport protein. The inhibiting expression of the transport protein can comprise introducing an RNA into at least one of the hepatocytes in only one of the two cultures in an amount sufficient to at least partially inhibit expression of the hepatocyte transport protein of interest, for example by 10%. The RNA can comprise a ribonucleotide sequence corresponding to a coding strand of a gene encoding the hepatocyte transport protein that is to be inhibited. This method takes advantage of the ability of short, double stranded RNA molecules to cause the down regulation of cellular genes, a process referred to as RNA interference and described herein in greater detail.

In other embodiments, alternative techniques for inhibiting expression of a particular protein are used. For example, a morpholino oligonucleotide can be administered to a cell expressing a protein of interest, wherein the morpholino oligonucleotide has binding specificity for the protein of interest. Binding of the morpholino polynucleotide to a nucleic acid (for example, an mRNA) encoding the protein of interest results in inhibition of expression of the protein.

Inhibition of Hepatocyte Transport Protein Expression Using RNA Interference

The presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See generally Fire et al., *Nature* 391:806-811, 1998. The process of post-transcriptional gene silencing is thought to be an evolutionarily conserved cellular defense mechanism that has evolved to prevent the expression of foreign genes (Fire, *Trends Genet* 15:358-363, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., *Nature* 409:363-366, 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., *Genes Dev* 15:188-200, 2001b).

RNAi has been described in several cell type and organisms. Fire et al., 1998 described RNAi in C. elegans. Wianny & Zernicka-Goetz, *Nature Cell Biol* 2:70-75, 1999 disclose RNAi mediated by dsRNA in mouse embryos. Hammond et al., *Nature* 404:293-296, 2000 were able to induce RNAi in *Drosophila* cells by transfecting dsRNA into these cells. Elbashir et al. *Nature* 411:494-498, 2001a demonstrated the presence of RNAi in cultured mammalian cells including human embryonic kidney and HeLa cells by the introduction of duplexes of synthetic 21 nucleotide RNAs.

Other studies have indicated that a 5'-phosphate on the target-complementary strand of a siRNA duplex facilitate siRNA activity and that ATP is utilized to maintain the 5'-phosphate moiety on the siRNA (Nykanen et al., *Cell* 107: 309-321, 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359, 180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

In some embodiments, the presently disclosed subject matter utilizes RNAi to at least partially inhibit expression of one or more hepatocyte proteins of interest. Inhibition is preferably at least about 10% of normal expression amounts. In some embodiments, the method comprises introducing an RNA into at least one of the plurality of hepatocytes in an amount sufficient to inhibit expression of the hepatocyte transport protein, wherein the RNA comprises a ribonucleotide sequence which corresponds to a coding strand of a gene encoding the hepatocyte transport protein. In some embodiments, the hepatocytes are present in an organism, preferably a mammal, and the RNA is introduced into the organism. As a non-limiting example, the gene can encode a human or rodent NTCP, OATP isoform (including but not limited to OATP1A2, OATP1B1, OATP1B3, and OATP2B1), OAT isoform (including but not limited to OAT2 and OAT4), OCT isoform (including but not limited to OCT1 and OCT3), BSEP, MRP isoform (including but not limited to MRP1, MRP2 (a representative embodiment encoded by the polynucleotide of SEQ ID NO. 1), MRP3 (a representative embodiment encoded by the polynucleotide of SEQ ID NO. 2), MRP4, MRP5, MRP6, MRP7, MRP8, and MRP9), MDR isoform (including but not limited to MDR1, MDR2, and MDR3), BCRP, ABCG5, ABCG8, FIC-1 and combinations thereof.

The RNA can have a double-stranded region comprising a first strand comprising a ribonucleotide sequence that corresponds to the coding strand of the gene encoding the hepatocyte transport protein and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases. Exemplary RNAs include those having a nucleotide sequence of one of SEQ ID NOs: 3, 4 and 5.

One skilled in the art will recognize that any number of suitable common techniques can be used to introduce the RNAs into a hepatocyte. In some embodiments, a vector encoding the RNA is introduced into at least one of the plurality of hepatocytes. For example, the vector encoding the RNA can be transfected into the hepatocytes and the RNA is then transcribed by cellular polymerases.

In some embodiments, a recombinant virus comprising nucleic acid encoding the RNA can be produced. Introducing the RNA into a hepatocyte then comprises infecting the hepatocyte with the recombinant adenovirus. Hepatocyte polymerases transcribe the RNA resulting in expression of the RNA within the hepatocyte. Engineering recombinant viruses is well known to those having ordinary skill in the art. One of skill would readily appreciate the multiple factors involved in selecting the appropriate virus and vector components needed to optimize recombinant virus production for use with the presently disclosed subject matter without the necessity of further detailed discussion herein. As one non-limiting example, a recombinant adenovirus can be engineered comprising DNA encoding an siRNA. The virus can be engineered to be replication deficient such that hepatocytes can be infected by the recombinant adenovirus, the siRNA transcribed, and transiently expressed in the infected hepatocyte. Details of recombinant virus production and use can be found in U.S. patent application Ser. No. 10/195,034 and PCT Patent Application Ser. No. US02/22010, herein incorporated by reference in their entireties. Alternatively, a commercial kit for producing recombinant viruses can be used, such as for example, the pSILENCER ADENO 1.0-CMV SYSTEM™ (Ambion, Austin, Tex., USA).

The presently disclosed subject matter further comprises an isolated siRNA molecule, which inhibits expression of a specific hepatocyte transport protein. In an exemplary embodiment, the hepatocyte transport protein is a human or rodent NTCP, OATP isoform (including but not limited to OATP1A2, OATP1 B1, OATP1 B3, and OATP2B1), OAT isoform (including but not limited to OAT2 and OAT4), OCT isoform (including but not limited to OCT1 and OCT3), BSEP, MRP isoform (including but not limited to MRP1, MRP2 (a representative embodiment encoded by the polynucleotide of SEQ ID NO. 1), MRP3 (a representative embodiment encoded by the polynucleotide of SEQ ID NO. 2), MRP4, MRP5, MRP6, MRP7, MRP8, and MRP9), MDR isoform (including but not limited to MDR1, MDR2, and MDR3), BCRP, ABCG5, ABCG8, FIC-1 and combinations thereof.

The siRNA molecule can comprise a sense region and an antisense region, wherein the antisense region comprises a nucleic acid sequence complementary to an RNA sequence encoding the hepatocyte transport protein and the sense region comprises a nucleic acid sequence complementary to the antisense region. The siRNA molecule is assembled from the sense region and the antisense region of the siRNA molecule. In a representative embodiment, the sense region comprises a contiguous 19-30 nucleotide subsequence of one of SEQ ID NOs. 3, 4 and 5 and the antisense region comprises the reverse-complement of the sense region. The sense region and the antisense region can further comprise a 3'-terminal overhang, which is preferably 2 to 8 nucleotides in length. The 3'-terminal nucleotide overhang can further contain one or more chemically modified nucleotides.

In some embodiments, the sense region and the antisense region are covalently connected via a linker molecule. In some embodiments, the linker molecule is a polynucleotide linker, for example, a polynucleotide linker of from 5 to 9 nucleotides. In some embodiments, the linker molecule is a non-nucleotide linker. A carrier comprising an siRNA is also provided. Representative carriers include, for example, water, saline, dextrose, glycerol, ethanol or the like, and combinations thereof. The carrier can further include auxiliary substances such as wetting or emulsifying agents, pH buffering agents and the like.

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

LABORATORY EXAMPLES

The following Laboratory Examples pertain to the establishment of a correlation of biliary excretion in sandwich-cultured rat hepatocytes (present method) and in vivo in rats (standard). Five model substrates representing a diverse spectrum of biliary excretion properties were selected to examine the relationship between the percentage of the dose excreted in bile in vivo in rats and in vitro using sandwich-cultured hepatocytes in accordance with the methods disclosed herein. The five model substrates included inulin, salicylate, methotrexate, [D-pen$^{2,5}$]enkephalin and taurocholate.

Additionally, a comparison of in vivo and in vitro biliary excretion of 264W94 and its metabolites is set forth in Example 4. Compound 2169W94 is the 0-demethylated metabolite of 264W94 in rats and humans, which can undergo further conjugation with urindine-5'-diphosphoflucuronic acid to form a glucuronide conjugate (Silver et al., *ISSX Proceedings*, (San Diego, Calif. USA) pp. 387, 1996). The structural formulas of compounds 264W94 and 2169W94 are presented in FIG. 9. Finally, the use of siRNA for the modulation of MRP2 and MRP3 expression in sandwich-cultured rat hepatocytes (SCRH) is disclosed.

Materials and Methods Used in Examples 1-4

Chemicals.

[$^3$H]Taurocholate (3.4 Ci/mmol; purity>97%), [$^{14}$C]salicylate (55.5 mCi/mmol; purity>99%), and [$^3$H][D-pen$^{2,5}$] enkephalin (36 Ci/mmol; purity>97%0 were obtained from Dupont New England Nuclear (Boston, Mass.). [$^3$H]Methotrexate (13.7 Ci/mmol; purity>99%) and [$^3$H]inulin (1.3 Ci/mmol; purity 97%) were obtained from Amersham International plc (Buckinghamshire, England). Compounds [$^{14}$C] 264W94 ((3R, 5R)-3-butyl-3-ethyl-2,3,4,5-tetrahydro-7, 8-dimethoxy-5-phenyl-1, 4-benzothiazepine-1, 1-dioxide; 45.5 mCi/mmol; purity>99%) and [$^{14}$C]2169W94 ((3R, 5R)-3-ethyl-2,3,4,5-tetrahydro-7-methoxy-8-hydroxy-5-phenyl-1,4-benzothiazepine-1,1-dioxide; 43.7 mCi/mmol; purity>99%) were obtained from Glaxo Wellcome, Inc. (Research Triangle Park, N.C.). Collagenase (type 1, class 1) was obtained from Worthington Biochemical Corp. (Freehold, N.J.). Dulbecco's modified Eagles' medium (DMEM), fetal bovine serum and insulin were purchased from Gibco (Grand Island, N.Y.). Rat-tail collagen (type 1) was obtained from Collaborative Biomedical Research (Bedford, Mass.). All other chemicals and reagents were of analytical grade and were readily available from commercial sources.

Animals.

Male Wistar rats (250-280 g) from Charles River Laboratory (Raleigh, N.C.) were used as liver donors. Rats were housed individually in stainless-steel cages in a constant alternating 12-hr light and dark cycle at least 1 week before the study was performed, and were fed ad libitum until use. Bile duct cannulated rats (200-250 g) were obtained from Charles River (Raleigh, N.C.). The Institutional Animal Care and Use Committee at the University of North Carolina at Chapel Hill, Chapel Hill, N.C., approved all procedures.

Preparation of Culture Dishes.

Plastic culture dishes (60 mm) were precoated with rat-tail collagen at least 1 day prior to preparing the hepatocyte cultures. To obtain a gelled collagen substratum, ice-cold neutralized collagen solution (0.1 ml, 1.5 mg/ml, pH 7.4) was spread onto each culture dish. Freshly coated dishes were placed at 37° C. in a humidified incubator for approximately 1 hr to allow the matrix material to gel, followed by addition of 3 ml DMEM to each dish and storage in a humidified incubator.

Culture of Rat Hepatocytes.

Hepatocytes were isolated with a two-step perfusion method. Briefly, rats were anesthetized with ketamine and xylazine (60 and 12mg/kg i.p., respectively) prior to portal vein cannulation. The liver was perfused in situ with oxygenated Ca$^{2+}$-free Krebs-Henseleit bicarbonate buffer containing collagenase type 1 (0.5 mg/ml) for 10 min. The hepatic capsule was removed with forceps. The hepatocytes were released by shaking the liver gently in 100 ml DMEM.

The released cells were filtered through a sterile nylon mesh (70-μm). The hepatocyte suspensions were centrifuged at 50 xg for 3 min. The cell pellet was resuspended in 25 ml DMEM and an equal volume of 90% isotonic polyvinylpyrrolidone-coated silica colloid centrifugation medium (pH 7.4) sold under the registered trademark PERCOLL® by Pharmacia, Inc. of Piscataway, N.J. The resulting cell suspension was centrifuged at about 70 to about 150 xg for 5 min. The pellet was resuspended in 50 ml DMEM and the cell suspensions were combined into one tube followed by centrifugation at 50 xg for 3 min. Hepatocyte viability was determined by trypan blue exclusion. Only those hepatocyte preparations with viability greater than 90% were utilized for further studies.

Hepatocyte suspensions were prepared with DMEM containing 5% fetal calf serum, 1 μM dexamethasone and 4 mg/L insulin. Hepatocyte suspensions were added to the precoated dishes at a density of about 2-3×10$^6$ cells/60-mm dish.

Approximately 1 hr after plating the cells, the medium was aspirated and 3-ml fresh DMEM was added. For transport studies, hepatocytes that had been seeded for 3-5 hr without collagen overlay were defined as 3-hr or short-term cultured hepatocytes.

To prepare sandwich-cultured hepatocytes, neutralized collagen solution (0.1 ml, about 1.5 to about 3.0 mg/ml, pH 7.4) was added to the monolayers 24 hr after the cells were seeded. Cultures with collagen overlay were incubated for 45 min at 37° C. in a humidified incubator to allow the collagen to gel before addition of DMEM. Medium was changed on a daily basis until the fourth day after the cells were seeded. These hepatocytes were referred to as 96-hr or long-term cultured hepatocytes.

Cumulative Uptake Studies in Sandwich-Cultured Hepatocytes.

Hepatocytes cultured in a collagen-sandwich configuration were incubated in 3 ml standard buffer or $Ca^{2+}$-free buffer at 37° C. for 10 min. After removing the incubation buffer, uptake was initiated by addition of 3 ml standard buffer containing substrate to each dish. After incubation for designated times, cumulative uptake was terminated by aspirating the incubation solution and rinsing 4 times with 3 ml ice-cold standard buffer to remove extracellular substrate. After washing, 2 ml of 1% Triton X-100 solution was added to culture dishes, and the cells were lysed by shaking the dish on a shaker for 20 min at room temperature. An aliquot (1 ml) of lysate was analyzed by liquid scintillation spectrometry. Bio-Rad DC Protein Assay Kit (Bio-Rad Laboratories, Hercules, Calif.) was used to determine the protein concentration in the culture extracts using bovine serum albumin as standard. Triton X-100 (1%) did not interfere with the assay. All values for substrate uptake into cell monolayers were corrected for nonspecific binding to the collagen by subtracting the substrate uptake determined in the appropriate control dishes in the absence of cells as described previously.

Biliary Excretion in Rats after Intravenous Administration of 264W94 and Oral Administration of 2169W94.

[$^{14}$C]264W94 was formulated as a solution in a mixture of sterile water/polypropylene glycol 400/ethanol (2:1:1 v/v/v) at a concentration of 0.125 mg/mL. Following collection of pre-dose bile, [$^{14}$C]264W94 solution was administered by caudal vein injection (0.1 mg/kg). For the 2169W94 studies, [$^{14}$C]2169W94 was prepared as a suspension at a concentration of 0.1 mg/mL in 0.5% (w/v) methylcellulose in water. Following collection of pre-dose bile, [$^{14}$C]2169W94 suspension was administrated by gavage (1.0 mg/kg). All rats were placed onto individual plastic metabolism cages that allowed the rats unrestrained movement. Bile was collected into polypropylene containers surrounded by ice. For the 264W94 studies, the bile container was changed at 8 and 24 hours after the dose. Previous studies indicated that samples were stable on ice for 24 hours. Bile samples were stored at −20° C. until analysis.

Analytical Procedure.

Aliquots of cell lysate or bile samples containing 264W94 or 2169W94 were mixed with 2-fold volumes of ice-chilled acetonitrile, and centrifuged to remove precipitated proteins. The supernatant was evaporated under nitrogen at room temperature, and reconstituted in 100 µL of a 70/30 mixture of 50 mM ammonium acetate/acetonitrile/trifluoroacetic acid (95: 5:0.1 v:v:v) and acetonitrile. The sample extracts were injected onto a WATERS™ SYMMETRY™ C18 column (3.9×150 mm) and eluted by a 85/15 mixture of 50 mM ammonium acetate (pH 4.0) and acetonitrile; the percentage of acetonitrile was increased by a WATERS™ 600E System Controller to 55% over a period of 20 minutes, and then to 100% during the next 10 minutes.

Radiocarbon that eluted from the HPLC was quantified with an on-line radioactivity detector (RADIOMATIC FLO-ONE/BETA™ Radio-Chromatography Detector Series 500 TR Series, Packard Instrument Co.). The peaks of 264W94, 2169W94, and 2169W94 glucuronide were identified by comparing with purified standard compound. Under these conditions, baseline separation of these three components was achieved. The concentration of the three components was determined by normalizing the eluted radioactivity in each peak to the total injected radioactivity.

Data Analysis.

Uptake data were normalized to the protein content and expressed as mean±SD from 3-4 separate preparations of hepatocytes. Statistical differences between mean values for the 10-min cumulative substrate uptake in the presence and absence of $Ca^{2+}$ were determined by the use of the well-known Student's t-test. A P value of <0.05 was considered significant.

In vivo biliary clearance, $Cl_B$ (ml/min/kg body weight), was calculated according to Equation 1:

$$Cl_B = \frac{Amount_{bile(0-T)}}{AUC_{0-T}} \quad \text{Equation 1}$$

where $Amount_{bile(O-T)}$ represents the amount of parent drug recovered in bile from 0 to time T when most drug was eliminated from the systemic circulation, and $AUC_{O-T}$ represents the area under the plasma concentration-time curve from 0 to time T (in minutes).

The in vivo intrinsic biliary clearance ($Cl_{Bin}$, ml/min/kg body weight) was estimated according to Equation 2 based on the well-stirred model of hepatic disposition assuming biliary excretion is the predominant elimination pathway (Pang et al., *J. Pharmacokinet. Biopharm.* 5:625-653, 1977).

$$Cl_{Bin} = \frac{Q \cdot Cl_B}{Q - Cl_B} \quad \text{Equation 2}$$

where Q represents rat hepatic plasma/blood flow, 40-70 ml/min/kg of body weight {(blood flow×(1-hematocrit)}; Pollack et al., *J. Pharmacol. Exp. Ther.* 18:197-202, (1989), and $Cl_B$ represents biliary clearance for model compounds reported in the literature or calculated from Equation 1.

Biliary excretion of substrates in the monolayers was quantitatively assessed by the Biliary Excretion Index based on Equation 3:

$$BiliaryExcretionIndex = \\ \frac{Uptake_{standard} - Uptake_{ca++-free}}{Uptake_{standard}} \cdot 100\% \quad \text{Equation 3}$$

where $Uptake_{standard}$ and $Uptake_{Ca^{2+}-free}$ represent the cumulative uptake of substrate over a 10-min interval in the hepatocyte monolayers pre-incubated in standard buffer and in $Ca^{2+}$-free buffer, respectively.

Biliary clearance in the sandwich-cultured hepatocytes, $Cl_{B(culture)}$ (ml/min/kg per body weight), was calculated according to Equation 4:

$$Cl_{B(culture)} = \frac{Uptake_{standard} - Uptake_{ca++-free}}{Time_{incubation} \cdot Concentration_{medium}} \quad \text{Equation 4}$$

where $Time_{incubation}$ was 10 min and $Concentration_{medium}$ represented the initial substrate concentration in the incubation medium. In some embodiments, a biliary clearance value can be calculated as the ratio of the mass in the bile canaliculi and the area under the curve (AUC) in culture medium, wherein the AUC represents the integral of candidate compound (e.g. xenobiotic concentration) in the medium from time 0 to time T (time can be measure in any desired units, and is usually measured in minutes). Indeed, the term AUC can refer to the following equation:

$$AUC = \int_0^T C \, dT, \text{ where } C \text{ is concentration in medium.}$$

This equation is set forth in the *Pharmacokinetics, Second Edition* (Marcel Dekker, Inc. 1982), by Gibaldi and Perrier, (pp. 13-14). Rat liver weight and protein content in liver tissue were assumed to be 40 g/kg of body weight and 0.20 g/g of liver weight (Seglen et al., *Methods in Cell Biology* (13$^{th}$ Ed., Prescott D. M. Eds.) pp. 30-78, Academic Press, New York, 1976), respectively, in all calculations.

SUMMARY OF THE RESULTS OF THE EXAMPLES

Biliary excretion of the five model substrates in long-term sandwich-cultured hepatocytes in accordance with the present subject matter was consistent with their in vivo biliary excretion properties. Quantification of biliary excretion in the cultured hepatocytes utilizing the biliary excretion index calculation is described herein above. Briefly, the biliary excretion index represents the percentage of retained substrate in the bile canaliculi. The results of the Laboratory Examples indicate that compounds undergoing negligible biliary excretion in vivo based on the percentage of dose excreted in bile (e.g., inulin, salicylate) have a low biliary excretion index (approximately zero). Compounds that are more extensively excreted in bile in vivo (e.g., methotrexate, [D-pen$^{2,5}$]enkephalin, and taurocholate) have a high biliary excretion index (approximately 50%).

The relationship between the biliary excretion index and the percentage of the dose excreted in bile in vivo only reveals a categorical correlation. Methotrexate and [D-pen$^{2,5}$]enkephalin represent compounds that are "highly" excreted in bile (approximately 60% and 70% of the i.v. dose was recovered in bile in 1 hr, respectively). In contrast, taurocholate is "rapidly and extensively" excreted in that almost all of the i.v. dose was excreted in bile in less than 1 hr. The biliary excretion index can thus differentiate between compounds that undergo extensive versus negligible or low biliary excretion.

However, the biliary excretion index appears unable to differentiate between compounds that are highly excreted in bile, like methotrexate (biliary excretion index: approximately 55%) or [D-pen$^{2,5}$]enkephalin (biliary excretion index: approximately 42%), and compounds that are "rapidly and extensively" excreted in bile, like taurocholate (biliary excretion index: approximately 56%). This limitation in the biliary excretion index may be due to the fact that this index is determined predominantly by the canalicular excretory functions. The percentage of i.v.-administered substrate excreted into the bile in vivo is determined by sinusoidal uptake activity, canalicular excretory activity, as well as other competitive elimination processes.

Biliary clearance represents a more effective parameter for comparison of the relationship between in vivo and in vitro biliary excretion. The in vivo biliary clearance was calculated in the Laboratory Examples as the ratio of the amount excreted into bile at time T and the plasma AUC between time 0 and time T. Because most of the administered dose was eliminated at time T, the biliary clearance approximates the biliary clearance calculated from time 0 to time infinity. Biliary clearance calculated in this matter is a function of intrinsic biliary clearance and the hepatic plasma/blood flow rate. To eliminate the effects of plasma flow, the intrinsic biliary clearance was calculated based on the "well stirred" model of hepatic disposition described by Pang and Rollan in *J. Pharmacokinet. Biopharm.* 5:625-653, 1977. Likewise, in vitro biliary clearance was calculated as the ratio of the amount excreted in the canalicular networks in the hepatocyte monolayers and the AUC in the incubation medium. Thus, in some embodiments, a biliary clearance value can be calculated as the ratio of the mass in the bile canaliculi and the area under the curve (AUC) in culture medium, wherein the AUC represents the integral of candidate compound (e.g. xenobiotic concentration) in the medium from time 0 to time T (time can be measure in any desired units, and is usually measured in minutes). Indeed, the term AUC can refer to the following equation:

$$AUC = \int_0^T C \, dT, \text{ where } C \text{ is concentration in medium.}$$

This equation is set forth in the *Pharmacokinetics, Second Edition* (Marcel Dekker, Inc. 1982), by Gibaldi and Perrier, (pp. 13-14).

In the sandwich-cultured hepatocytes, the incubation medium was accessible to all hepatocytes in the dish at the same time. Thus, the calculated in vitro biliary clearance should represent the intrinsic biliary clearance. However, since biliary excretion involves two processes, uptake across the sinusoidal membrane and excretion across the canalicular membrane, the true intrinsic biliary clearance should be determined by transport across the canalicular membrane and calculated based on intracellular substrate concentrations. Therefore, the in vivo and in vitro "intrinsic" clearance values calculated in the Laboratory Examples may be referred to as an "apparent" intrinsic biliary clearance value, which would be rate-limited by the slowest step in the process, either sinusoidal uptake or canalicular excretion.

The correlation between in vitro biliary clearance and in vivo intrinsic biliary clearance was high ($r^2=0.9865$) for the five model substrates. According to the in vivo intrinsic biliary clearance, the five model substrates can be classified into three groups: compounds that are not excreted in bile (inulin and salicylate; approximately 0 ml/min/kg), compounds that are highly excreted in bile (methotrexate and [D-pen$^{2,5}$]enkephalin, approximately 17.3 ml/min/kg and approximately 34.4 ml/min/kg, respectively); and compounds that are rapidly and extensively excreted in bile (taurocholate, approximately 116.9 ml/min/kg). The estimated in vitro biliary clearance adequately differentiated between these three groups of compounds (approximately 0, 4-13, and 56 ml/min/kg, respectively). These results suggest that the biliary clearance more accurately characterizes the relationship between in vivo and in vitro biliary excretion as compared to the biliary excretion index.

Example 5 describes siRNA utilization to modulate drug transporter function in primary hepatocytes. Treatment of SCRH with Mrp2 siRNA (siMrp2) essentially produced a transient Mrp2-deficient model: the suppression of canalicular Mrp2 expression profoundly reduced the biliary excretion of carboxydichlorofluorescein (CDF). However, CDF was excreted efficiently from these cells due to the maintenance of high expression levels of Mrp3. With siMrp3-treated SCRH, a transient Mrp3-deficient model was established, which is currently not available in vivo. Knockdown of Mrp3 resulted in a redirection of the route of CDF excretion into bile, hence canalicular fluorescence in siMrp3-treated SCRH was higher than in control cells. Overall, modulation of drug transporters by siRNA treatment in SCRH provides for the study of regulation and function of drug transport proteins to elucidate the complementary roles of drug transporters in determining hepatobiliary drug disposition, and to define the effect of specific interactions with drug transporters, especially when specific inhibitors are not available.

EXAMPLE 1

Cumulative Uptake in Cultured Hepatocytes

Figure 1B:
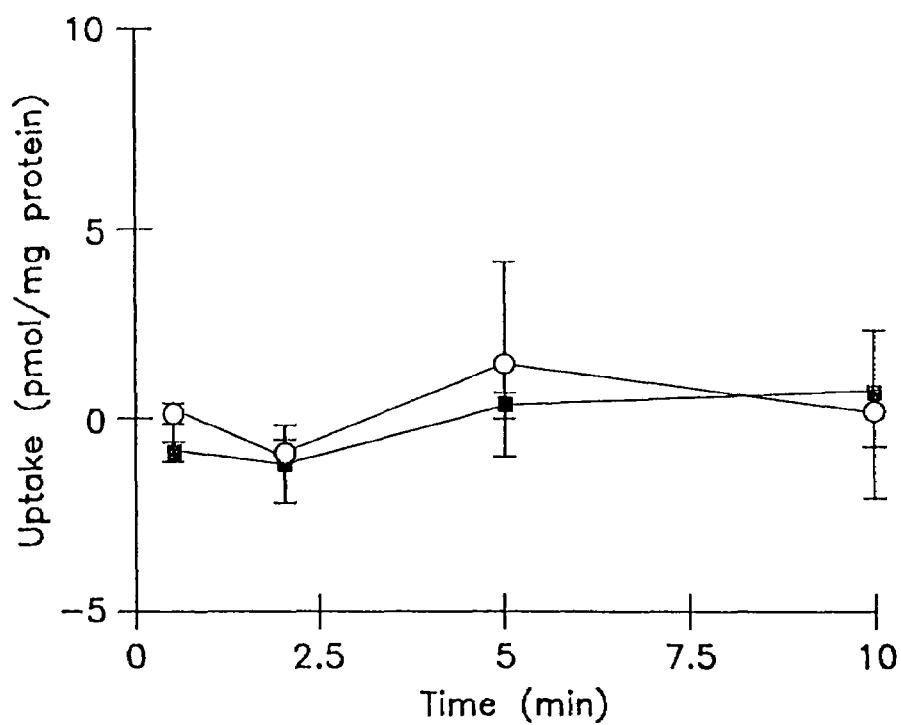
FIG. 1B is a graph depicting cumulative uptake of [$^3$H] inulin (1 μM) in standard buffer (closed symbols) and $Ca^{2+}$-free buffer (open symbols) in hepatocytes cultured in a sandwich configuration for 96 hr.
Figure 2A:
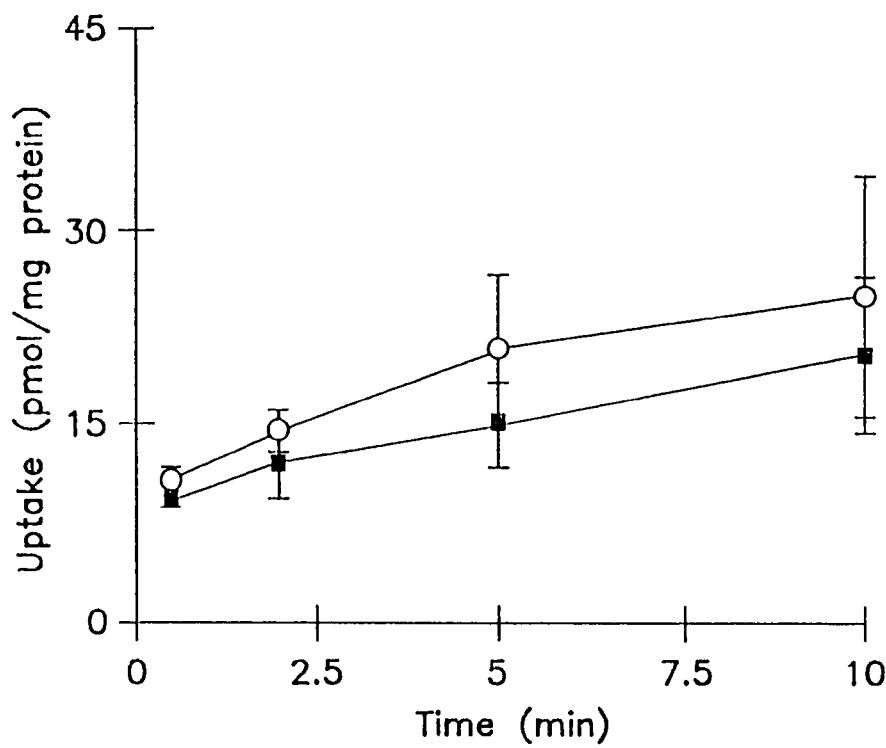
FIG. 2A is a graph depicting cumulative uptake of [$^{14}$C] salicylate (1 μM) in standard buffer (closed symbols) and $Ca^{2+}$-free buffer (open symbols) in hepatocyte monolayers cultured for 3 hr.
Figure 2B:
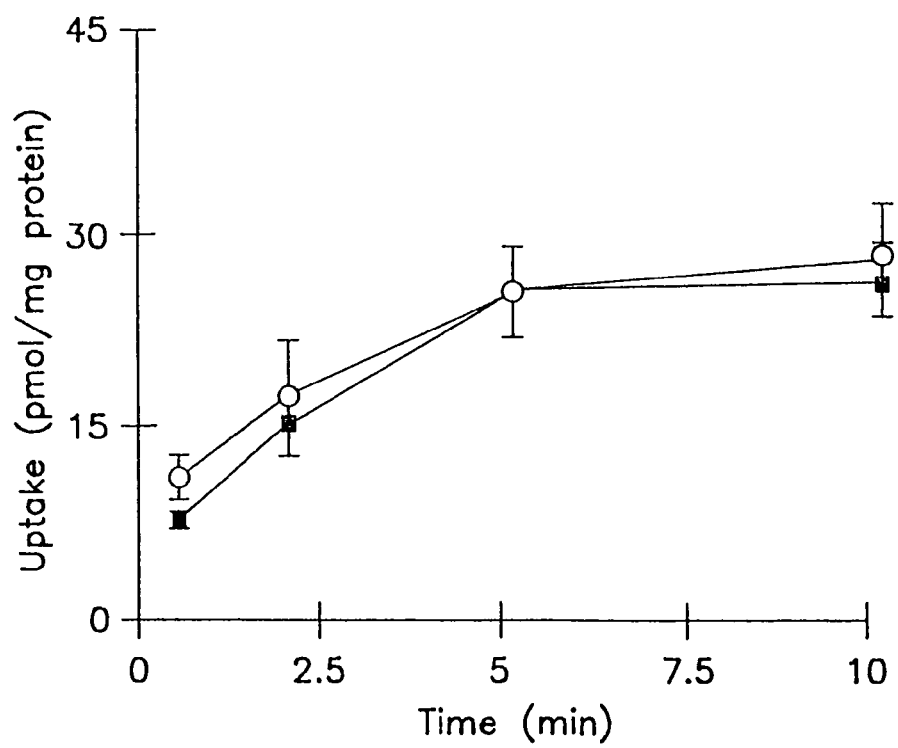
FIG. 2B is a graph depicting cumulative uptake of [$^{14}$C] salicylate (1 μM) in standard buffer (closed symbols) and Ca$^{2+}$-free buffer (open symbols) in hepatocytes cultured in a sandwich configuration for 96 hr.
Figure 3A:
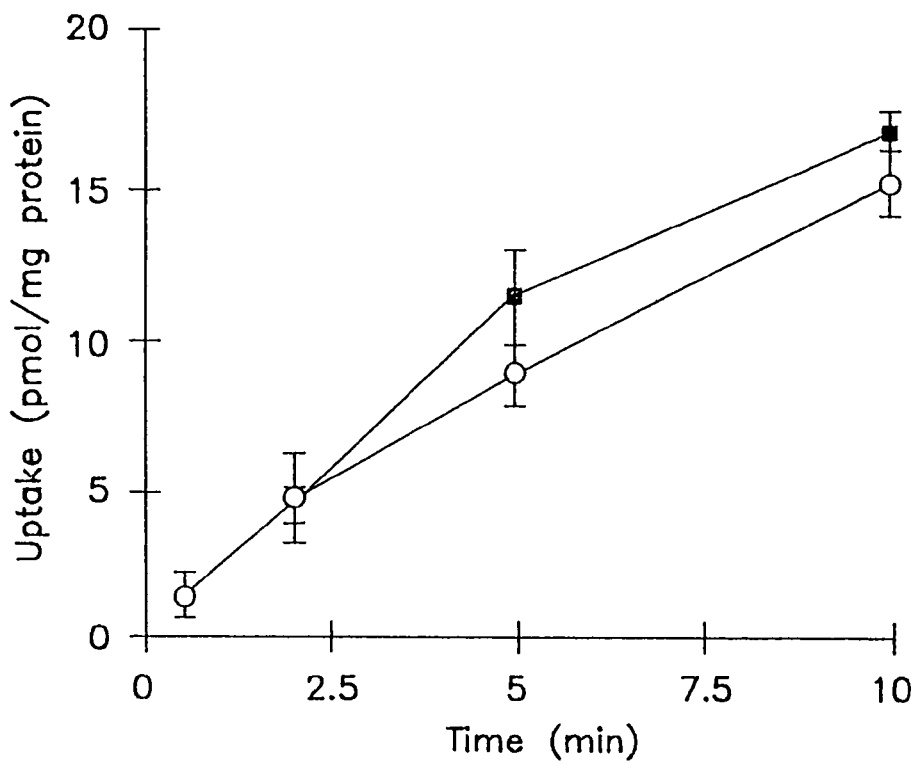
FIG. 3A is a graph depicting cumulative uptake of [$^3$H] methotrexate (1 μM) in standard buffer (closed symbols) and Ca$^{2+}$-free buffer (open symbols) in hepatocyte monolayers cultured for 3 hr.
Figure 3B:
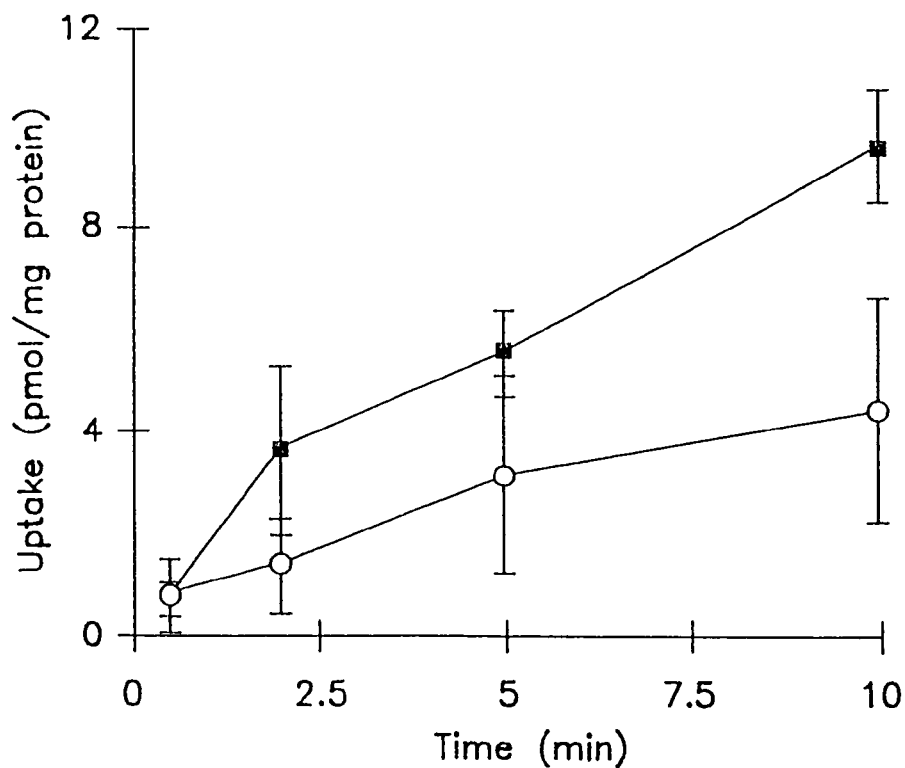
FIG. 3B is a graph depicting cumulative uptake of [$^3$H] methotrexate (1 μM) in standard buffer (closed symbols) and Ca$^{2+}$-free buffer (open symbols) in hepatocytes cultured in a sandwich configuration for 96 hr.
Figure 4A:
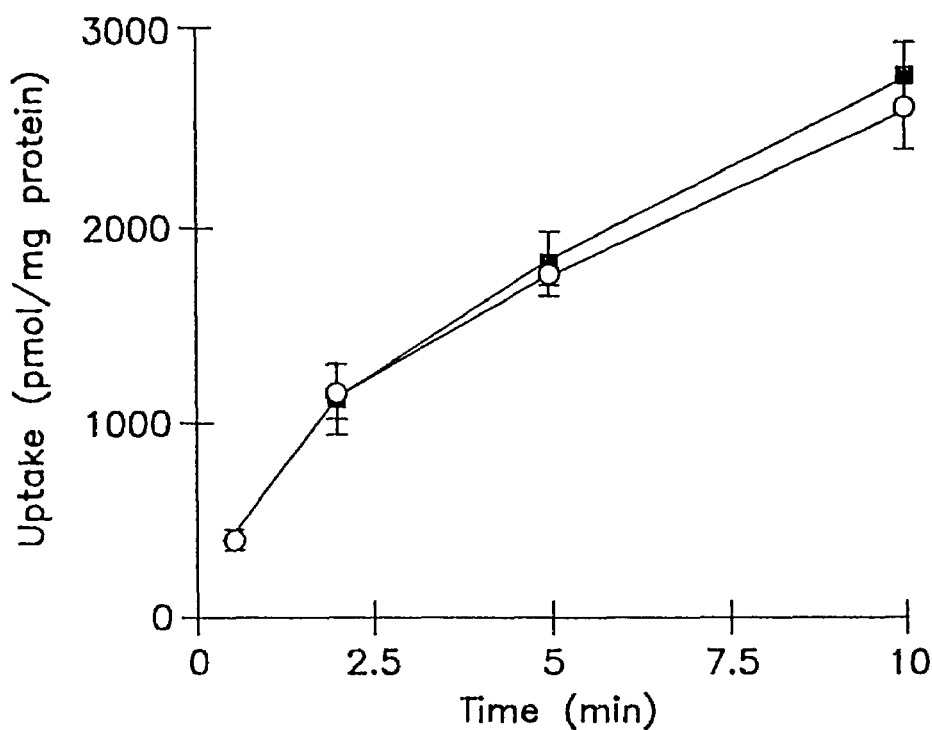
FIG. 4A is a graph depicting cumulative uptake of [$^3$H][D-pen$^{2,5}$]enkephalin (15 μM) in standard buffer (closed symbols) and Ca$^{2+}$-free buffer (open symbols) in hepatocyte monolayers cultured for 3 hr.
Figure 4B:
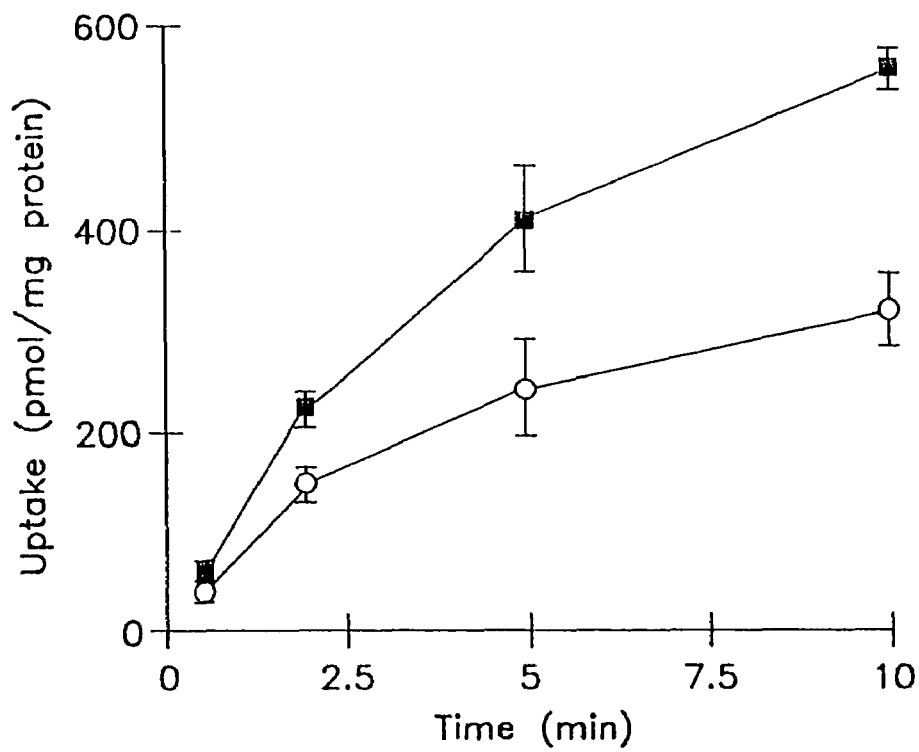
FIG. 4B is a graph depicting cumulative uptake of [$^3$H][D-pen$^{2,5}$]enkephalin (15 μM) in standard buffer (closed symbols) and Ca$^{2+}$-free buffer (open symbols) in hepatocytes cultured in a sandwich configuration for 96 hr.
Figure 5A:
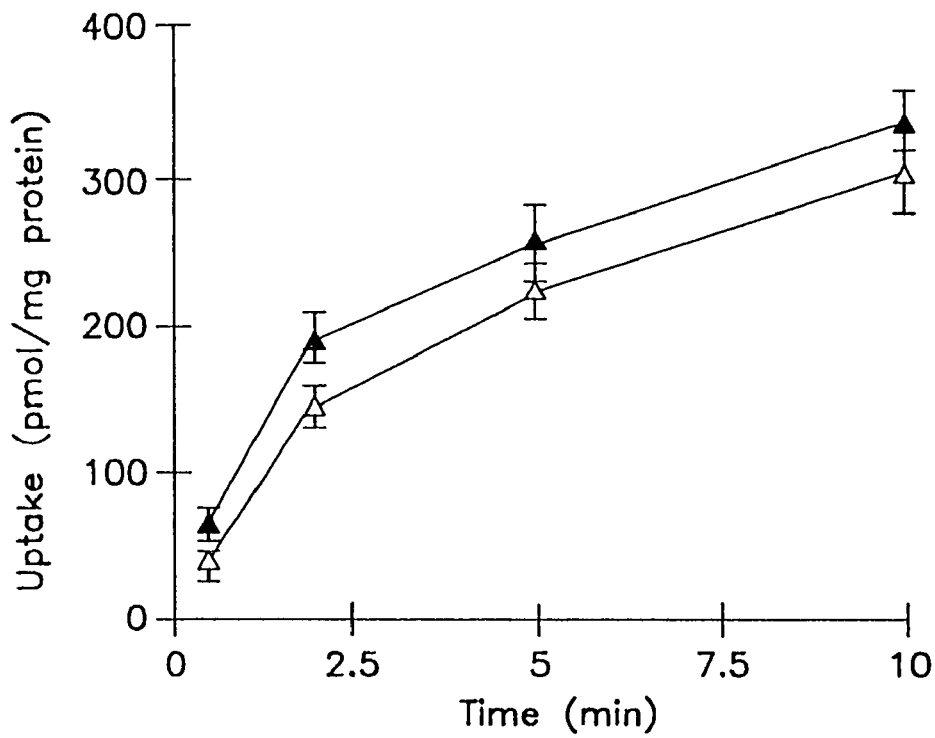
FIG. 5A is a graph depicting cumulative uptake of [$^3$H] taurocholate (1 μM) in standard buffer (closed symbols) and Ca$^{2+}$-free buffer (open symbols) in hepatocyte monolayers cultured for 3 hr.
Figure 5B:
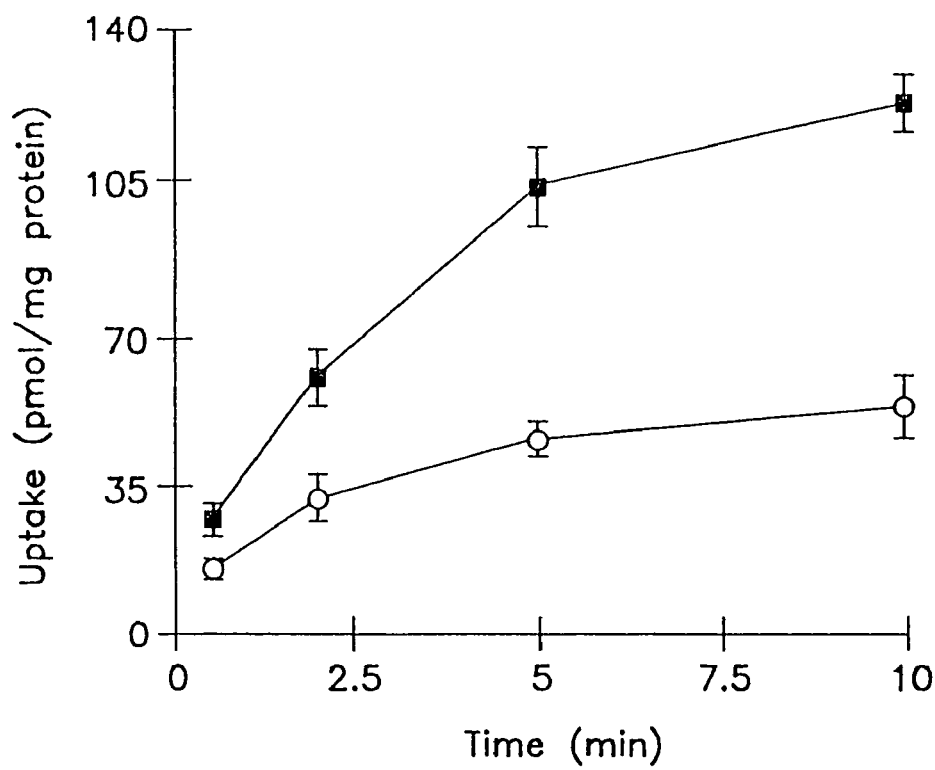
FIG. 5B is a graph depicting cumulative uptake of [$^3$H] taurocholate (1 μM) in standard buffer (closed symbols) and Ca$^{2+}$-free buffer (open symbols) in hepatocytes cultured in a sandwich configuration for 96 hr.

The cumulative uptake of inulin was negligible (less than 0.01% of initial added substrate) at all incubation times in either short-term or long-term cultured hepatocytes (FIGS. 1A and 1B). In the 3-hr cultured hepatocytes, the cumulative uptake of salicylate, methotrexate and [D-pen$^{2,5}$]enkephalin was not significantly different in standard buffer and in Ca$^{2+}$-free buffer (FIGS. 2A, 3A, and 4A; p>0.05). However, slightly higher cumulative uptake of taurocholate in standard buffer compared to Ca$^{2+}$-free buffer was observed (FIG. 5A); at 10 min, the cumulative uptake in standard buffer was approximately 10% higher than in Ca$^{2+}$-free buffer (p=0.0352). In 96-hr cultured hepatocytes, extracellular Ca$^{2+}$ had no effect on the cumulative uptake of salicylate (FIG. 2B, p>0.05). However, the uptake of methotrexate, [D-pen$^{2,5}$]enkephalin, and taurocholate in long-term cultured hepatocytes in standard buffer was significantly higher than in Ca$^{2+}$-free buffer (FIG. 3B, 4B, and 5B; p<0.05).

EXAMPLE 2

Relationship Between the Percentage of Dose Excreted in Bile in Rats And Biliary Excretion Index in Cultured Hepatocytes The five model substrates representing a diverse spectrum of biliary excretion properties were selected to examine the relationship between the percentage of the dose excreted in bile in vivo in rats and the Biliary Excretion Index in sandwich-cultured hepatocytes. Information regarding the percentage of the dose excreted in rat bile after i.v. administration was obtained from the literature. The extent of inulin and salicylate secretion into bile was negligible (Eriksson et al., *Acta. Physiol. Scand.* 95:1-5, 1975; Laznicekand et al., *Eur. J. Drug Met. Pharmacokinet.* 19:21-26, 1994). Approximately 50-60% of a 22 μmol/kg methotrexate dose (Bremnes et al., *Cancer Res.* 49:2460-2464, 1989; Masuda et al., *Cancer Res.* 57:3506-10, 1997) and 70% of a 14.5 μmol/kg [D-pen$^{2,5}$] enkephalin dose (Chen et al., *Pharm. Res.* 14:345-350,1997) were excreted into rat bile as unchanged drug in 1 hr. Taurocholate biliary excretion was more rapid and extensive than methotrexate and [D-pen$^{2,5}$]enkephalin. In 1 hr, virtually 100% of the dose (8.0 μmol/kg) was recovered in rat bile (Inoue et al., *Biochim. Biophys. Acta.* 833:211-216,1985).

Figure 6A:
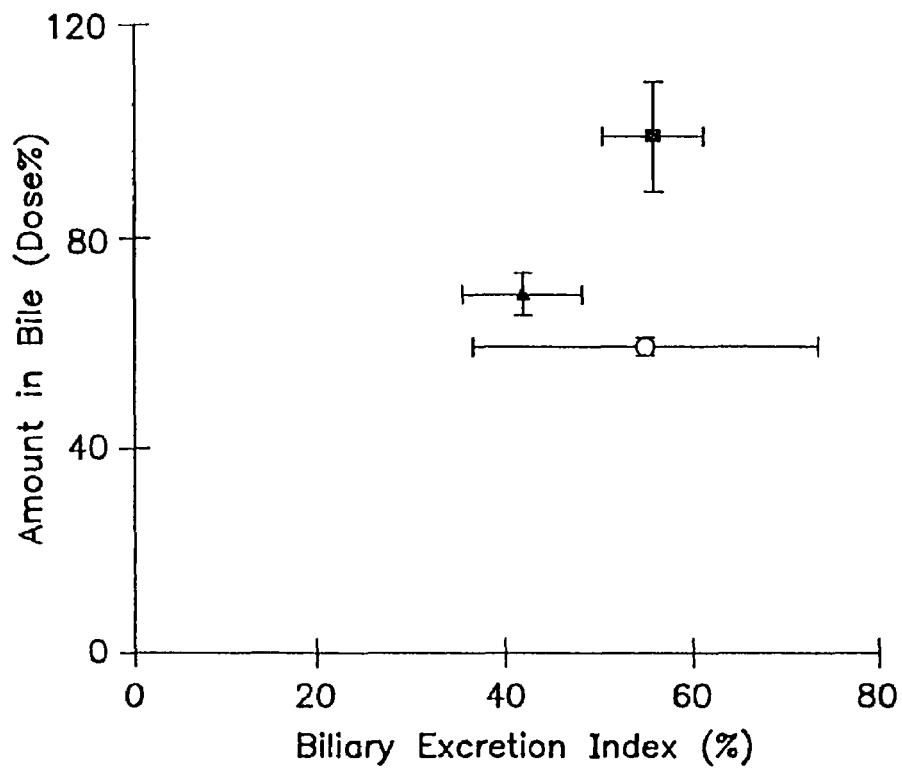
FIG. 6A is a graph depicting the relationship between the percentage of the dose excreted in rat bile in vivo and the Biliary Excretion Index in 96-hr sandwich cultured hepatocytes for the following model substrates: inulin (□), salicylate (◆), methotrexate (○), [D-pen$^{2,5}$]enkephalin (▲), and taurocholate (●). The Biliary Excretion Index was calculated from the 10-min cumulative uptake data (FIGS. 1A-5B) based on Equation 3. The broken line is the fit of a linear regression equation to the data.

Biliary excretion in the sandwich-cultured hepatocytes can be expressed quantitatively as the Biliary Excretion Index calculated from Equation 3 based on the 10-min cumulative uptake data in FIGS. 3B-5B. The Biliary Excretion Index of inulin and salicylate was assumed to be negligible because no statistically significant differences in the cumulative uptake of inulin or salicylate were observed between standard buffer and Ca$^{2+}$-free buffer (p>0.05). The Biliary Excretion Index of methotrexate, [D-pen$^{2,5}$]enkephalin and taurocholate was 55.4±18.3%, 42.4±6.5% and 56.4±5.2%, respectively. The relationship between the percentage of the dose excreted in rat bile in vivo and the Biliary Excretion Index measured in the in vitro system is depicted in FIG. 6A. The Biliary Excretion Index was very low for compounds undergoing negligible biliary excretion in vivo (e.g., inulin and salicylate). In contrast, the Biliary Excretion Index was moderately high for compounds that are excreted in bile in vivo (e.g., methotrexate, [D-pen$^{2,5}$]enkephalin, and taurocholate).

EXAMPLE 3

Correlation of In Vitro and In Vivo Biliary Clearance

The in vivo biliary clearance (ml/min per kg body weight) of inulin, salicylate, methotrexate and taurocholate was 0.035 (Utesch et al., *Vitro Cell. Dev. Biol.* 27A:858-863, 1991), ~0 (Laznicekand et al., *Eur. J. Drug Met Pharmacokinet.* 19:21-26, 1994), 12.1 (Masuda et al., *Cancer Res.* 57:3506-10, 1997), and 29.8 (Inoue et al., *Biochim. Biophys. Acta.* 833: 211-216,1985), respectively. In vivo biliary clearance of [D-pen$^{2,5}$]enkephalin, 18.5 ml/min/kg, was calculated based on Equation 1 from the data reported by Chen and Pollack (Chen and Pollack, *Pharm. Res.* 14:345-350, 1997). Based on these in vivo biliary clearance values, the intrinsic biliary clearance of inulin, salicylate, methotrexate, [D-pen$^{2,5}$]enkephalin and taurocholate was calculated from Equation 2 (0.04, 0. 17.3, 34.4, and 116.9 ml/min/kg, respectively).

Figure 6B:
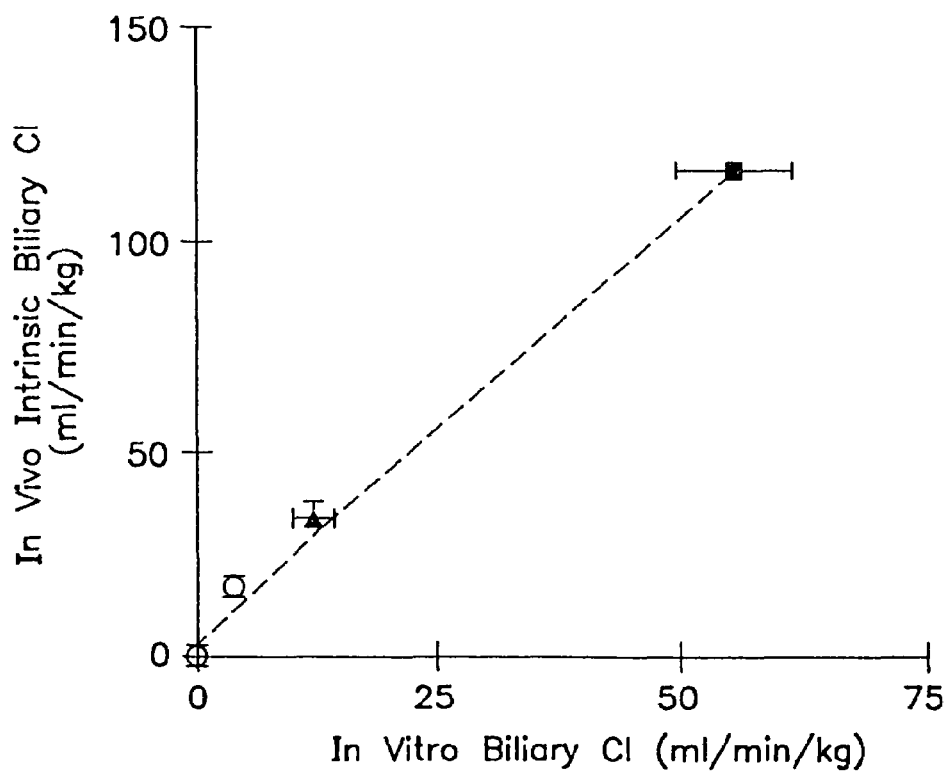
FIG. 6B is a graph depicting the relationship between the percentage of the dose excreted in rat bile in vivo and in vivo intrinsic biliary clearance and in vitro biliary clearance in 96-hr sandwich cultured hepatocytes for the following model substrates: inulin (□), salicylate (◆), methotrexate (○), [D-pen$^{2,5}$]enkephalin (▲), and taurocholate (●). The in vivo intrinsic biliary clearance was calculated from Equation 2 based on in vivo biliary clearance values from the literature. The in vitro biliary clearance was calculated from Equation 4. The broken line is the fit of a linear regression equation to the data.

The in vitro biliary clearance of inulin, salicylate, methotrexate, [D-pen$^{2,5}$]enkephalin and taurocholate, calculated from Equation 4 based on the 10-min cumulative uptake data (FIGS. 1B-5B) was ~0, ~0, 4.1±1.0, 12.6±2.2, and 56.2±6.0 ml/min/kg, respectively. The in vivo intrinsic biliary clearance correlated well with the in vitro biliary clearance ($r^2$=0.9865) for the five model compounds (FIG. 6B).

EXAMPLE 4

Figure 9A:
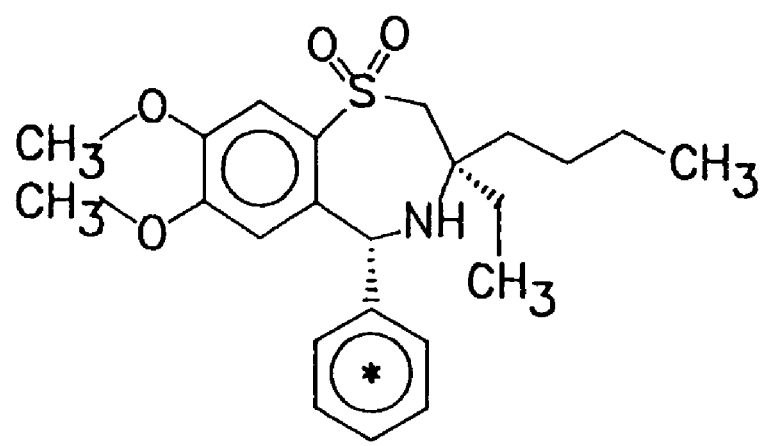
FIG. 9A presents the chemical structures of the compound 264W94, wherein the asterisk sign indicates the position of $^{14}$C incorporated uniformly.
Figure 9B:
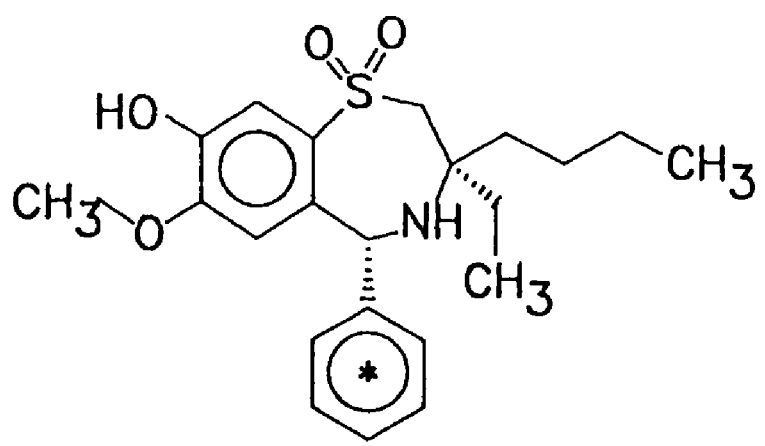
FIG. 9B presents the chemical structures of the compound 2169W94, wherein the asterisk sign indicates the position of $^{14}$C incorporated uniformly.

Comparison of In Vivo and In Vitro Biliary Excretion of 264W94 and its Metabolites The structural formulas of compounds 264W94 and 2169W94 are presented in FIG. 9. Compound 2169W94 is the O-demethylated metabolite of 264W94 in rats and humans, which can undergo further conjugation with urindine-5'-diphosphoflucuronic acid to form a glucuronide conjugate (Silver et al., *ISSX Proceedings*, (San Diego, Calif. USA) pp. 387,1996).

After i.v. administration of [$^{14}$C]264W94 to rats (0.24 μmol/kg), neither 264W94 nor 2169W94 was detected in bile in 24 hr. However, 35.4% (n=2) of the total administered radioactivity was recovered in bile in the first hour. Approximately, 30.0% of the radioactivity recovered in bile was the 2169W94 glucuronide; the remaining 70% of radioactivity in bile represented unidentified metabolites. After oral administration of [$^{14}$C]264W94 to rats (2.4 μmol/kg), 2169W94 was not detected in the bile in 24 hr. However, 66.4% (n=2) of the total administered radioactivity was recovered in bile in 8 hr. Approximately, 88.7% of the radioactivity in bile was in the form of the 2169W94 glucuronide conjugate. These in vivo results demonstrate that 264W94 and its 0-demethylated product, 2169W94, undergo negligible biliary excretion, but the glucuronide conjugate of 2169W94 undergoes extensive biliary excretion in rats.

Figure 7A:
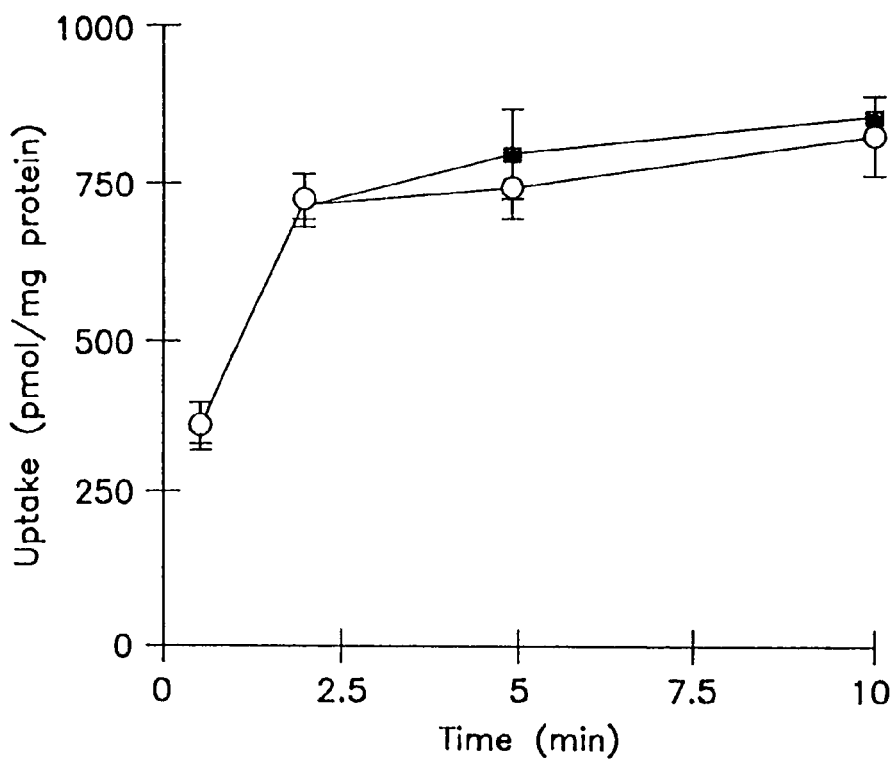
FIG. 7A is a graph depicting cumulative uptake of [$^3$H] 264W94 (3 μM) in standard buffer (closed symbols) and Ca$^{2+}$-free buffer (open symbols) in hepatocyte monolayers cultured for 3 hr.
Figure 7B:
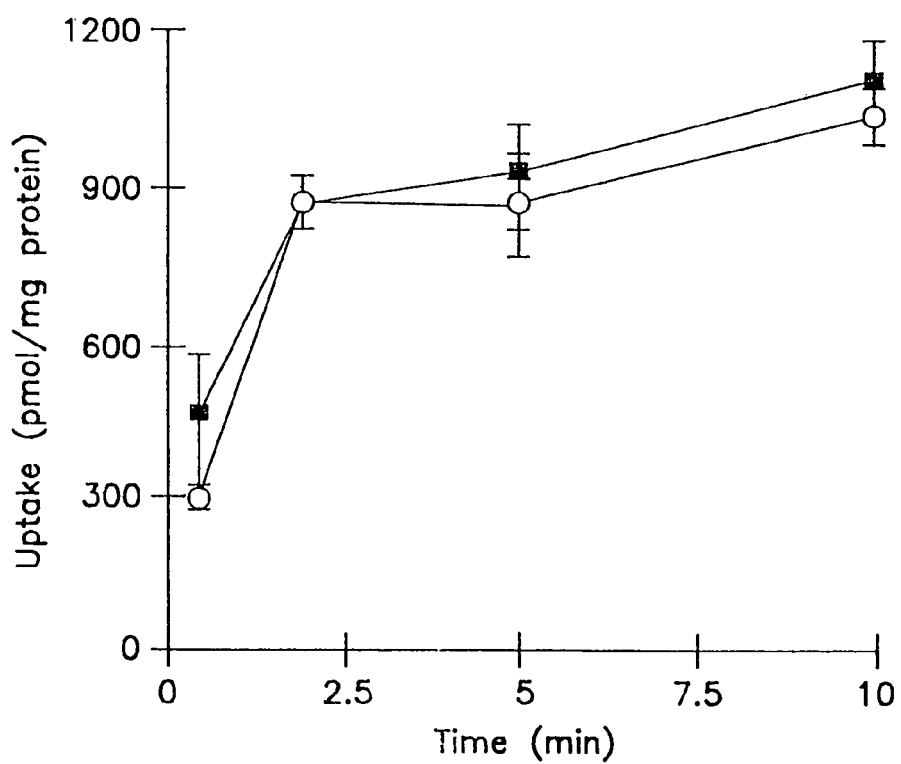
FIG. 7B is a graph depicting cumulative uptake of [$^3$H] 264W94 (3 μM) in standard buffer (closed symbols) and Ca$^{2+}$-free buffer (open symbols) in hepatocytes cultured in a sandwich configuration for 96 hr.
Figure 8A:
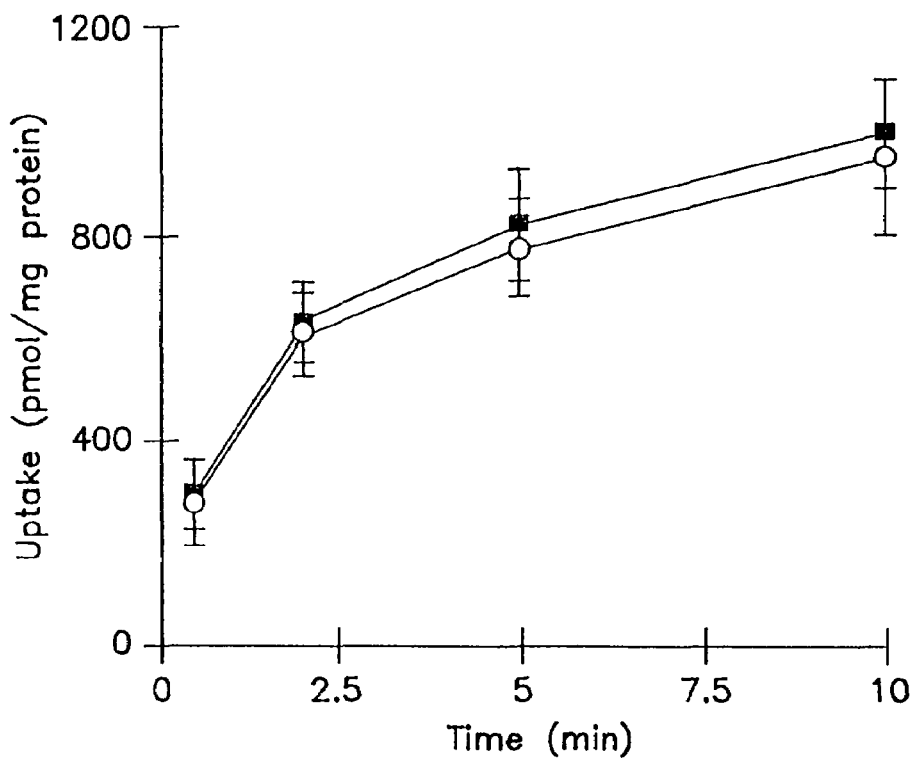
FIG. 8A is a graph depicting cumulative uptake of [$^3$H] 2169W94 (3 μM) in standard buffer (closed symbols) and Ca$^{2+}$-free buffer (open symbols in hepatocyte monolayers cultured for 3 hr.

To determine the biliary excretion of 264W94 and metabolites in 3-hr and 96-hr cultured hepatocytes, hepatocyte monolayers were incubated in standard or $Ca^{2+}$-free buffer before cumulative uptake was conducted in standard buffer containing 3 μM of [$^{14}$C]264W94 or [$^{14}$C]2169W94 (FIG. 7 and 8). In 3-hr cultured hepatocytes, the cumulative uptake measured by total radioactivity of 264W94 or 2169W94 was similar in the hepatocytes pre-incubated in standard buffer or $Ca^{2+}$-free buffer (p>0.05), suggesting that the uptake of 264W94 and 2169W94 in short-term cultured hepatocytes was not affected by pre-incubation of the monolayers in $Ca^{2+}$-free buffer. In 96-hr cultured hepatocytes, the 10-min cumulative uptake of 264W94 measured by total radioactivity was not significantly different in the monolayers pre-incubated in standard buffer or $Ca^{2+}$-free buffer (p>0.05).

HPLC analysis of the cell lysate at 10 min revealed that 73.0% of the total radioactivity was in the form of 264W94 and 3.3% was the 2169W94 glucuronide conjugate; 2169W94 was not detected in the lysate. In 96-hr sandwich-cultured hepatocytes, 10-min cumulative uptake of 2169W94 was approximately 70% greater in the presence of $Ca^{2+}$ than in the absence of $Ca^{2+}$ (p>0.05). In the 10-min cell lysate, approximately 16.7% of total radioactivity was in the form of 2169W94, and approximately 58.5 was the 2169W94 glucuronide conjugate. Compound 2169W94 forms the glucuronide conjugate which is excreted into bile canalicular networks in long-term cultured hepatocytes.

To further characterize the utility of the in vitro biliary excretion assay of the presently disclosed subject matter to predict in vivo biliary excretion of drug metabolites, the in vitro and in vivo biliary excretion of 264W94, and its O-demethylated metabolites 269W694 and 2169W94 glucuronide were examined. Previous in vitro studies conducted with rat and human liver microsomes, precision cut liver slices, and CDNA expressed hepatic cytochrome p450 isozymes indicated that 264W94 formed an O-demethylated metabolite at the 8-methoxy position. Among the several cytochrome p450 isozymes examined, CYP3A4 was the isozyme primarily involved in the metabolism of 264W94 (Silver et al., *ISSX Proceedings* (San Diego, Calif. USA) p. 387,1996).

In vivo disposition studies demonstrated that neither 264W94 nor its O-demethylated metabolite, 2169W94, was excreted in the bile. But, the 2169W94 glucuronide conjugate, along with other unidentified metabolites, were extensively excreted in bile. The lack of biliary excretion of 264W94 in long-term sandwich-cultured hepatocytes was consistent with negligible in vivo biliary excretion of 264W94.

In vivo, approximately 35% of 264W94 equivalent was excreted in bile as metabolites in 1 hr after i.v. administration of 264W94. In cultured hepatocytes, however, the biliary excretion of 264W94 metabolites was negligible (FIG. 7B). This apparent discrepancy between the in vivo and in vitro biliary excretion for metabolites of 264W94 may be explained by differences in metabolic activities. In vivo, 264W94 undergoes O-demethylation to form 2169W94; and subsequently, 2169W94 is conjugated with uridine-5'-diphosphoglucuronic acid to form 2169W94 glucuronide. This glucuronide conjugate accounts for 30% of the total amount excreted in bile. In the lysate of long-term sandwich-cultured hepatocytes incubated with 264W94, only approximately 3% of the total amount incubated was detected as the 2169W94 glucuronide conjugate. These results indicated that the long-term cultured hepatocytes were not capable of the O-demethylation reaction. Consequently, negligible glucuronide conjugate was formed and excreted in the bile.

Figure 8B:
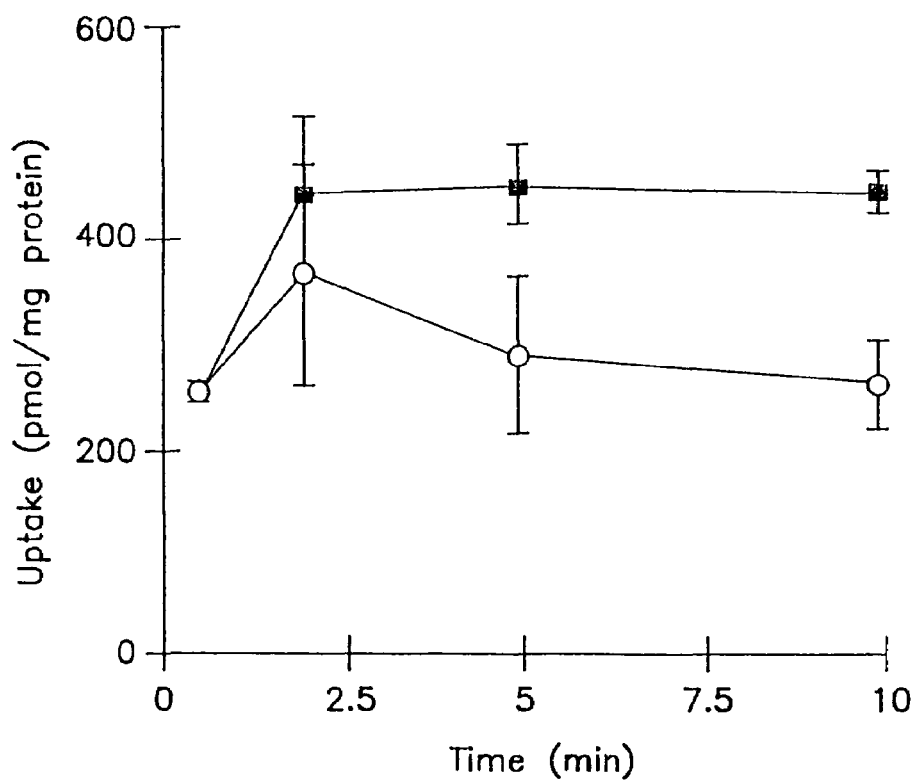
FIG. 8B is a graph depicting cumulative uptake of [$^3$H] 2169W94 (3 μM) in standard buffer (closed symbols) and Ca$^{2+}$-free buffer (open symbols) in hepatocytes cultured in a sandwich configuration for 96 hr.

However, after incubation of the monolayers with 2169W94, the O-demethylated metabolite of 264W94, 58.5% of 2169W94 was converted to glucuronide conjugates and significant biliary excretion was observed in the cultured hepatocytes (FIG. 8B). Evidently, phase I metabolic activities such as O-demethylation deteriorate significantly, while the phase II metabolic activities such as glucuronide conjugation are maintained, at least in part, in the long-term sandwich-cultured hepatocytes used in accordance with the presently disclosed subject matter. Thus, this Laboratory Example further indicates that the assay of the presently disclosed subject matter can be employed to predict in vivo biliary excretion of a substrate in its parent form. Indeed, the application of the present in vitro assay method to study and to predict in vivo biliary excretion of metabolites requires consideration of the status of metabolic activities in the monolayers.

EXAMPLE 5

Inhibition of Expression of MRP2 and MRP3 by siRNA in Sandwich-Cultured Rat Hepatocytes Prior to the present disclosure, siRNA had not been employed in primary hepatocytes to specifically knock down the expression of important drug transport genes. Therefore, an objective of this Example was to utilize siRNA to modulate the expression of Mrp2 and Mrp3 and elucidate the functional consequences in sandwich-cultured rat hepatocytes (SCRH).

Materials and Methods

Cell Culture of Human Hepatoblastoma (HepG2) Cells and Primary Rat Hepatocytes

HepG2 cells were maintained in Dulbecco's modified Eagle's medium/F-12 plus 10% FBS. Rat hepatocytes were isolated from male Wistar rats (220-300g) by in situ collagenase perfusion (Annaert et al., *Drug Metab Dispos* 29:1277-1283, 2001). Cells were seeded at a density of $1.5 \times 10^6$ cells per well onto polystyrene 6-well plates pre-coated with rat tail type I collagen; a top layer of gelled collagen was overlaid 24 hr after plating. Rat hepatocyte cultures were maintained in Dulbecco's modified Eagle's medium supplemented with 0.1 μM dexamethasone and 0.1% ITS culture supplement (6.25 mg/mL insulin, 6.25 mg/mL transferrin, 6.25 μg/mL selenous acid, 5.35 mg/mL linoleic acid, and 1.25 g/mL BSA). Medium was changed every 24 hr.

Synthesis of siRNA siRNA sequences targeting rat Mrp2 and Mrp3 were chosen with RNAi OligoRetriever (www.cshl.org/public/SCIENCE/hannon.htmL) for the T7 RNA polymerase protocol. Single-stranded RNA was synthesized with a T7-MEGASHORTSCRIPT™ High Yield Transcription Kit (Ambion Inc. Austin, Tex. USA) according to the manufacturer's instructions. To make double-stranded siRNA, sense and antisense of single-stranded RNAs in equimolar amounts were denatured and annealed with a thermocycler (95° C., 5 min; 70° C., 5 min; 50° C., 5 min; 25° C., 5 min). The integrity of siRNA was examined with a 2% agarose gel. The following three siRNA antisense sequences targeting Mrp2 were synthesized: siMrp2AB1=GGCUAUAUCUGUGCAAUCCUA (SEQ ID NO: 3; UA 3' overhang in antisense strand and AA 3' overhang in sense strand), siMrp2AB2=GGCUAGGAAGCAGUACACCAU (SEQ ID NO: 4; AU 3' overhang in antisense strand and AA 3' overhang in sense strand), siMrp2AB3 =GGCAGUAGGGUGGUG-GUCCAU (SEQ ID NO: 5; AU 3' overhang in antisense strand and UG 3' overhang in sense strand). The following antisense sequence was used to target Mrp3: GGUCCAAGGAC-CUGCCUCCCA (SEQ ID NO: 6; CA 3' overhang in antisense strand, AG 3' overhang in sense strand). The siRNA sequence [antisense=GUGCGCUGCUGGUGCCAACUU (SEQ ID NO: 7; 3' overhangs in both strands)] targeting firefly (*Photinus pyralis*) luciferase (siFL) was adapted from a known potent sequence for this protocol (Miyagishi and Taira, *Nat. Biotechnol.* 20:497-500, 2002).

Intracellular Tracking of siRNA siRNA was covalently attached to the Cy3 dye in a one-step chemical reaction with the LABELIT® siRNA Tracker Intracellular Localization Kit (Mirus Corporation, Madison, Wis. USA). Ten pg siRNA was incubated with 10 µl of reconstituted Cy3 labeling reagent at 37° C. for 1 hr. Labeled siRNA was purified by a regular ethanol precipitation method to remove excess Cy3. Cy3-labeled siRNA was transferred into SCRH as described in the following siRNA transfection section. Cell images were taken with an Axiovert 100TV inverted microscope (Zeiss, Thornwood, N.Y. USA).

siRNA Transfection

HepG2 cells were seeded at a density of 2×10⁵ cells per well onto 12-well plates 24 hr before transfection. A mixture of 100 ng firefly luciferase expression plasmid (PGL3-FL) and 100 ng *Renilla* luciferase expression plasmid (PRL-TK) and various amounts of firefly luciferase siRNA were used per well. Transfections of SCRH were performed at 20 hr after plating, unless specifically indicated. siRNA (2 µg unless specified) was used per well in 6-well plates. siRNA and DNA were formulated for transfection using TRANSMESSEN-GER™ transfection reaction kit (QIAGEN Inc. Valencia, Calif. USA). Briefly, siRNA was condensed in Enhancer EC at a ratio of 1:2 (µg of total RNA and/or DNA : µl of Enhancer), and formulated with TransMessenger at a ratio of 1:4 (µg of RNA and /or DNA: µl of TransMessenger) and then incubated with cells. For transfections of HepG2 cells, medium was changed after an overnight incubation with siRNA. For transfections of SCRH, cells were incubated with siRNA for 4 hr and then were overlaid with collagen. siRNA delivery into hepatocytes was more efficient before overlay of the top collagen layer. The effect of transfection was examined 48 hr later.

Luciferase Activity Assay

Luciferase activity was measured with the DUAL-LU-CIFERASE® Reporter Assay System (Promega Co. Madison, Wis. USA). Briefly, HepG2 cells were lysed in 100 µl passive lysis buffer. Twenty µl cell lysate was mixed with 100 µl Luciferase Assay Reagent II to measure firefly luciferase activity. Stop and Glo Reagent (100 µl) was then added and mixed to measure the *Renilla* luciferase activity. Luminescence intensity was measured with a MONOLIGHT™ 3010 Luminometer (BD Biosciences, San Jose, Calif. USA).

Immunoblot Analysis

Cells were harvested 48 hr post transfection and lysed in 1% SDS, 1 mM EDTA plus COMPLETE™ protease inhibitor cocktail (Roche Diagnostics, Mannheim, Germany). The protein concentration of the clear cell lysate was determined with the BCA Protein Assay Reagent Kit (Pierce Biotech, Inc. Rockford, Ill.). Fifty pg of total protein per lane was resolved by electrophoresis on NuPAGE 4-12% Bis-Tris Gel (Invitrogen Life Technology, Carlsbad, Calif. USA) and were transferred onto polyvinylidone difluoride membranes. The following antibodies were used to probe the membranes: anti-Mrp2 (M2111-6, Alexis Biochemicals, San Diego, Calif. USA); anti-Mrp3 (kind gift from Dr. Yuichi Sugiyama); anti-Radixin (Chemicon International, Inc. Temecula, Calif. USA), anti-β-actin (MAB1501, Chemicon).

Assessment of Mrp2 and Mrp3 Function with CDF Disposition

Cells were rinsed twice with Hanks' balanced salt solution (HBSS, 2 mL, 37° C.) and incubated (10 min, 1.5 mL, 37° C.) with 2 µM CDF diacetate (Molecular Probes, Eugene, Oreg. USA), and were then rinsed twice with cold HBSS (2 mL, 4° C.). Cell images were taken with a Axiovert 100TV inverted microscope. Accumulation of CDF in cells+bile canaliculi and cells only was assessed in SCRH pre-incubated (10 min, 2 mL, 37° C.) with standard HBSS and $Ca^{2+}$-free HBSS, respectively (Liu et al., *J. Pharmacol. Exp. Ther.* 289:1592-1599, 1999). SCRH were subsequently incubated with CDF diacetate (10 min, 2 mL, 37° C.). In siMrp2-treated SCRH, cells were then rinsed four times with cold HBSS (2 mL, 4° C.) and lysed (1 mL, 0.5% TritonX-100 in phosphate-buffered saline). In siMrp3-treated SCRH, following incubation with CDF diacetate, cells were rinsed four times with warm HBSS (2 mL, 37° C.) and were incubated with HBSS (30 min, HBSS changed every 10 min, 2 mL, 37° C.) to allow time for intracellular CDF to undergo appreciable basolateral excretion prior to rinsing the SCRH four times with cold HBSS and lysing the cells (as above). CDF fluorescence in lysate was quantified with fluorescence spectrophotometry ($\lambda_{ex}$=485 nm, $\lambda_{em}$=590 nm); protein concentration was determined with the BCA method kit (as above).

Lactate Dehydrogenase Activity Assay

Prior to the functional studies, cell culture medium was assayed for lactate dehydrogenase activity, an intracellular enzyme whose leakage into extracellular medium is inversely related to cell viability. Lactate dehydrogenase activity was assayed with kit 500-C (Sigma Diagnostics, St. Louis, Mo. USA) utilizing lactate dehydrogenase-catalyzed reduction of pyruvate to lactate, subsequent conjugation of remaining pyruvate with 2,4-dinitrophenylhydrazine, and spectrophotometric detection ($\lambda$=500 nm) of the pyruvate-2,4-dinitrophenylhydrazone conjugate at alkaline pH (Cabaud and Wroblewski, *Am. J. Clin. Pathol.* 30:234-236,1958).

Statistics

Data are reported as mean±SD, except where indicated otherwise. Statistical significance was evaluated with one-way or two-way ANOVA with Tukey's post-hoc test. In all cases, p<0.05 was deemed significant.

Results

Figure 10:
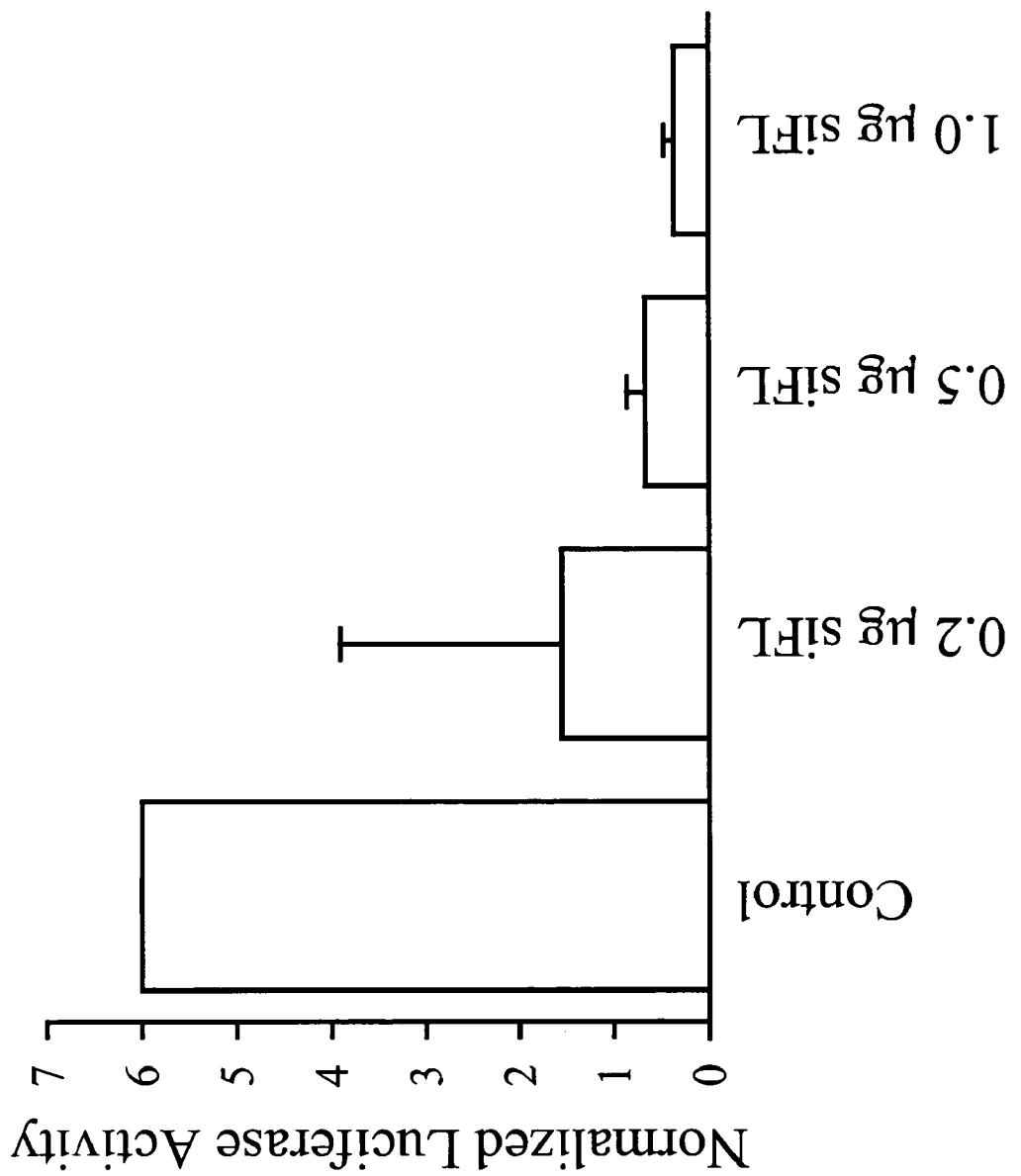
FIG. 10 is a graph showing the knockdown effect of siFL synthesized with the T7 RNA polymerase method. Firefly luciferase activity was examined in HepG2 cells transfected with PGL3-FL (firefly luciferase) and PRL-TK (Renilla luciferase) plasmids plus 0.2, 0.5 or 1.0 μg of siFL; activity was normalized against that of Rennila luciferase. Only PGL3-FL and PRL-TK plasmids were used in control transfection. Mean±range (n=2).

Validation of siRNA Activity, Delivery, Efficacy, and Toxicity was first examined. siRNA targeting firefly luciferase (siFL) with proven knockdown effect was synthesized and used to examine the knockdown effect on the expression of firefly luciferase expressed from the PGL3-FL plasmid in HepG2 cells. HepG2 cells were treated with 0.2, 0.5 and 1.0 µg of siFL; 48 hr after transfection *Renilla* luciferase-normalized activity of firefly luciferase was decreased 74%, 89% and 94%, respectively (FIG. 10).

Figure 11:
FIG. 11 shows intracellular tracking of siRNA. siFL and siMrp2 were labeled with Cy3 reagent and transferred into SCRH prior to collagen overlay. Images were taken 24 hr after transfection.
Figure 11:
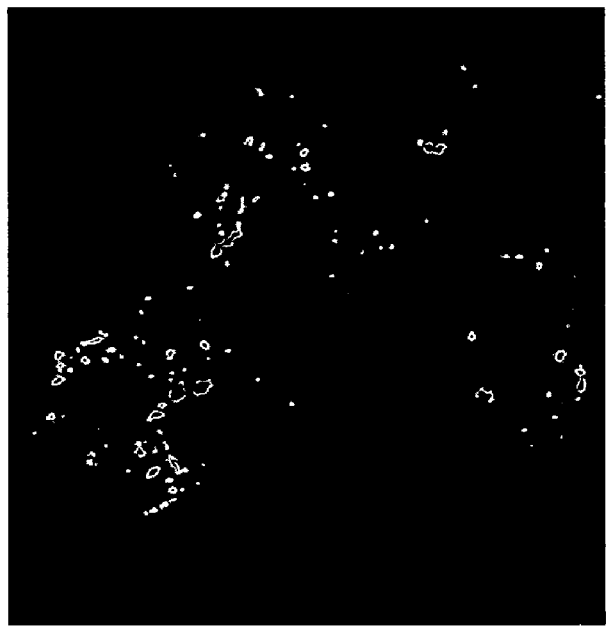

Cy3-labeled siRNA was used to examine siRNA delivery to hepatocytes after collagen overlay. siRNA was delivered successfully into hepatocytes before overlay (FIG. 11), but not into the hepatocytes after overlay.

Preliminary studies evaluated the knockdown effects from three different transfection timepoints (3 hr, 12 hr and 24 hr); the best effect was observed at 12 hr and 24 hr after plating. In the present studies all transfections were performed at 20 hr after plating (i.e. right before overlaying cells with collagen at 24 hr).

After three days in culture, the time at which transport protein levels and function were assessed, lactate dehydrogenase activity was not elevated in SCRH transfected with siMrp2 or siMrp3 siRNA (94±13, 87±3% non-transfected control SCRH, mean±SEM).

To ensure the efficient delivery of siRNA into SCRH, a transfection methodology was developed by testing transfection at different timepoints after plating the primary hepatocytes before and after overlaying the cells with rat tail collagen and tracking intracellular siRNA with cy3-label. Three siRNA sequences for Mrp2 (generally referred to herein and in the Figures as siMrp2), siMrp2AB1 (SEQ ID NO: 3), siMrp2AB2 (SEQ ID NO: 4) and siMrp2AB3 (SEQ ID NO:5) were synthesized. siMrp2AB1, targeting nucleotides 1158-1178 of the Mrp2 cDNA (SEQ ID NO: 1), had the most potent effect, which resulted in an average of 50% (maximum 79%) reduction in endogenous Mrp2 expression (FIGS. 12A and 12B) when compared to SCRH transfected with siFL or non-transfected SCRH. siMrp2AB2 also produced a significant knockdown effect (40±20%). siMrp2AB3 knocked down Mrp2 protein only modestly (26±18%). Surprisingly, the equal molar mixture of these three sequences exhibited the least knockdown effect (~13% reduction).

Figure 13A:
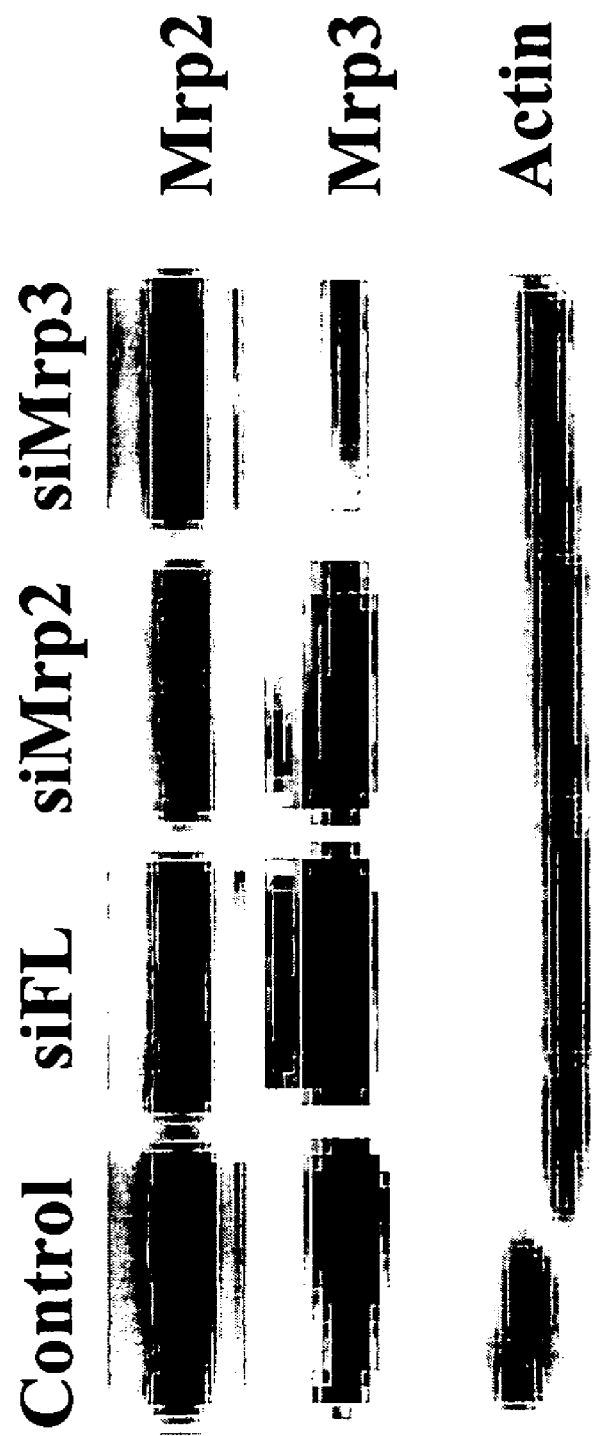
FIG. 13A presents immunoblot analysis of Mrp2 and Mrp3 expression in the SCRH treated with siMrp2, siMrp3, siFL and non-transfected SCRH.
Figure 13B:
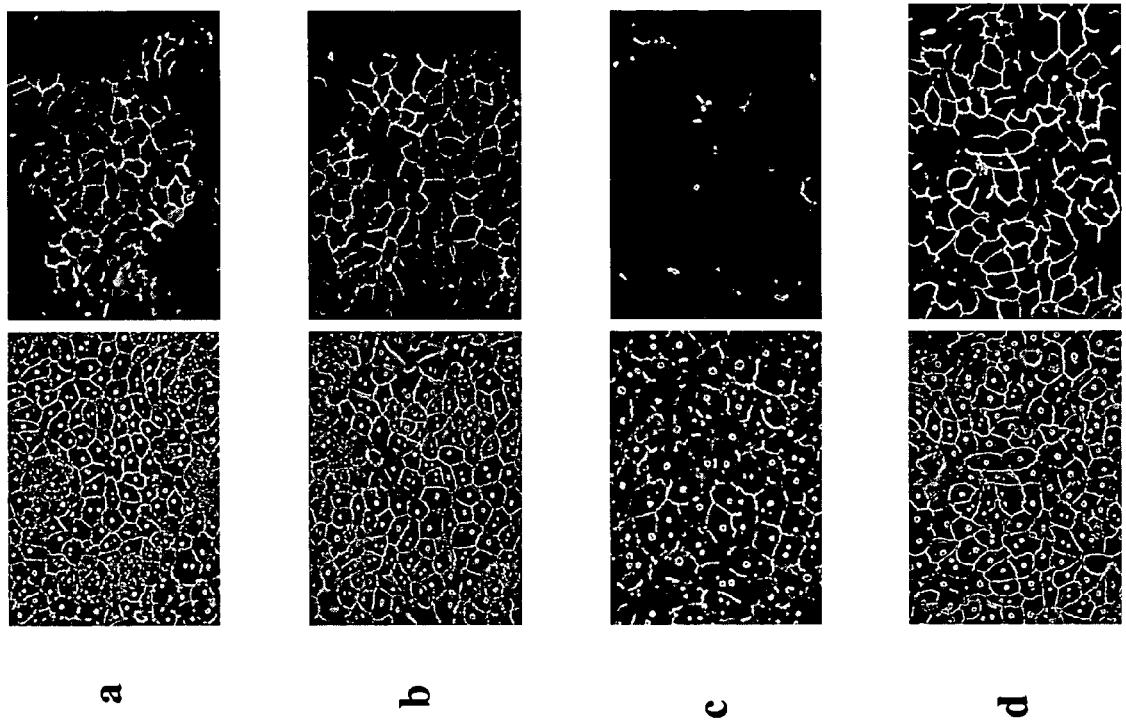
FIG. 13B shows CDF fluorescence in the canalicular networks of SCRH treated with siRNA. Light microscopy image (left panel) and fluorescence microscopy image (right panel) are shown side by side in (a) non-transfected cells, (b) siFL-, (c) siMrp2-, and (d) siMrp3-transfected cells.
Figure 13C:
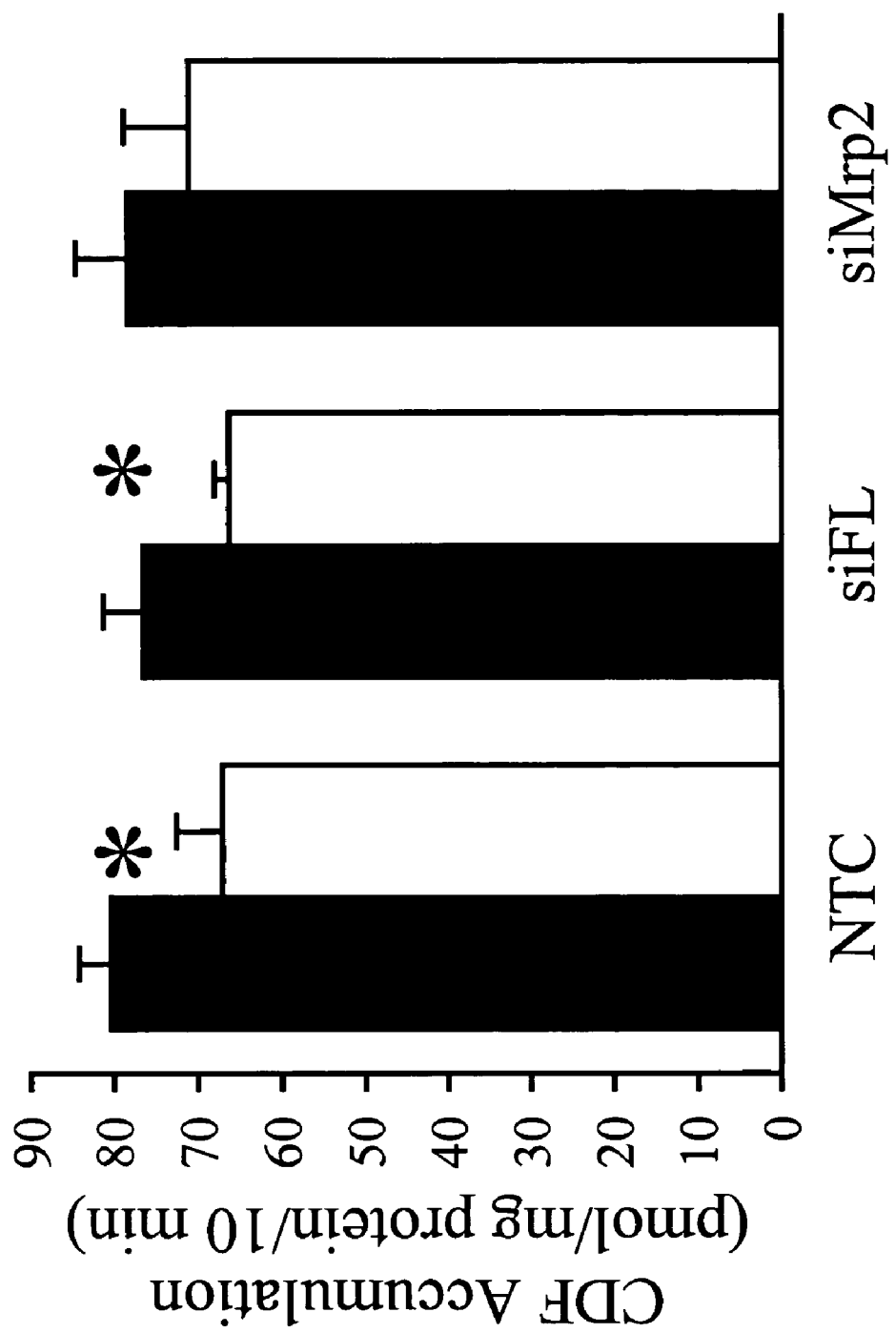
FIG. 13C shows CDF accumulation in siMrp2-, siFL-transfected, and non-transfected SCRH in the presence of standard Hank's balanced salt solution (HBSS, cells+bile canaliculi, closed bars) or Ca$^{2+}$-free HBSS (cells only, open bars) immediately following 10 min incubation with 2 μM CDF diacetate.

The decrease in Mrp2 function was demonstrated by fluorescence microscopy using the fluorescent Mrp2 substrate carboxydichlorofluorescein (CDF) (FIG. 13B). Nonfluorescence CDF diacetate passively diffuses into hepatocytes where it is hydrolyzed to the fluorescent CDF, which is actively excreted by Mrp2 across the canalicular membrane and accumulates in the canalicular networks of SCRH (Kikuchi et al., $Nat.\ Genet.$ 31:320-325, 2002). Fluorescence in the canalicular networks of SCRH treated with siMrp2 was markedly decreased (~45%) compared to SCRH treated with siRNA against firefly luciferase (siFL) or non-transfected SCRH.

Accumulation of CDF in control non-transfected cells+ bile canaliculi was significantly higher than in cells only (80.4±3.9 vs. 67±5.5 pmol/mg protein/10 min), indicating appreciable accumulation of CDF in bile canalicular networks. In contrast, in siMrp2-transfected SCRH, accumulation of CDF in cells+bile canaliculi was not significantly different from CDF accumulation in cells only (78.3±6.3 vs. 71.1±7.8). The percent fraction of CDF accumulated in cells+ bile canaliculi attributed to CDF accumulation in the bile canalicular networks was ~45% lower in siMrp2-transfected SCRH (9.3% vs. 16.5%).

Figure 12A:
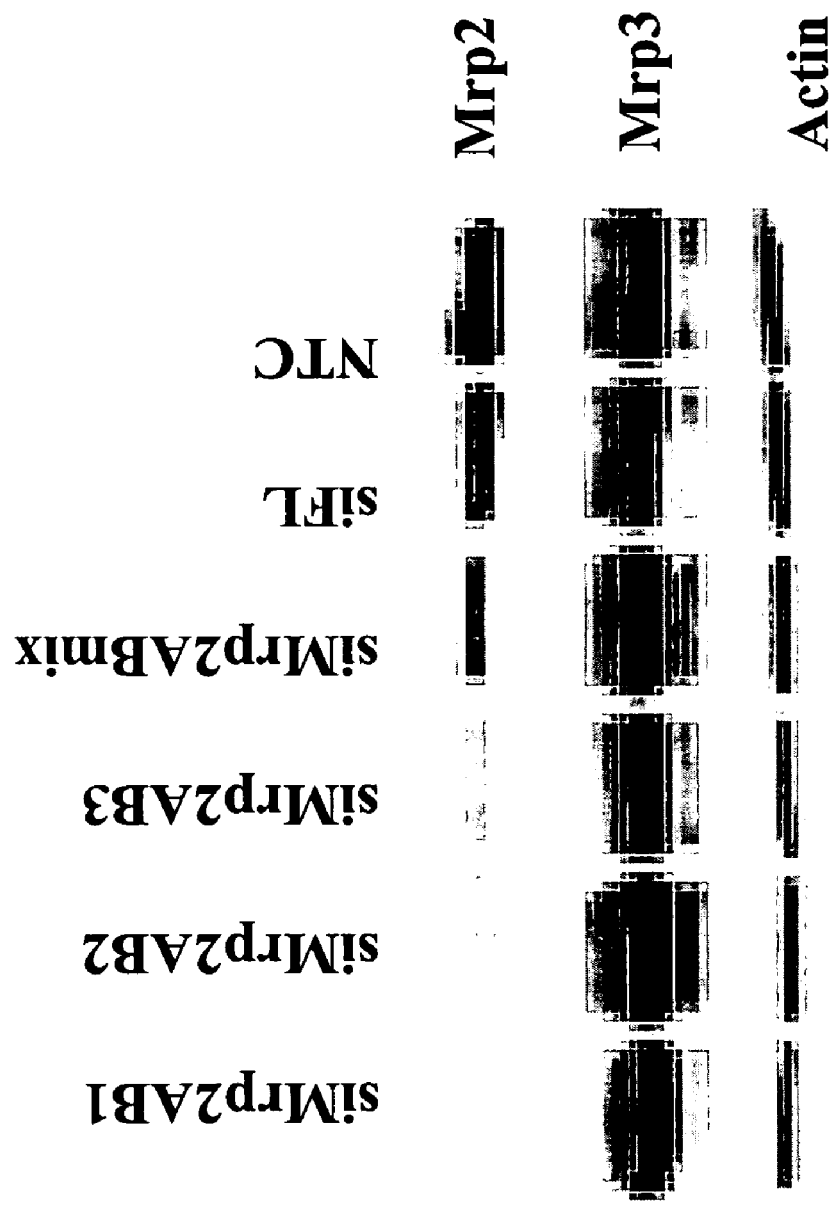
FIG. 12A is a representative immunoblot of the expression of Mrp2, Mrp3, radixin and actin in siMrp2-treated SCRH (2 μg per well) used in the transfection of SCRH on 6-well culture plates coated with rat tail collagen; immunoblot analysis was done 48 hr after the transfection; NTC is non-transfected control.
Figure 12B:
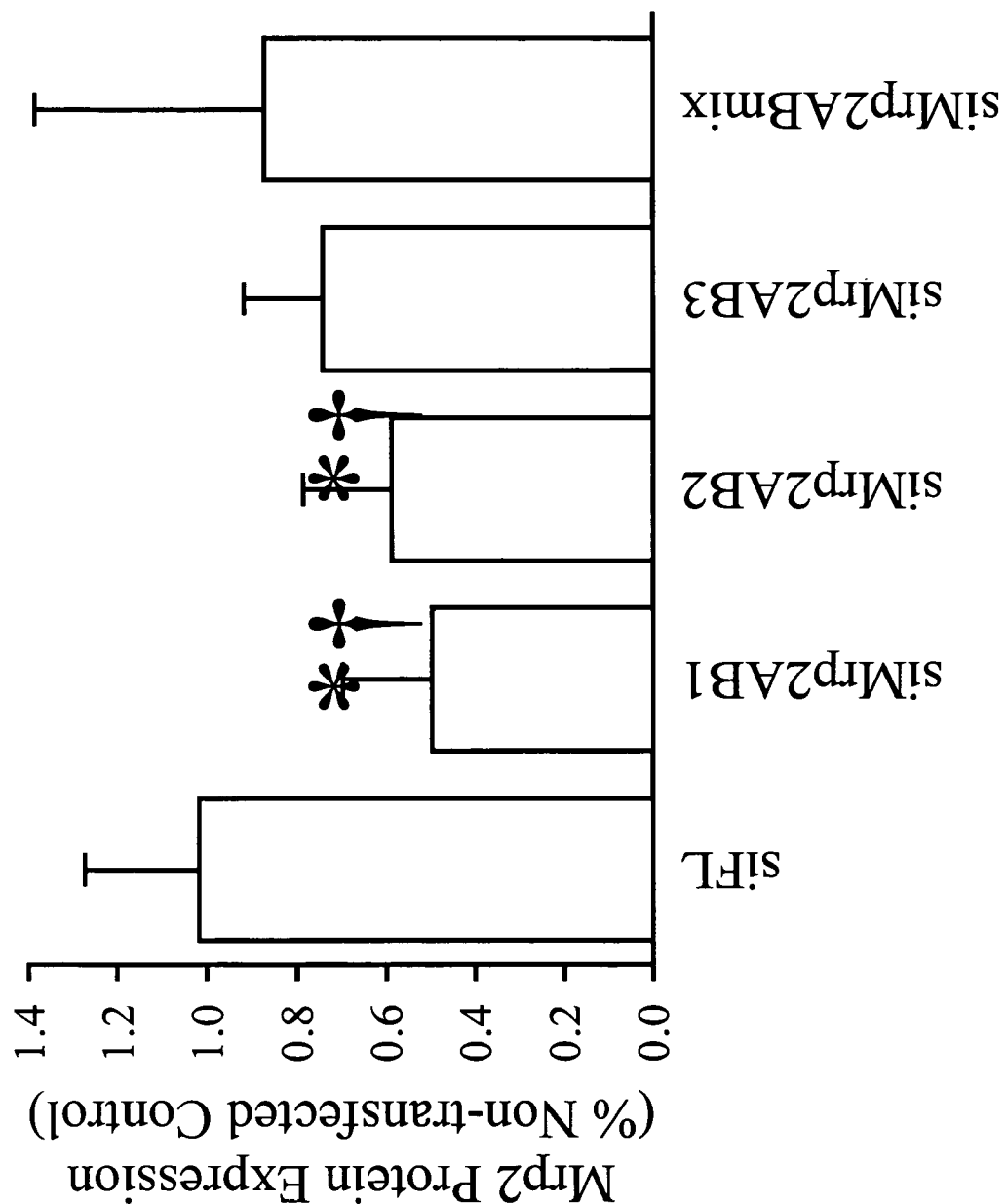
FIG. 12B represents the relative expression ratio of actin-normalized Mrp2 in siRNA-treated cells to non-transfected control. Mean±SD (n=4), *p<0.05 siRNA-transfected vs. untransfected control, †p<0.05 siMrp2-transfected vs. siFL (one-way ANOVA with Tukey's post-hoc test).

To evaluate the specificity of the knockdown effect in siMrp2-treated cells, the expression of Mrp3 (SEQ ID NO: 2), a protein of 45% identity to Mrp2 (SEQ ID NO: 1) was examined. Immunoblot analysis data indicated that the expression levels of Mrp3 in SCRH treated with siMrp2AB1 (SEQ ID NO: 3), siMrp2AB2 (SEQ ID NO: 4) and siMrp2AB3 (SEQ ID NO:5), a mixture of these three, or siFL (SEQ ID NO: 7) were the same as those in non-transfected cells (89±11, 96±15, 86±11, 89±19, 96±6% non-transfected control, respectively; FIGS. 12A and 12B).

Radixin is the dominant ezrin-radixin-moesin (ERM) protein in rodent liver, and it is located primarily at the bile canalicular membrane, resulting in a chronic hyperbilirubinemia phenotype typical in Mrp2-deficient mice. Expression of radixin, the protein necessary for the correct localization of Mrp2 on the canalicular membrane, in SCRH increased over time in culture (day 2=111, day 3=153, day 4=189% expression on day 1). Radixin expression levels were not altered in SCRH treated with siMrp2 or siFL when compared with non-transfected SCRH (siMrp2AB1=95±17, siMrp2AB2=100±8, siMrp2AB3=103±7, siMrp2Abmix=101±8, siFL=103±10% non-transfected control). Thus, the reduction in the efflux of CDF into the canalicular networks in siMrp2-treated SCRH was not due to the alterations in Mrp3 or radixin. Rather, it was a direct consequence of the suppression of Mrp2.

To investigate the consequences of the suppression of Mrp3 (SEQ ID NO: 2) in SCRH, Mrp3 expression was modulated utilizing the same approach as described above. SCRH were treated with siRNA (generally referred to herein and in the Figures as siMrp3; SEQ ID NO: 6) targeting the nucleotides 1950-1970 of the Mrp3 cDNA. Immunoblot analysis confirmed a decrease in Mrp3 protein expression with no change in expression of Mrp2 when compared with cells transfected with siFL (SEQ ID NO: 7) and non-transfected cells (FIG. 13A). The functional assay with CDF, which also is an Mrp3 substrate, indicated that CDF fluorescence in canalicular networks was more intense than in siFL-transfected or non-transfected cells (FIG. 13B).

Figure 13D:
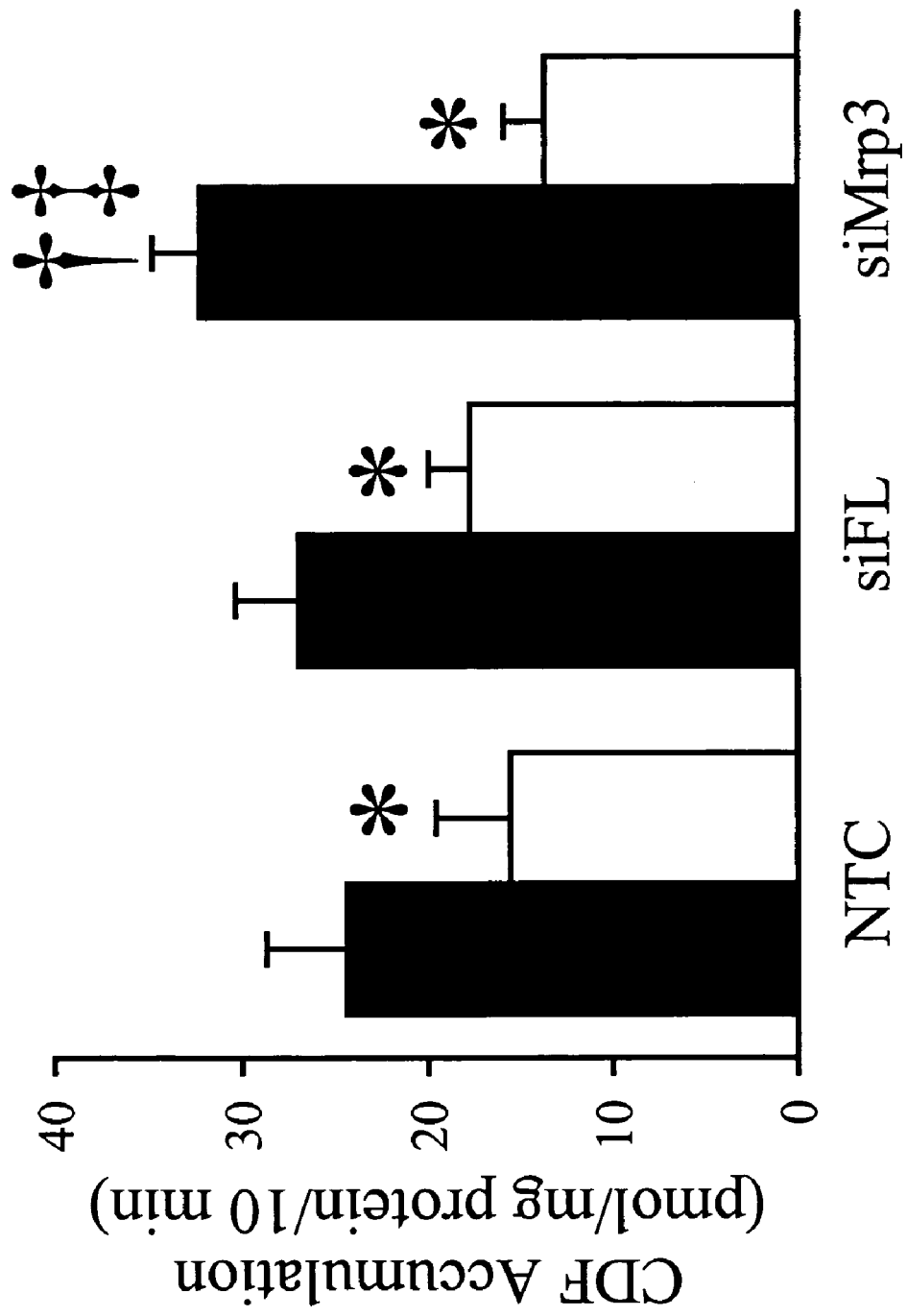
FIG. 13D is a graph showing CDF accumulation in cells+bile canaliculi (closed bars) and cells only (open bars) in siMrp3-, siFL-transfected, and non-transfected SCRH following 10 min incubation with 2 μM CDF diacetate and 30 min washout. NTC=non-transfected control. Mean±SD (n=6), *p<0.05 cells+bile canaliculi vs. cells only, †p<0.05 siMrp2-transfected vs. NTC, ‡p<0.05 siMrp2-transfected vs. siFL-transfected (two-way ANOVA with Tukey's post-hoc test).

Immediately following incubation with CDF diacetate, no apparent effect of Mrp3 knockdown on CDF accumulation in both cells+bile canaliculi and cells only was noted. The difference became apparent after a 30 min washout to allow CDF accumulated in hepatocytes to undergo appreciable basolateral excretion (FIG. 13D). CDF accumulation in siMrp3-transfected cells+bile canaliculi was significantly higher than in control non-transfected cells+bile canaliculi (32.3±2.5 vs. 24.4±4.3 pmol/mg protein/10 min). In contrast, CDF accumulation in cells only was not changed by Mrp3 knockdown (13.7±2.2 vs. 15.6±4.0 pmol/mg protein/10 min). The biliary excretion index of CDF after 30 min washout was increased ~60% (57.5 vs. 36.2%).

Discussion

Although chemically synthesized siRNA is available commercially, the T7 RNA polymerase method proved to be a cost-effective way to synthesize small amounts of siRNA for preliminary screening (Donze and Picard, $Nucleic\ Acids\ Res.$ 30:e46, 2002). To ensure the siRNA quality produced by this method, siRNA targeting firefly luciferase (siFL) with proven knockdown effect (Miyagishi and Taira, $Nat.\ Biotechnol.$ 20:497-500, 2002) was synthesized and used to examine the knockdown effect on the expression of firefly luciferase expressed from the PGL3-FL plasmid in HepG2 cells. Firefly luciferase activity was decreased in a dose-dependent manner by siFL, indicating that siRNA synthesized by the T7 RNA polymerase method had a significant knockdown effect.

Alterations in either the expression or localization of Mrp2 can lead to altered Mrp2 function. In vivo studies have demonstrated that radixin, the dominant bile canalicular ezrin-radixin-moesin protein in rodent liver, directly binds to the C-terminal cytoplasmic domain of Mrp2; the interaction between radixin and Mrp2 is necessary for the correct localization of Mrp2 on the canalicular membrane (Kocher et al., $Lab.\ Invest.$ 79:1161-1170, 1999; Kojima et al., $J.\ Hepatol.$ 39:693-702, 2003). When radixin was knocked out in mice, Mrp2 was mislocalized and malfunctioned (Kikuchi et al., Nat. Genet. 31:320-325, 2002). After isolation of hepatocytes with collagenase, Mrp2 is internalized. In SCRH, Mrp2 re-localizes to the canalicular membrane over time in culture (Zhang et al., *AAPS Pharm. Sci.* 3:Abstract 1522-1059, 2001). Expression of radixin in SCRH increased over time in culture, consistent with the re-localization of Mrp2 to the canalicular membrane. Radixin expression levels were not altered in SCRH treated with siMrp2 when compared with those transfected with siFL or non-transfected SCRH. These data exclude the possibility that modulation of Mrp2 function by siMrp2 was mediated via the radixin pathway.

Treatment of SCRH with siMrp2 essentially produced a transient Mrp2-knockdown model (FIGS. 12A and 13A). Qualitatively, the decrease in Mrp2 function was demonstrated by fluorescence microscopy using the fluorescent Mrp2 substrate, CDF. Fluorescence in the canalicular networks of SCRH treated with siMrp2 was markedly decreased compared to SCRH treated with siFL or non-transfected cells. Quantitatively, transfection of SCRH with siMrp2 decreased the fraction of CDF in cells+bile canaliculi found in bile canaliculi from to 16.5 to 9.3%. The extent of decrease of CDF biliary excretion (~45%) is in good agreement with the extent of Mrp2 knockdown (~50%). Decreased CDF disposition was due to decreased Mrp2 protein levels, and not compromised cell viability, as demonstrated by the lack of increase in lactate dehydrogenase activity in the medium of siMrp2-transfected SCRH.

Knockdown of Mrp3 did not change expression of Mrp2 when compared with cells transfected with siFL or non-transfected cells (FIG. 13A). The functional assay with CDF, which also is an Mrp3 substrate, indicated that CDF fluorescence in the canalicular networks was more intense than in siFL-transfected or non-transfected cells (FIG. 13B). Transfection of SCRH with siMrp3 significantly increased accumulation of CDF in cells+bile canaliculi, but not in cells only (FIG. 13D), resulting in ~60% increase in the fraction of CDF accumulated in cells+bile canaliculi found in bile canaliculi. Knockdown of Mrp3 resulted in re-direction of the route of CDF excretion into bile, hence canalicular fluorescence in siMrp3-treated SCRH was higher than in control cells. siMrp3-treated SCRH represent a transient Mrp3-knockdown model, which is as yet unavailable in vivo.

As demonstrated by this work, RNA interference is a powerful tool in the study of the role of specific protein in drug disposition. The majority of current knowledge regarding the role of transport protein in hepatic clearance comes from three types of experimental setups: recombinant expression systems, and knockout/mutant animals. While much progress has been made with these tools in the study of transporter function, current experimental systems have limitations, which are discussed below. Many of these limitations are not relevant to RNA interference.

Recombinant protein may not always be representative of in vivo protein in the species of interest, due to differences in transcription, translation, and post-translational modifications in the host cell. For example, Sf9 cells, which are often used as the host system for expression of many ATP-binding cassette transporters, greatly underglycosylate the recombinant protein, resulting in transporters of lower molecular weight (Germann et al., *Biochemistry* 29:2295-2303, 1990). Furthermore, recent research indicates that certain compounds may be substrates of more than one transporter at a given plasma membrane domain. For example, both Mrp2 and the breast cancer resistance protein excrete sulfate conjugates of xenobiotics across the hepatic canalicular membrane into bile (Xiong et al., *J. Pharmacol. Exp. Ther.* 295: 512-518, 2000). Likewise, hepatic uptake may be mediated by more than one transporter. The opioid peptide, [D-penicillamine$^{2,5}$]enkephalin, is taken up into hepatocytes by all three organic anion transporting polypeptide isoforms (Cattori et al., *Pflugers Arch.* 443:188-195, 2001). Therefore, accurate in vivo interpretation of the importance of transport of a compound by a recombinant transporter may be very difficult.

While knockout or naturally occurring mutant animals have greatly advanced the understanding of the role of individual transporters in vivo, upregulation of complementary transport mechanisms in these animals may confound data interpretation. For example, in Mrp2-deficient EHBR rats, biliary excretion of taurocholic acid is impaired, not because Mrp2 mediates biliary excretion of this bile acid, but because basolateral Mrp3 is highly upregulated in the livers of these rats, resulting in more efficient basolateral excretion limiting available substrate for biliary excretion (Akita et al., *Pharm. Res.* 18:1119-1125, 2001). Interpretation of data obtained from knockout or mutant animals must take into consideration potential alterations in complementary pathways, which may not always be well understood.

As demonstrated here, RNA interference allows specific and rapid knockdown of a protein of interest. Transfection of SCRH with siMrp2 specifically decreased Mrp2 protein, but not the closely related Mrp3. Likewise, knockdown of Mrp3 did not affect Mrp2 protein levels. In naturally occurring mutants lacking Mrp2, e.g. EHBR rats, Mrp3 is highly upregulated in the liver (Akita et al., *Pharm. Res.* 18:1119-1125, 2001). However, knockdown of Mrp2 did not alter Mrp3 protein levels two days after transfection of hepatocytes with siMrp2. The rate of protein knockdown with siRNA is dictated by the half-life of the protein, which apparently for Mrp2 is short enough that significant decrease in Mrp2 levels can be achieved before a notable increase in Mrp3 occurs.

Overall, modulation of drug transporters by siRNA treatment in SCRH is a feasible approach for studying the expression and function of drug transport proteins. RNA interference offers unique advantages over experimental designs used currently for the study of transport protein. The major advantages of siRNA include specificity of knockdown and maintenance of expression of complementary transport mechanisms in primary cells, which maintain expression of other relevant protein.

REFERENCES

The references listed below as well as all references cited in the specification are incorporated herein by reference to the extent that they supplement, explain, provide a background for or teach methodology, techniques and/or compositions employed herein.

Akita et al., *Pharm. Res.* 18:1119-1125, 2001.
Annaert et al., *Drug Metab. Dispos.* 29:1277-1283, 2001.
Bass, *Nature* 411:428-429, 2001.
Bernstein et al., *Nature* 409:363-366, 2001.
Boyer and Soroka, *Gastroenterology* 109:1600-1611,1995.
Bremnes et al., *Cancer Res.* 49:2460-2464,1989.
Cabaud and Wroblewski, *Am. J. Clin. Pathol.* 30:234-236, 1958.
Canadian Patent Application No. 2,359,180.
Cattori et al., *Pflugers Arch.* 443:188-195, 2001.
Chen et al., *Pharm. Res.* 14:345-350,1997.
Donze and Picard, *Nucleic Acids Res.* 30:e46, 2002.
Dunn et al., *FASEB J.* 3:174-177,1989.
Elbashir et al. *Nature* 411:494-498, 2001a.
Elbashir et al., *Genes Dev* 15:188-200, 2001b.
Eriksson et al., *Acta. Physiol. Scand.* 95:1-5, 1975.
Fire et al., *Nature* 391:806-811,1998.

Fire, *Trends Genet* 15:358-363,1999.
Germann et al., *Biochemistry* 29:2295-2303, 1990.
Hammond et al., *Nature* 404:293-296, 2000.
Haugland, *Molecular Probes: Handbook of Fluorescent Probes and Research Chemicals* (1992-1994), p.134, Molecular Probes, Inc., 1992.
Inoue et al., *Biochim. Biophys. Acta.* 833:211-216,1985.
Kikuchi et al., *Nat. Genet.* 31:320-325, 2002.
Kocher et al., *Lab. Invest.* 79:1161-1170,1999.
Kojima et al., *J. Hepatol.* 39:693-702, 2003.
Kool et al., *Proc. Natl. Acad. Sci. USA* 96:6914-6919 1999.
Laznicekand et al., *Eur. J. Drug Met. Pharmacokinet.* 19:21-26, 1994.
LeCluyse et al., *Am. J. Physiol.* 266(Cell Physiol. 35):C1764-1774, 1994.
LeCluyse et al., Cultured rat hepatocytes, in *Models for Assessing Drug Absorption and Metabolism* (Borchard et al. eds), pp 121-160, Plenum Press, New York, 1996.
Liu et al., *Pharm. Res. Init.*13:S-393 (8003), 1996.
Liu et al., *Hepatology* 24:370A (973), 1996.
Liu et al., *Pharm. Res.* 24:S-459 (3007),1997.
Liu et al., *Hepatology* 26:297A (675), 1997.
Liu et al., *Pharm. Sci.* 1 :S-119, 1998.
Liu et al., *Pharm. Res.,* 15:1533-1539, 1998.
Liu et al., *J. Pharmacol. Exp. Ther.* 289:1592-1599, 1999.
Masuda et al., *Cancer Res.* 57:3506-10, 1997.
Miyagishi and Taira, *Nat. Biotechnol.* 20:497-500, 2002.
Norris et al., *N. Eng. J. Med.* 334:231-238,1996.
Nykanen et al., *Cell* 107:309-321, 2001.
Pang et al., *J. Pharmacokinet Biopharm.* 5:625-653, 1977.
Parkinson, A., Biotransformation of Xenobiotics in *Casarett and Doull's Toxicology. The Basic Science of Poisons.*, 5th Ed. (Klaassen, C. D. ed.) pp.113-186, McGraw Hill, New York, 1996.
PCT International Publication No. WO 99/32619.
PCT International Publication No. WO 99/07409.
PCT International Publication No. WO 00/01846.
PCT International Publication No. WO 00/44895.
PCT International Publication No. WO 00/44914.
PCT International Publication No. WO 00/63364.
PCT International Publication No. WO 01/04313.
PCT International Publication No. WO 01/29058.
PCT International Publication No. WO 01/36646.
PCT International Publication No. WO 02/44321.
PCT International Publication No. WO 01/68836.
PCT International Publication No. WO 01/75164.
PCT International Publication No. WO 01/92513.
PCT International Publication No. WO 02/055692.
PCT International Publication No. WO 02/055693.
Pollack et al., *J. Pharmacol. Exp. Ther.* 18:197-202, 1989.
Sandusky et al., *Histopathology* 41:65-74, 2002.
Seglen, *Methods in Cell Biology* (13th Ed., Prescott D. M. Eds.) pp. 30-78, Academic Press, New York, 1976.
Sidhu et al., *Pharmacogenetics* 5:24-36, 1993.
Silver et al., *ISSX Proceedings (San Diego, Calif. USA)* pp. 387,1996.
Summerton & Weller, *Antisense Nucleic Acid Drug Dev* 7:187-95, 1997.
Summerton, *Biochim Biophys Acta* 1489(1): 141-58,1999.
Utesch et al., *In Vitro Cell Dev. Biol.* 27A:858-863, 1991.
Wianny & Zernicka-Goetz, *Nature Cell Biol* 2:70-75, 1999.
Xiong et al., *J. Pharmacol. Exp. Ther.* 295:512-518, 2000.
Zhang et al., *AAPS Pharm. Sci.* 3:Abstract 1522-1059, 2001.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of screening a candidate compound for susceptibility to biliary excretion by a hepatocyte transport protein, the method comprising:
   (a) providing a first cell culture comprising a plurality of hepatocytes and at least one bile canaliculus, at least one of the hepatocytes comprising a hepatocyte transport protein, wherein the expression of the hepatocyte transport protein is inhibited;
   (b) providing a second cell culture comprising a plurality of hepatocytes and at least one bile canaliculus, at least one of the hepatocytes comprising a hepatocyte transport protein, wherein the expression of the hepatocyte transport protein is not inhibited;
   (c) exposing a candidate compound to the first and second cell cultures; and
   (d) determining an amount of the candidate compound in the at least one bile canaliculus in the first and second cell cultures, wherein the presence of a reduced amount of the candidate compound in the at least one bile canaliculus of the first cell culture as compared to an amount of the candidate compound in the at least one bile canaliculus of the second cell culture indicates the susceptibility of the candidate compound to biliary excretion by the hepatocyte transport protein.

2. The method of claim 1, wherein the hepatocytes are isolated from a source selected from the group consisting of rat, human, monkey, ape, cat, dog, pig, hog, cattle, oxen, sheep, horses, turkeys, chickens, ducks and geese.

3. The method of claim 1, wherein the culture of hepatocytes further comprises a long-term culture of hepatocytes.

4. The method of claim 1, wherein the culture of hepatocytes further comprises a canalicular network.

5. The method of claim 1, wherein the culture of hepatocytes is further characterized as having a configuration selected from the group consisting of clusters of hepatocytes, aggregates of hepatocytes, at least one layer of hepatocytes, and combinations thereof.

6. The method of claim 5, wherein the hepatocytes are embedded in a matrix.

7. The method of claim 5, wherein the culture of hepatocytes further comprises a sandwich culture of hepatocytes, the sandwich culture comprising at least one layer of hepatocytes and at least one bile canaliculus with the at least one layer of hepatocytes.

8. The method of claim 7, wherein the sandwich culture of hepatocytes further comprises a long-term sandwich culture of hepatocytes.

9. The method of claim 7, wherein the at least one layer of hepatocytes is sandwiched between two layers of matrix.

10. The method of claim 9, wherein the matrix is selected from the group consisting of a biological matrix medium, a synthetic matrix medium, and combinations thereof.

11. The method of claim 10, wherein the biological matrix medium is selected from the group consisting of collagens, laminins, basement membrane-derived complexes, derivatives thereof and combinations thereof.

12. The method of claim 1, further comprising screening a plurality of candidate compounds simultaneously.

13. The method of claim 1, wherein inhibiting expression of the hepatocyte transport protein comprises introducing a ribonucleic acid (RNA) into at least one of the plurality of hepatocytes in the first cell culture in an amount sufficient to inhibit expression of the hepatocyte transport protein, wherein the RNA comprises a ribonucleotide sequence having a region complementary to a coding strand of a gene encoding the transport protein.

14. The method of claim 13, wherein the gene encodes a polypeptide selected from the group consisting of NTCP, OATP1A1, OATP1A2, OATP1A4, OATPB2, OATP1B1, OATP1B3, OATP2B1, OAT2, OAT3, OAT4, OCT1, OCT3, OCTN1, OCTN2, BSEP, MRP1, MRP2, MRP3, MRP4, MRP5, MRP6, MRP7, MRP8, MRP9, MDR1, MDR1A/B, MDR2, MDR3, BCRP, ABCG5, ABCG8, and FIC-1.

15. The method of claim 14, wherein the gene comprises a nucleotide sequence of one of SEQ ID NOs: 1 and 2.

16. The method of claim 13, wherein the RNA comprises a double-stranded region comprising a first strand comprising a ribonucleotide sequence having a region that is complementary to the coding strand of the gene encoding the hepatocyte transport protein and a second strand comprising a ribonucleotide sequence that is complementary to the first strand, and wherein the first strand and the second strand hybridize to each other to form the double-stranded molecule.

17. The method of claim 16, wherein the double stranded region is at least 15 basepairs in length.

18. The method of claim 17, wherein the double stranded region is between 15 and 50 basepairs in length.

19. The method of claim 18, wherein the double stranded region is between 15 and 30 basepairs in length.

20. The method of claim 13, wherein the RNA comprises one strand that forms a double-stranded region by intramolecular self-hybridization.

21. The method of claim 20, the double-stranded region is complementary over at least 19 bases.

22. The method of claim 16, wherein the RNA comprises two separate strands that form a double-stranded region by intermolecular hybridization that is complementary over at least 19 bases.

23. The method of claim 13, wherein the RNA comprises a nucleotide sequence of one of SEQ ID NOs: 3, 4 and 5.

24. The method of claim 13, wherein the expression of the gene encoding the transport protein is inhibited by at least 10%.

25. The method of claim 13, further comprising introducing a vector into at least one of the plurality of hepatocytes in the first cell culture, wherein the vector encodes the RNA.

26. The method of claim 13, wherein introducing the RNA into at least one of the plurality of hepatocytes in the first cell culture comprises transfecting the RNA into at least one of the plurality of hepatocytes.

27. The method of claim 13, wherein introducing the RNA into at least one of the plurality of hepatocytes in the first cell culture comprises infecting at least one of the plurality of hepatocytes with a recombinant virus encoding the RNA.

28. The method of claim 1, wherein the amount of the candidate compound in the at least one bile canaliculus is determined by calculating a biliary clearance value for the culture.

* * * * *

UNITED STATES PATENT AND TRADEMARK OFFICE
CERTIFICATE OF CORRECTION

PATENT NO. : 7,601,494 B2
APPLICATION NO. : 10/842404
DATED : October 13, 2009
INVENTOR(S) : Tian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 846 days.

Signed and Sealed this

Fifth Day of October, 2010

David J. Kappos
*Director of the United States Patent and Trademark Office*